(12) United States Patent
Schüle et al.

(10) Patent No.: US 10,299,467 B2
(45) Date of Patent: May 28, 2019

(54) ANIMAL MODEL FOR TYPE 2 DIABETES AND OBESITY

(71) Applicant: Universitaetsklinikum Freiburg, Freiburg (DE)

(72) Inventors: Roland Schüle, Weisweil (DE); Delphine Duteil, Illkirch (FR); Eric Metzger, Neuf-Brisach (FR); Thomas Günther, Freiburg (DE)

(73) Assignee: UNIVERSITAETSKLINIKUM FREIBURG, Freiburg (DE)

( * ) Notice: Subject to any disclaimer, the term of this patent is extended or adjusted under 35 U.S.C. 154(b) by 567 days.

(21) Appl. No.: 14/439,609

(22) PCT Filed: Oct. 31, 2013

(86) PCT No.: PCT/EP2013/072772
§ 371 (c)(1),
(2) Date: Apr. 29, 2015

(87) PCT Pub. No.: WO2014/068033
PCT Pub. Date: May 8, 2014

(65) Prior Publication Data
US 2015/0296757 A1    Oct. 22, 2015

(30) Foreign Application Priority Data

Oct. 31, 2012  (EP) ................................. 12007446

(51) Int. Cl.
*A01K 67/027* (2006.01)
*C12N 9/02* (2006.01)
*C12N 15/113* (2010.01)

(52) U.S. Cl.
CPC ........ *A01K 67/0276* (2013.01); *C12N 9/0004* (2013.01); *C12N 15/1137* (2013.01); *A01K 67/0278* (2013.01); *A01K 2207/15* (2013.01); *A01K 2207/25* (2013.01); *A01K 2217/072* (2013.01); *A01K 2217/077* (2013.01); *A01K 2227/105* (2013.01); *A01K 2267/0362* (2013.01); *C12N 2310/14* (2013.01)

(58) Field of Classification Search
CPC .......... A01K 67/026; A01K 2267/0362; A01K 2227/105; A01K 2207/25; C12N 9/0004
USPC .................................................. 800/18, 9, 3
See application file for complete search history.

(56) References Cited

FOREIGN PATENT DOCUMENTS

EP          2258858 A1    12/2010
WO    WO 2012/156537 A2    11/2012

OTHER PUBLICATIONS

Mullins et al. (1996) J. Clin. Invest., vol. 98(11), S37-S40.*
Prelle et al. (2002) Anat. Histol. Embryol., vol. 31, 169-186.*
Munoz et al. (2009) Stem Cell Rev. and Rep., vol. 5, 6-9.*
Wheeler (2001) Theriogenology. vol. 56, 1345-1369.*
Niemann et al (2005) Rev. Sci, Tech. Off. Int. Spiz. vol. (24), 285-298.*
Clark et al. (2003) Nature Reviews: Genetics. vol. 4, 825-833.*
Pojoga et al. (2011) Am. J. Physiol Heart Circ. Physiol., vol. 301, H1862-H1871, first published Aug. 26, 2011.*
Re et al. (2009) The Ochsner Journal, vol. 9, 133-136.*
Campbell et al. (2011) Can Fam Physician, vol. 57, 997-1002.*
Arian Abdulla et al., Journal of Biochemical and Pharmacological Research, vol. 1, No. 1, pp. 56-63, Mar. 2013.
Delphine Duteil et al., Nature Communications, vol. 5, No. 4093, pp. 1-14, Jun. 2014.
Tom Heightman, Current Chemical Genomics, vol. 5, no. suppl. 1, pp. 62-71, Aug. 2011.
Shinjiro Hino et al., Nature Communications, vol. 3, pp. 1-12, Mar. 2012.
Melina Musri et al., Journal of Biological Chemistry, vol. 285, No. 39, pp. 30034-30041, Sep. 2010.
Luminita Pojoga et al., American Journal of Physiology: Heart and Circulation Physiology, vol. 301, No. 5, pp. H1862-H1871, Nov. 2011.
Marpadga Reddy et al., Circulation Research, vol. 103, No. 6, pp. 615-623, Sep. 2008.
Thomas Seyfried et al., Nutrition & Metabolism, vol. 7, No. 1, pp. 1-22, Jan. 2010.
A Sprüssel et al., Leukemia, vol. 26, No. 9, pp. 2039-2051, Sep. 2012.
Keisuke Tateishi et al., Nature (London), vol. 458, No. 7239, pp. 757-761, Apr. 2009.
Hironori Waki et al., Current Diabetes Reports, vol. 12, No. 6, pp. 673-685, Oct. 2012.
Jonathan Williams et al., American Journal of Hypertension, vol. 25, No. 7, pp. 812-817, Jul. 2012.

* cited by examiner

*Primary Examiner* — Anne Marie S Wehbe
(74) *Attorney, Agent, or Firm* — Chalin A. Smith; Smith Patent, LLC

(57) ABSTRACT

The present invention relates to the use of a genetically modified non-human animal as an animal model for obesity or obesity-related disorders, wherein the amount of Lysine-specific Demethylase 1 (LSD1) in at least one tissue or at least one cell type of said animal is reduced.

4 Claims, 38 Drawing Sheets
Specification includes a Sequence Listing.

Figur 28

Figure 29
a
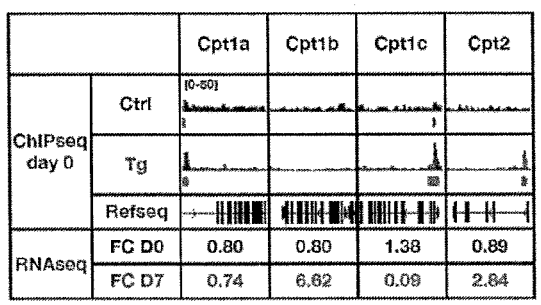
b
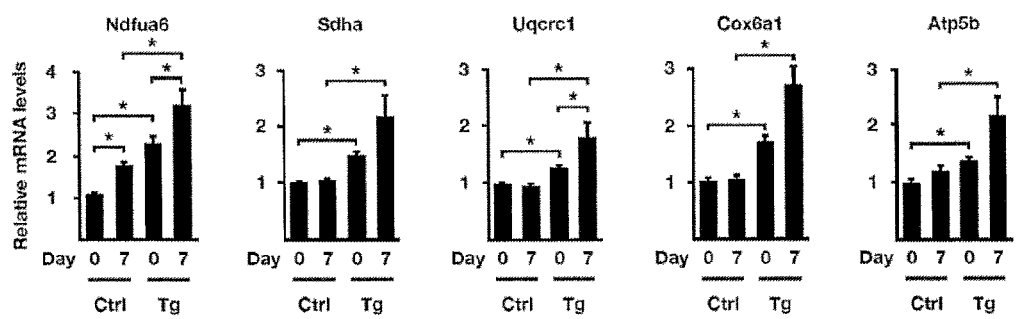
c
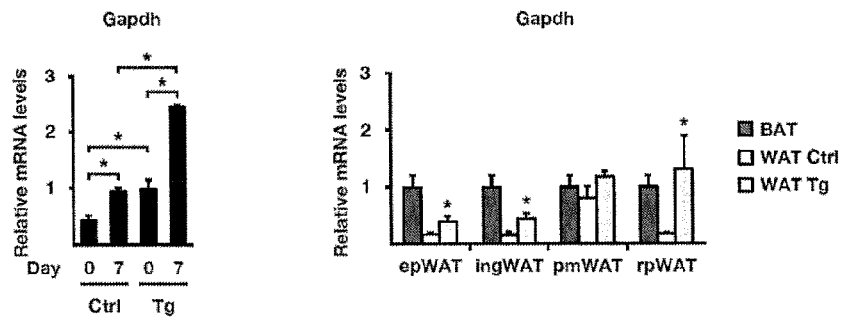
d
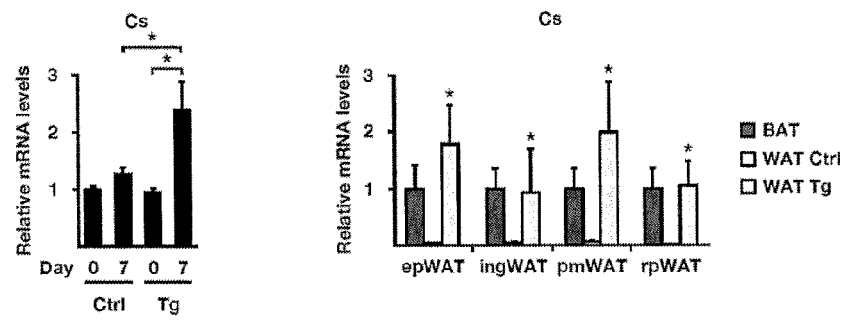

Figure 32
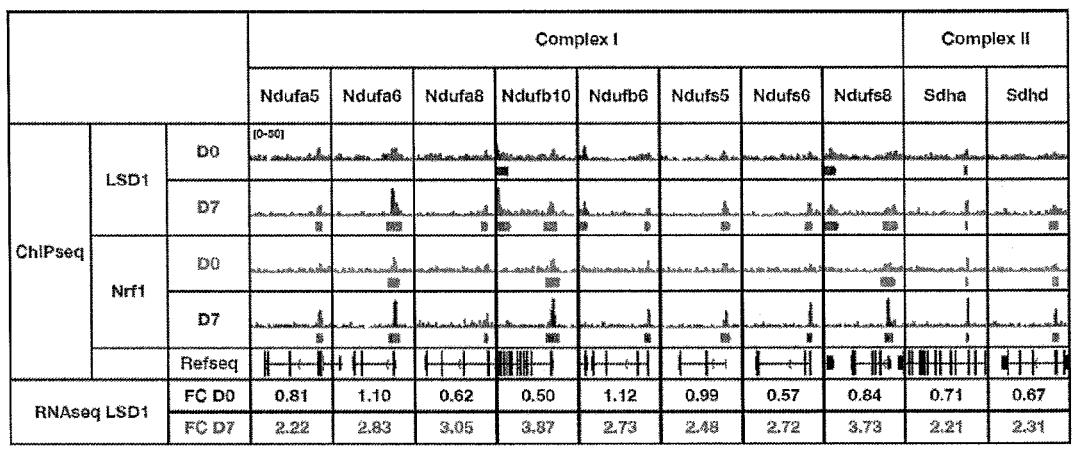
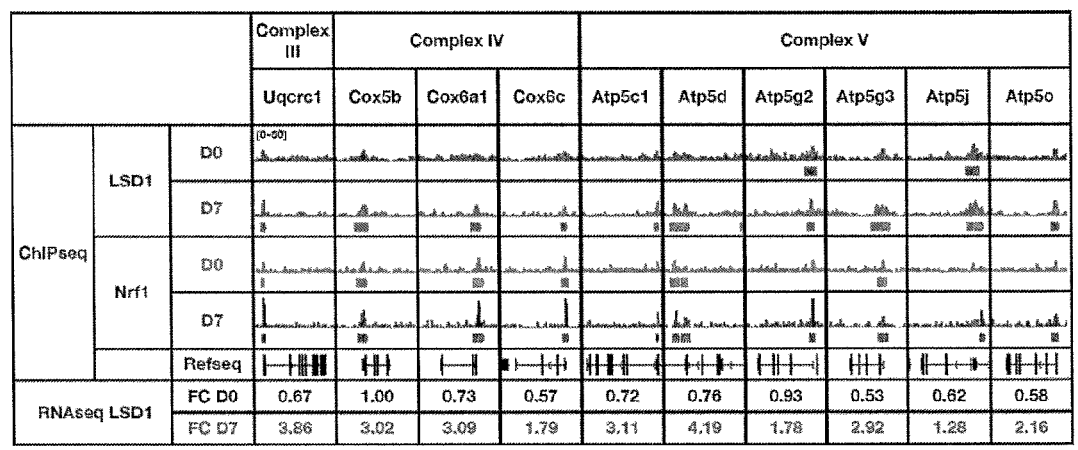

ANIMAL MODEL FOR TYPE 2 DIABETES AND OBESITY

PRIORITY

This application corresponds to the U.S. national phase of International Application No. PCT/EP2013/072772, filed Oct. 31, 2013, which, in turn, claims priority to European Patent Application No. 12.007446.3 filed Oct. 31, 2012, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Apr. 29, 2015, is named LNK_163 US_sequencelisting3_ST25.txt and is 97,567 bytes in size.

FIELD OF THE INVENTION

The present invention relates to the use of a genetically modified non-human animal as an animal model for type 2 diabetes, obesity and related disorders, wherein the amount of Lysine-specific Demethylase 1 (LSD1) in at least one tissue or at least one cell type of said animal is reduced. The invention further pertains to a method for identifying a compound useful in the treatment and/or prevention of obesity or an obesity-related disorder, and to an LSD1 modulator for use in the treatment and/or prevention of obesity or an obesity-related disorder.

BACKGROUND OF THE INVENTION

In industrialized countries, characterized by a sedentary lifestyle and high-caloric diet, energy balance is often deregulated leading to the development of obesity, dyslipidemia, hyperglycemia, and insulin resistance (type 2 diabetes). Among other organs, adipose tissue is an important regulator of energy balance (Langin, 2010). There are two major types of adipose tissue in mammals, white adipose tissue (WAT) and brown adipose tissue (BAT), which are present in different compartments and show distinct metabolic characteristics. Unilocular WAT is highly adapted to store excess energy in the form of triglycerides and is mainly located in the abdominal and subcutaneous areas. Conversely, multilocular cells from BAT, which are mainly located in the interscapular area (iBAT), oxidize chemical energy to produce heat as a defense against hypothermia and obesity (Himms-Hagen, 1990; Langin, 2010). Fatty acid oxidation and heat production by brown adipocytes is due to the intense metabolic activity of mitochondria, which express uncoupling protein 1 (Ucp1) (Ricquier and Bouillaud, 2000). WAT and BAT have long been assumed to have the same embryonic origin. However, recent evidence suggests that brown and white adipocytes are derived from two different precursors (Seale et al., 2008). These precursors can be discriminated by the presence or absence of the transcription factor myogenic factor 5 (Myf5), with brown adipocytes being derived from Myf5-positive and white adipocytes derived from Myf5-negative cells, respectively (Seale et al., 2008). In response to environmental cues such as cold or treatment with β3-adrenergic agonists, appearance of brown fat-like cells has been observed in mouse WAT (Himms-Hagen et al., 1994; Himms-Hagen et al., 2000; Young et al., 1984). These brown fat-like cells are called beige or brite cells. Interestingly, these beige fat cells are not derived from Myf5-expressing precursors (Seale et al., 2008), raising questions about their origin. It has been speculated that beige cells might originate from differentiation of a specific pool of precursor cells already present in WAT (Seale et al., 2011; Wu et al., 2012). Alternatively, beige fat cells could arise from direct conversion of white adipocytes (Granneman et al., 2005; Himms-Hagen et al., 2000; Loncar, 1991). Recently, Wu and colleagues proposed that beige cells exhibit a gene expression pattern distinct from either white or brown fat and that previously identified brown fat deposits in adult humans are indeed composed of beige adipocytes (Wu et al., 2012). However, it is neither known whether beige adipocytes constitute metabolically active fat cell nor are the transcriptional cascades that control the transformation of white to beige adipose tissues have been determined so far.

Over the last decade, evidence accumulated that epigenetics contribute to regulation of adipogenesis. In particular, posttranslational modifications of histone H3 lysines have been linked to either transcriptional activation or repression, depending on the modified residue. Methylation of lysine 4 in histone H3 (H3K4) correlates with gene activation, whereas methylation of lysine 9 or 27 in histone H3 (H3K9 or H3K27, respectively) is associated with transcriptional repression. As an example illustrating the key role of lysine methylation in adipocyte differentiation, it was reported that H3K4 methylation was required for Pparg and C/ebpa expression and thus positively regulates adipogenesis (Cho et al., 2009). In contrast, methylation of H3K27 by the methyltransferase Ezh2 promotes adipogenesis by repressing the Wnt signaling (Wang et al., 2010). Lysine-specific demethylase 1 (LSD1), the first histone lysine demethylase described, is an amine oxidase that mediates histone demethylation via a FAD-dependent oxidative reaction. It has been shown that LSD1 selectively removes mono- and dimethyl groups from H3K4 or H3K9, thereby causing either repression or activation of gene transcription (Garcia-Bassets et al., 2007; Lee et al., 2005; Metzger et al., 2010; Metzger et al., 2005; Shi et al., 2004; Wang et al., 2009a; Wang et al., 2009b) (Zhu Ms). Recent in vitro studies suggest that LSD1 might play a role during fat cells differentiation in vitro (Hino et al., 2012). Hino et al. observe upregulation of LSD1 protein levels in mice on a high fat diet. In addition, their ex vivo experiments with adipocytes from mice on a high fat diet suggest that energy expenditure genes are upregulated upon knockdown of LSD1. This teaches away from the present invention.

SUMMARY OF THE INVENTION

The inventors of this application have shown that heterozygous mice in which one allele of the LSD1 gene has been disrupted and which show reduced expression of Lsd1 are prone to obesity and type 2 diabetes. These mice and other non-human animals having a reduced expression of Lsd1 are valuable tools for studying established and potential agents to treat type 2 diabetes and related diseases such as or insulin resistance and obesity.

In addition, the inventors found that transgenic overexpression of Lsd1 in mice improved the metabolic profile of the transgenic mice when fed a high-caloric diet, thereby attenuating obesity and diabetes.

The present invention therefore relates to the subject matter defined in items (1) to (30).

(1) The use of a modified non-human animal as an animal model for obesity or obesity-related disorders, wherein the amount of Lysine-specific Demethylase 1 (LSD1) in at least one tissue or at least one cell type of said animal is reduced, wherein the modified non-human animal preferably is a genetically modified non-human animal.

(2) The use of item (1), wherein the genetically modified non-human animal has a nucleic acid inserted in its genome, wherein the presence of the inserted nucleic acid in the genome of the animal results in reduced expression of LSD1.

(3) The use of item (1) or (2), wherein said genetic modification is a disruption of an allele of the endogenous gene encoding LSD1.

(4) The use of any one of the preceding items, wherein said animal is a non-human transgenic animal which is heterozygous for the disruption of the gene encoding LSD1.

(5) The use of any one of the preceding items, wherein the amount of LSD1 is reduced in tissue of said animal, preferably in adipose, liver or muscle of said animal.

(6) The use of any one of the preceding items, wherein said animal develops obesity after high fat diet.

(7) The use of any one of the preceding items, wherein said animal has at least one symptom of type 2 diabetes.

(8) The use of any one of the preceding items, wherein the animal is a rodent, preferably a mouse.

(9) A method for identifying a compound useful in the treatment and/or prevention of obesity or an obesity-related disorder, comprising (a) administering a test compound to a transgenic animal as defined in any one of items (1) to (8), and (b) determining the effect of the test compound on the initiation, maintenance, or progression of at least one obesity-related parameter in said transgenic animal, thereby identifying a compound that inhibits obesity or an obesity-related disorder.

(10) The method of item (9), wherein said obesity-related parameter is selected from the group consisting of the mass of white adipose tissue, the total mass of adipose tissue, glucose intolerance, and expression of a adipose tissue differentiation marker.

(11) A compound for use in the treatment and/or prevention of obesity or an obesity-related disorder, wherein said compound is capable of modulating LSD1 protein, the LSD1 gene or a target gene of LSD1.

(12) The compound for use according to claim 11, wherein the target gene of Lsd1 is selected from the group consisting of Nrf1, Prdm16 and Pgc-1α.

(13) A method for identifying a compound useful in the treatment and/or prevention of obesity or an obesity-related disorder, comprising (i) contacting a cell with a test compound; (ii) determining expression level of the LSD1 gene and/or of a target gene of LSD1; and (iii) selecting the compound if the test compound is capable of increasing the expression of the LSD1 gene and/or of the target gene of LSD1, as compared to a control cell which has not been contacted with the test compound.

(14) The method of item (13), wherein the cell is an adipocyte or a preadipocyte, preferably a mouse 3T3-L1 cell, a 3T3-F442 cell or a 10T1/2 cell.

(15) The use according to any one of items (1) to (8), the method of item (9) or (10), the LSD1 inhibitor for use according to item (11) or (12), or the method of item (13) or (14), wherein said obesity-related disorder is selected from the group consisting of insulin resistance, type II diabetes, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, and Lawrence-Moon syndrome.

(16) The use of a non-human transgenic animal whose genome comprises a stably integrated transgenic nucleotide sequence encoding Lysine-specific Demethylase 1 (LSD1) operably linked to a promoter for studying metabolism and/or as an animal model for metabolic disorders.

(17) The use of item (16), wherein said LSD1 is human LSD1.

(18) The use of item (16) or (17), wherein said LSD1 comprises at least amino acids 2 to 852 of the amino acid sequence as shown in SEQ ID NO:3.

(19) The use according to any one of items (16) to (18), wherein said transgenic nucleotide sequence comprises nucleotides 4 to 2556 of the nucleotide sequence as shown in SEQ ID NO:1.

(20) The use according to any one of items (16) to (19), wherein said LSD1 is overexpressed in the transgenic animal.

(21) The use of item (20), wherein said overexpression is present at least in white adipose tissue.

(22) The use according to any one of items (16) to (21), wherein said promoter is a Rosa26 promoter.

(23) The use according to any one of items (16) to (22), wherein said animal has a reduced weight relative to a wild type mouse.

(24) The use according to any one of items (16) to (23), which is a rodent, preferably a mouse.

(25) A use according to any one of items (16) to (24), wherein said animal does not comprise other transgenic nucleotide sequences.

(26) A method for identifying a compound useful in the treatment and/or prevention of a metabolic disorder, comprising (a) administering a test compound to a transgenic animal as defined in any one of items (16 to (25) and (b) determining the effect of the test compound on the initiation, maintenance, or progression of at least one metabolic parameter in said transgenic animal, thereby identifying a compound that inhibits the metabolic disorder, wherein said metabolic parameter is selected from the group consisting of the mass of white adipose tissue, the total mass of adipose tissue, glucose intolerance, expression of a adipose tissue differentiation marker.

(27) A method according to item (26), wherein said test compound is selected from the group consisting of LSD1 inhibitors or LSD1 modulators, modulators of androgen receptor, modulators of p53, and modulators of Rb.

(28) A LSD1 inhibitor or LSD1 modulator for use in the treatment and/or prevention of a metabolic disorder.

(29) The LSD1 inhibitor or LSD1 modulator of item (28), which is siRNA capable of inhibiting expression of the LSD1 gene.

(30) The use according to any one of items (16) to (25), the method of item (26) or (27), or the LSD1 inhibitor for use according to item (28) or (29), wherein said metabolic disorder is selected from the group consisting of eating disorders, body weight disorders, cachexia, anorexia, sarcopenia and wasting syndrome or disease.

DETAILED DESCRIPTION OF THE INVENTION

In a first embodiment, the present invention provides an animal model for type 2 diabetes, obesity and related disorders. One aspect of the invention is the use of a modified non-human animal as an animal model for obesity or obesity-related disorders, wherein the amount of Lysine-specific Demethylase 1 (LSD1) in at least one tissue or at least one cell type of said animal is reduced. The modified non-human animal may be a genetically modified non-human animal, preferably it is a transgenic non-human animal. The animals in accordance with this embodiment have a reduced amount of LSD1 in at least one tissue. These animals typically exhibit a reduced expression of LSD1 in one or more tissues. The reduced expression may or may not affect all tissues of the animal. Preferably, the amount of LSD1 protein or Lsd1 mRNA is reduced in fat tissue, e.g. in BAT and/or WAT.

In a second embodiment, the invention provides an animal model for metabolic disorders including, but not limited to, eating disorders, body weight disorders, cachexia, anorexia, sarcopenia and wasting syndrome or disease. This embodiment includes the use of a non-human transgenic animal whose genome comprises a stably integrated transgenic nucleotide sequence encoding Lysine-specific Demethylase 1 (LSD1) operably linked to a promoter for studying metabolism and/or as an animal model for metabolic disorders. The animals in accordance with this embodiment have an increased amount of LSD1 in at least one tissue. These animals typically overexpress LSD1 in at least one tissue. The overexpression may or may not affect all tissues of the animal. Preferably, the amount of LSD1 protein or Lsd1 mRNA is increased in fat tissue, e.g. in BAT and/or WAT.

In both embodiments, the reduced expression and the increased expression (overexpression), respectively, is relative to a control animal. The control animal may be a wild type animal which is substantially identical to the modified animal or transgenic animal, except for the genetic manipulation. The amount of LSD1 may be determined at the protein level, e.g. by immunoassays using antibodies against LSD1. The expression level of Lsd1 may be determined by quantitative RT-PCR, detecting the amount of Lsd1 mRNA.

In the first embodiment, the amount of LSD1 protein, or the amount of Lsd1 mRNA may be reduced relative to the control animal by at least 10%, preferably by at least 20%, more preferably by at least 30%, more preferably by at least 40%, e.g. by about 50%. For example, the amount of LSD1 protein, or the amount of Lsd1 mRNA may be reduced relative to the control animal by 10% to 90%, preferably by 20% to 80%, more preferably by 30% to 70%, more preferably by 40% to 60%.

In the animals of the first embodiment the protein and/or mRNA levels of Prdm16, Pgc-1α and Ucp1 are reduced, e.g. by at least 10%, more preferably by at least 25%, most preferably by at least about 50%, relative to a control animal. Body fat mass in these animals may be increased by about 10% relative to a control animal, in particular after high fat diet. Blood glucose levels in these animal may be increased by about 10% to about 50%, or by about 20% to about 40%, relative to a control animal. Moreover, the animals of the first embodiment typically exhibit reduced insulin sensitivity and glucose uptake relative to a control animal, wherein insulin sensitivity and glucose uptake may be determined according to the tests described in the Examples hereinbelow.

In the second embodiment, the amount of LSD1 protein, or the amount of Lsd1 mRNA may be increased relative to the control animal by at least 10%, preferably by at least 25%, more preferably by at least 50%, more preferably by at least 75%, e.g. by about 100%. For example, the amount of LSD1 protein, or the amount of Lsd1 mRNA may be increased relative to the control animal by 10% to 1000%, preferably by 25% to 500%, more preferably by 50% to 200%, more preferably by 75% to 150%. In this embodiment the phrase "LSD1 protein" includes endogenous and exogenous LSD1 protein. The phrase "Lsd1 mRNA" includes endogenous and exogenous Lsd1 mRNA.

The transgenic non-human animal may be a transgenic non-human vertebrate animal, preferably a mammal, preferably a rodent, such as a mouse. Suitable animals are available, or easily generated, using conventional methods, in a variety of genera, including rodents (e.g., rats), rabbits, guinea pigs, dogs, goats, sheep, cows, horses, pigs, llamas, camels or the like. Preferably, the non-human transgenic animal is a transgenic mouse.

The animal from which the progeny animal is descended is referred to as "progenitor animal". "Progeny" of a progenitor mammal are any animals which are descended from the progenitor as a result of sexual reproduction or cloning of the progenitor, and which have inherited genetic material from the progenitor. In this context, cloning refers to production of genetically identical offspring from DNA or a cell(s) of the progenitor animal. As used herein, "development of an animal" from a cell or cells (embryonic cells, for example), or development of a cell or cells into an animal, refers to the developmental process that includes growth, division and differentiation of a fertilized egg or embryonic cells (and their progeny) to form an embryo, and birth and development of that embryonic animal into an adult animal.

An animal is "derived from" a transgenic ovum, sperm cell, embryo or other cell if the transgenic ovum, sperm cell, embryo or other cell contributes DNA to the animal's genomic DNA. For example, a transgenic embryo of the invention can develop into a transgenic animal of the invention. A transgenic ovum of the invention can be fertilized to create a transgenic embryo of the invention that develops into a transgenic animal of the invention. A transgenic sperm of the invention can be used to fertilize an ovum to create a transgenic embryo of the invention that develops into a transgenic animal of the invention. A transgenic cell of the invention can be used to clone a transgenic animal of the invention.

As used herein, a "transgenic non-human mammal" is a non-human mammal into which an exogenous recombinant construct has been introduced, or its progeny. Such a mammal may have developed from (a) embryonic cells into which the construct has been directly introduced or (b) progeny cells of (a). As used herein, an "exogenous construct" is a nucleic acid that is artificially introduced, or was originally artificially introduced, into an animal. The term "artificial introduction" excludes introduction of a construct into an animal through normal reproductive processes (such as by cross breeding). However, animals that have been produced by transfer of an exogenous construct through the breeding of a mammal comprising the construct (into whom the construct was originally "artificially introduced") are considered to "comprise the exogenous construct." Such animals are progeny of animals into which the exogenous construct has been introduced.

In accordance with the first embodiment, the transgenic non-human animal contains a disruption in an endogenous LSD1 gene such that at least one allele of the LSD1 gene is non-functional or does not express a functional LSD1, wherein the disruption is an insertion of a transgene into the endogenous LSD1 gene. The disruption can be, for example, an insertion, missense, frameshift, or deletion mutation. The disruption can also alter a promoter, enhancer, or splice site. The disruption can be insertion of a transgene. The transgene optionally encodes a selectable marker, such as, for example a LacZ reporter gene operably linked to a LSD1 promoter. The provided non-human animals are preferably heterozygous for LSD1. As used herein, the term heterozygous means that the animal has a disruption in one allele (i.e., endogenous gene) while the second allele is unaffected (i.e., does not contain a disruption). In a most preferred embodiment, the genome of the animal comprises a disruption of only one allele of the gene encoding LSD1. An example of this embodiment is the Lsd+/− mouse described in the Examples.

In accordance with the second embodiment, the invention relates to a non-human transgenic animal (e.g., a rodent, preferably a mouse) whose genome comprises a DNA sequence encoding hLSD1, or encoding a biologically active fragment or variant thereof, which is operably linked to an expression control sequence. Typically, the mouse according to this embodiment will overexpress LSD1 (see, for example, the LSD1-overexpressing mice described in the Examples). In this embodiment, the non-human transgenic animal of the invention is preferably one whose somatic and germ cells comprise at least one genomically integrated copy of a recombinant construct of the invention (a recombinant construct comprising a sequence encoding LSD, preferably hLSD1), or an active fragment or variant thereof, which sequence is operably linked to an expression control sequence. Alternatively, the disclosed transgene construct can also be assembled as an artificial chromosome, which does not integrate into the genome but which is maintained and inherited substantially stably in the animal. Artificial chromosomes of more than 200 kb can be used for this purpose. The present invention is also directed to the creation of transgenic mice in whose tissue specific expression of the hLSD1 transgene is driven by a tissue specific promoter, as is discussed more extensively below.

The invention further provides a transgenic gamete, including a transgenic ovum or sperm cell, a transgenic embryo, and any other type of transgenic cell or cluster of cells, whether haploid, diploid, or of higher zygosity having at least one disruption in the LSD1 gene.

As used herein, the term "embryo" includes a fertilized ovum or egg (i.e., a zygote) as well as later multicellular developmental stages of the organism. The disruption referred to above is preferably in the animal's somatic and germ cells.

Also included herein are progeny of the transgenic animal that preferably comprise a disruption of at least one allele of the LSD1 gene, and transgenic animals derived from a transgenic ovum, sperm, embryo or other cell of the invention.

The transgenic animal may be sterile although, preferably, it is fertile. The present invention further includes a cell line derived from a transgenic embryo or other transgenic cell of the invention, which contains a disruption of at least one allele of the LSD1 gene. Methods of isolating such cells and propagating them are known to those of skill in the art.

Generation of Transgenic Animals

The transgenic non-human animals of the invention are produced by introducing transgenes into the germline of the non-human animal. Embryonal target cells at various developmental stages are used to introduce the transgenes of the invention. Different methods are used depending on the stage of development of the embryonal target cell(s). Such methods include, but are not limited to, microinjection of zygotes, viral integration, and transformation of embryonic stem cells as described below.

Microinjection of zygotes is the preferred method for incorporating transgenes into animal genomes. A zygote, which is a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1-2 picoliters of a solution containing transgenic DNA sequences. The use of a zygote for introduction of transgenes has the advantage that, in most cases, the injected transgenic DNA sequences will be incorporated into the host animal's genome before the first cell division. Brinster et al., Proc. Natl. Acad. Sci. USA 82:4438 (1985). As a consequence, all cells of the resultant transgenic animals (founder animals) stably carry an incorporated transgene at a particular genetic locus.

Viral integration can also be used to introduce the transgenes of the invention into an animal. The developing embryos are cultured in vitro to the blastocyte developmental stage. The blastomeres may be infected with appropriate retroviruses. Jaenich, Proc. Natl. Acad. Sci. USA 73:1260. Infection of the blastomeres is enhanced by enzymatic removal of the zona pellucida. Transgenes are introduced via viral vectors which are typically replication-defective but which remain competent for integration of viral-associated DNA sequences, including transgenic DNA sequences linked to such viral sequences, into the host animal's genome. Transfection is easily and efficiently obtained by culture of blastomeres on a monolayer of cells producing the transgene-containing viral vector. Alternatively, infection may be performed using cells at a later developmental stage, such as blastocoeles. In any event, most transgenic founder animals produced by viral integration will be mosaics for the transgenic allele; that is, the transgene is incorporated into only a subset of all the cells that form the transgenic founder animals. Moreover, multiple viral integration events may occur in a single founder animal, generating multiple transgenic alleles which will segregate in future generations of offspring. Introduction of transgenes into germline cells by this method is possible but probably occurs at a low frequency. However, once a transgene has been introduced into germline cells by this method, offspring may be produced in which the transgenic allele is present in all of the animal's cells, i.e., in both somatic and germline cells.

Embryonic stem (ES) cells can also serve as target cells for introduction of the transgenes of the invention into animals. ES cells are obtained from pre-implantation embryos that are cultured in vitro. Evans et al., Nature 292:154 (1981). ES cells that have been transformed with a transgene can be combined with an animal blastocyst, after which the ES cells colonize the embryo and contribute to the germline of the resulting animal. Once a transgene has been introduced into germline cells by this method, offspring may be produced in which the transgenic allele is present in all of the animal's cells, i.e., in both somatic and germline cells.

The transgenic nucleic acid may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

In practicing the invention, animals of the transgenic maintenance line are crossed with animals having a genetic background in which expression of the transgene results in symptoms of obesity or obesity-related disorders. Offspring that have inherited the transgenic nucleic acids of the invention are distinguished from littermates that have not inherited transgenic nucleic acids by analysis of genetic material from the offspring for the presence of nucleic acid sequences derived from the transgenic nucleic acids of the invention. For example, biological fluids that contain polypeptides uniquely encoded by the transgenic nucleic acids of the invention may be immunoassayed for the presence of the polypeptides. A simpler and more reliable means of identifying transgenic offspring comprises obtaining a tissue sample from an extremity of an animal, such as, for example, a tail, and analyzing the sample for the presence of nucleic acid sequences corresponding to the DNA sequence of a unique portion or portions of the transgenic nucleic acids of the invention. The presence of such nucleic acid sequences may be determined by, e.g., hybridization ("Southern") analysis with DNA sequences corresponding to unique portions of the transgene, analysis of the products of PCR reactions using DNA sequences in a sample as substrates, oligonucleotides derived from the transgene's DNA sequence, and the like.

Targeting Vectors

As used herein, the term "polynucleotide" is interchangeable with "nucleic acid." A polynucleotide of the present invention may be recombinant, natural, or synthetic or semi-synthetic, or any combination thereof. Polynucleotides of the invention may be RNA, PNA, LNA, or DNA, or combinations thereof. As used herein, the terms peptide, polypeptide and protein are also interchangeable.

A "recombinant construct" (also referred to herein as a "construct" for short) or a "transgene" of "transgenic nucleic acid" which is used to generate a transgenic animal of the second embodiment of the invention is a polynucleotide which comprises a sequence encoding LSD1 (preferably hLSD1), or an active fragment or variant thereof, which is operably linked to an expression control sequence. The coding sequence comprises LSD1 exon sequences, although it may optionally include intron sequences which are either derived from an hLSD1 genomic DNA or DNA of an unrelated chromosomal gene. The recombinant construct may comprise a sequence encoding mLSD1 or at least a biologically active fragment thereof. Preferably, the recombinant construct comprises a sequence encoding human LSD1 (hLSD1) or a biologically active fragment thereof. The amino acid sequences of hLSD1 and mLSD1 are shown in SEQ ID NO:3 and 5, respectively. The nucleotide sequence encoding mLSD1 is shown in SEQ ID NO:4. The nucleotide sequence encoding hLSD1 is shown in SEQ ID NO:1. The hLSD1 cDNA sequence including 5'- and 3'-untranslated regions is shown in SEQ ID NO:2. The nucleotide sequence of an exemplary recombinant construct is shown in SEQ ID NO:6. The amino acid sequence encoded by this construct is shown in SEQ ID NO:7.

For tissue-specific expression of the transgene in the transgenic animal, the coding sequence must be operably linked to an expression control sequence that drives expression specifically in that tissue. Suitable tissue-specific expression control sequences include the following: MMTV-LTR (for mammary-specific expression), etc.

Inducible/Repressible Expression Control Systems

An inducible promoter is one which, in response to the presence of an inducer, is activated. Hence, a coding sequence driven by an inducible promoter can be turned on or off by providing or withdrawing the inducer. A promoter may be homologous, derived from the same species as the coding sequence. Preferably, the promoter is heterologous, that is, derived from another species, or even from a virus. hLSD1 constructs in accordance with the present invention may be operably linked to an inducible or repressible control elements. An repressible system, described by Gossen, M. et al., Proc Natl Acad Sci USA 89:5547-51 (1992), is based on the use of control elements of the tetracycline-resistance operon encoded in Tn10 of *E. coli*. The tet repressor is fused with the activating domain of Herpes simplex virus VP16 to generate a tetracycline-controlled transactivator. Such a transactivator is used to stimulate transcription from a promoter sequence, such as the CMV promoter IE.

A gene controlled by a promoter acting under the influence of the tetracycline-controlled transactivator can be constitutively expressed and turned off by using an effective concentration of tetracycline. Such a system can regulate a gene over about five orders of magnitude. The tetracycline-repressible system functions in vivo in mice, where tetracycline administration via the diet is used to keep the expression of the inducible gene off. Tetracycline analogs which cross the blood-brain barrier can be used if gene activity is desired in the brain.

Two steps of transfection may be used to produce the appropriate system. A first transfection is used to isolate clones expressing the transactivator. The best clones are identified by testing each in a transient transfection assay for the ability to express a marker gene, such as an estrogen-dependent luciferase. The second transfection involves the hLSD1 coding sequence under control of an inducible promoter into a transactivator-containing clone. One strategy involves first isolating a stable cell line expressing the inducible hLSD1 protein or peptide by cotransfection of both plasmids into appropriate target cells. After selection, for example with G418, clones showing estrogen-dependent expression of hLSD1 may be detected by an immunoassay or biological assay. To increase the rate of plasmid integration and to stabilize the integrated plasmids in the host genome, the plasmids are preferably linearized and cotransfected into cells in the presence of mammalian high molecular weight DNA as a carrier.

The relative advantages of a two vector system, as described above, over a single vector system involving a larger plasmid is that in a two vector system, multiple copies of the reporter plasmid (encoding the gene of interest) may be needed to obtain a detectable biological effect in a cell, while one or only a few copies of the transactivator-carrying plasmid may suffice.

According to the present invention, the hLSD1 DNA molecule is placed under the control of a promoter subject to regulation by a tetracycline-controlled transactivator. Such a construct (in a single vector or preferably two vector form) is delivered into target cells, whether embryonic, adult normal or tumor, either in vitro or in vivo. To express the hLSD1, tetracycline is withheld so that the hLSD1 DNA is expressed. To prevent the action of the hLSD1, for example, locally, tetracycline or an active congener of tetracycline is administered locally to the cells transfected with the constructs. Effective systemic doses (oral or parenteral) of tetracycline are in the range of about 0.1 mg to 1 g per day. In a preferred embodiment, the transactivator is maintained in the "on" position by withholding tetracycline.

An estrogen-inducible system described by Braselmann, S. et al. Proc Natl Acad Sci USA (1993) 90:1657-61, is based on the fact that most mammalian cells neither express any Gal4-like activity nor endogenous estrogen receptor (ER), thus rendering estrogen an inert signal for them. The authors developed a selective induction system based on the estrogen-regulatable transcription factor Gal-ER. Gal-ER consists of the DNA-binding domain of the yeast Gal4 protein fused to the hormone-binding domain of the human ER and hence exclusively regulates a transfected coding sequence under the control of a Gal4-responsive promoter in mammalian cells. This system includes a synthetic Gal4-responsive promoter which consists of four Gal4-binding sites, an inverted CCAAT element, a TATA box, and the adenovirus major late initiation region. This promoter shows extremely low basal activity in the absence of, and high inducibility in the presence of, ligand-activated Gal-ER. The transcription factor Gal-ER is rendered more potent and less susceptible to cell type-specific variation by fusing the strong activating domain of the herpesvirus protein VP16 onto its C-terminus. In response to estrogen, e.g., 17-β estradiol, Gal-ER-VP16 may induce the Gal4-responsive promoter at least 100-fold in transfected cells. Thus, the Gal-ER induction system is a powerful genetic switch for regulating heterologous genes. For induction of expression of the DNA molecules of the present invention in an estrogen inducible system in an animal, local or systemic treatment with estrogen would be required. An effective dose of an estrogen is a dose which would trigger the expression of an hLSD1-encoding nucleic acid of the present invention to produce hLSD1 and promote growth of hLSD1-expressing adipose cells. Such doses can be ascertained by one skilled in the art. Preferably, doses in the range of about 0.05 to 100 mg/kg of an estrogen are used in a single dose or in multiple doses over a period of about one week days to about 6 months, or even longer. Forms and preparations of estrogen and their usage in animals, particularly in humans, are well-known in the art. Estrogen analogues which are capable of specifically activating the exogenous transactivator while having fewer biological effects and side effects are preferred.

Ionizing radiation has been used to activate the transcription of exogenous genes, for example, encoding a cytotoxic protein TNF-I (Weichselbaum, R R et al., Int J Radiation Oncology Biol Phys 24:565-67 (1992)) This may be accomplished through the use of radiation-responsive elements distal to the transcription start site of such genes. See, for example, Hallahan, D et al., Proc Natl Acad Sci USA 88:2152-20 (1991); Datta, R et al., Proc Natl Acad Sci USA 89:10149-53 (1992); Weichselbaum et al., supra; Hallahan, D E et al. J Biol Chem 268:4903-07 (1993); Weichselbaum, R R et al., Intl J Radiation Oncology Bio. Phys 30:229-34 (1994); Hallahan, D E et al. Nature Med 1:786-91 (1995), which references are hereby incorporated by reference in their entirety. Thus, the present invention provides methods for the spatial and temporal control of gene expression with such radiation-inducible promoters to activate hLSD1. The hLSD1 coding sequence is placed in a vector under control of a radiation-inducible promoter.

In a preferred embodiment, the expression control sequence (either a ubiquitously acting expression control sequence or a tissue-specific one) is expressed in a regulatable fashion, meaning that it is preferably a component of any of a number of well-known regulatable expression systems.

Methods of making recombinant constructs are conventional. Such methods, as well as many other molecular biological methods used in conjunction with the present invention, are discussed, e.g., in Sambrook, et al. (1989), Molecular Cloning, a Laboratory Manual, Cold Harbor Laboratory Press, Cold Spring Harbor, N.Y.; Ausubel et al. (1995). Current Protocols in Molecular Biology, N.Y., John Wiley & Sons; Davis et al. (1986), Basic Methods in Molecular Biology, Elsevier Sciences Publishing, Inc., New York; Hames et al. (1985), Nucleic Acid Hybridization, IL Press; Dracopoli et al. Current Protocols in Human Genetics, John Wiley & Sons, Inc.; and Coligan et al. Current Protocols in Protein Science, John Wiley & Sons, Inc. See, also, the Examples herein.

In a specific embodiment of this invention, the transgenic animal does not comprise additional transgenic sequences. This means that the transgenic construct present in the transgenic animal is the only transgenic construct present in the animal of this invention. The transgenic animal preferably does not comprise further genetic germ line modifications other than that described hereinabove. The genetic background of the transgenic animal of the invention is 'wild type' except for the genetic modifications described hereinabove. This embodiment is preferred, as it allows studying the effect of any methods interfering with the action of LSD1.

Method for Identifying Potential Therapeutic Agents

Another aspect of this invention is a method for identifying a compound which inhibits the growth of adipose tissue, comprising (a) administering a test compound to a transgenic animal according to the present invention and (b) determining the effect of the test compound on the growth or survival of the adipocytes or adipose tissue in said transgenic animal, thereby identifying a compound that inhibits the growth of adipose tissue.

Another aspect of this invention is a method for identifying a compound which is useful in the treatment of type 2 diabetes, obesity and/or a related disorder, comprising (a) administering a test compound to a transgenic animal according to the first embodiment of the present invention and (b) determining the effect of the test compound on at least one metabolic parameter, at least one obesity-related parameter or at least one diabetes-related parameter, and optionally (c) selecting the compound if the effect is indicative of inhibition or amelioration of type 2 diabetes, obesity and/or a related disorder.

The methods may comprise the steps (i) administering a test compound to a transgenic animal according to the present invention, (ii) administering the same test compound to a control animal, and (iii) determining the effect of the test compound on the transgenic animal as compared to said control animal. The control animal is preferably an animal of the same species as the transgenic animal. The control animal does not show reduced or increased expression of LSD1 or only to a significantly lower degree, relative to a wild type animal. In one embodiment, the control animal does not carry the transgenic nucleotide sequence present in the test animal of step (i). In another embodiment, the control animal is also carrying the same transgenic nucleotide sequence as the transgenic animal used in step (i) but there is no or only a slight reduction or increase in expression. This can be achieved by the use of inducible transgene constructs, see supra.

The effect to be determined in step (iii) may be any change in any clinically or biologically relevant parameter including body weight, adipose tissue mass, adipose tissue size, presence of WAT markers, number of adipocytes, presence of lipomas, survival rate and the like (relative to the control animal). The methods of analysis include but are not limited to determining the body weight, adipose tissue mass, adipose tissue size, presence of WAT markers, number of adipocytes, presence of lipomas, survival rate and the like, e.g. by histological methods and/or biochemical methods. A particularly preferred parameter is insulin sensitivity and glucose tolerance.

The test compound may be selected as a compound which is useful in the treatment of type 2 diabetes, obesity or a related disorder if there is a significant difference in at least one of the clinically or biologically relevant parameters tested, for example when the parameter (e.g. adipose tissue mass, adipose tissue size, presence of WAT markers, number of adipocytes, presence of lipomas, survival rate etc.) in the transgenic test animal used in step (i) is significantly reduced (e.g. by at least 10%, preferably by at least 25%, more preferably by at least 50%) relative to that of the control animal.

The test compound may be selected as a compound which is useful in the treatment of type 2 diabetes, obesity or a related disorder if blood glucose levels are reduced by the test compound, or if insulin sensitivity and/or glucose uptake are significantly increased.

The compound may be selected if any one the the target genes of LSD1 (e.g. Nrf1, Prdm16 and Pgc-1α) is upregulated by the test compound, e.g. by at least about 10% or at least about 25%, or at least about 50%, or at least about 100%. The quantitation is preferably done via RT-PCR.

In another embodiment, the compound may be selected if any one the the target genes of LSD1 (e.g. Nrf1, Prdm16 and Pgc-1α) is downregulated by the test compound, e.g. by at least about 10% or at least about 25%, or at least about 50%. The quantitation is preferably done via RT-PCR.

The compounds used as test compounds may be modulators of the LSD1 gene, of the LSD1 protein, or of any target gene of LSD1. Modulators include activators and inhibitors. The modulators are preferably activators of the LSD1 protein or activators of the LSD1 gene (see infra).

The invention further pertains to a method for identifying a compound which inhibits adipose cell or tissue growth, the method comprising
  providing a cell expressing LSD1
  contacting the cell with a test compound
  determining the amount of LSD1 protein or LSD1 mRNA expressed by the cell
  selecting the test compound as a compound which inhibits adipose cell or tissue growth if the amount of LSD1 protein or LSD1 mRNA expressed by the cell is greater than that expressed by a control cell.

The invention further relates to a LSD1 modulator for use in the treatment and/or prevention of type 2 diabetes, obesity or an obesity-related disorder. The invention further relates to a method of treating type 2 diabetes, obesity or an obesity-related disorder, comprising administering to an individual in need thereof, a pharmaceutically effective amount of a LSD1 modulator. Obesity-related disorders include, but are not limited to, insulin resistance, hypertension, hyperuricemia, fatty liver, non-alcoholic fatty liver disease, polycystic ovarian syndrome, acanthosis nigricans, hyperphagia, endocrine abnormalities, triglyceride storage disease, Bardet-Biedl syndrome, and Lawrence-Moon syndrome. Preferably, the disorder is type II diabetes. In certain embodiments, the obesity-related disorder is not hypertension.

LSD1 Modulators

An LSD1 activator to be used in accordance with this invention is a compound capable of increasing the amount of LSD1 mRNA or LSD1 protein in a cell and/or activating at least one function or activity of the LSD1 gene or the LSD1 protein. These functions include (1) the ability of LSD1 to interact with androgen receptor, (2) the ability of LSD1 to assemble with other proteins, in particular transcription factors into protein complexes, and (3) the catalytic activity of LSD1. The protein complexes may be important for transcriptional activation.

An LSD1 inhibitor to be used in accordance with this invention is a compound capable of reducing the amount of LSD1 mRNA or LSD1 protein in a cell and/or inhibiting at least one function of the LSD1 gene or the LSD1 protein. These functions include (1) the ability of LSD1 to interact with androgen receptor, (2) the ability of LSD1 to assemble with other proteins, in particular transcription factors into protein complexes, and (3) the catalytic activity of LSD1. The protein complexes may be important for transcriptional activation.

The LSD1 modulator to be used in accordance with this invention may be a compound capable of activating or inhibiting expression of the LSD1 gene in a cell. Various methods for activating or inhibiting expression of genes in a cell are known to one of skill in the art (e.g. RNA interference or antisense technology).

In another embodiment the invention, the LSD1 modulator is capable of modulating the interaction of LSD1 protein with the androgen receptor. Such activators include "small molecules," also referred to herein as "compounds," which are isolated from natural sources or made synthetically. In general, such molecules may be identified from large libraries of natural products or synthetic (or semi-synthetic) extracts or chemical libraries according to methods known in the art. Those skilled in the field of drug discovery and development will understand that the precise source of test extracts or compounds is not critical to the methods of the invention. Accordingly, virtually any number of chemical extracts or compounds can be used in the methods described herein. The types of extracts or compounds that may be tested include plant, fungal, prokaryotic or eukaryotic cell or organism-based extracts, fermentation broths, and synthetic compounds including modifications of existing compounds. Numerous methods are also available for generating random or directed synthesis (e.g., semi-synthesis or total synthesis) of any number of chemical compounds, including, but not limited to, saccharides, lipids, peptides, polypeptides and nucleic acids and derivatives thereof. Synthetic compound libraries are commercially available.

In yet another embodiment, the LSD1 modulator may modulate (promote or inhibit) the stability the the LSD1 protein or Lsd1 mRNA.

In yet another embodiment, the LSD1 modulator may modulate (promote or inhibit) degradation of LSD1 protein or Lsd1 mRNA. For example, the pathways leading to degradation of LSD1 protein or Lsd1 mRNA in the cells may be inhibited, thus leading to an increased amount of LSD1 protein or Lsd1 mRNA in the cells.

In yet another embodiment, the LSD1 modulator may modulate (promote or inhibit) the translation efficiency of the Lsd1 gene.

Alternatively, libraries of natural compounds in the form of bacterial, fungal, plant, and animal extracts are commercially available from a number of sources. In addition, natural and synthetically produced libraries can be generated according to methods known in the art, e.g., by standard extraction and fractionation methods. Furthermore any library or compound may readily be modified using standard chemical, physical, or biochemical methods.

Another class of agents that can be screened are antibodies, in particular monoclonal antibodies.

The LSD1 activators are preferably useful in the treatment and/or prevention of type 2 diabetes, obesity and/or related disorders. LSD1 inhibitors may be useful in the treatment and/or prevention of metabolic disorders such as eating disorders, body weight disorders, cachexia, anorexia, sarcopenia and wasting syndrome or disease.

"Cachexia" refers to a state of general ill health and malnutrition. It is often associated with and induced by malignant cancer, and is characterized by loss of appetite, lass of body mass, especially lean body mass, and muscle wasting.

"Anorexia" refers simply to a loss of appetite, whether brought on by medical or psychological factors. Anorexia is often closely associated with, and generally contributes to, the cachexia seen in patients with advanced cancers.

Modulators of Target Genes of LSD1

Target genes of LSD1 include, but are not limited to, Nrf1, Prdm16 and Pgc-1α.

In one embodiment, the modulator of a target gene of LSD1 is an activator of the target gene.

In another embodiment, the modulator of a target gene of LSD1 is an inhibitor of the target gene.

In another embodiment, the modulator of a target gene of LSD1 is an activator of Nrf1.

In another embodiment, the modulator of a target gene of LSD1 is an activator of Prdm16.

In another embodiment, the modulator of a target gene of LSD1 is an activator of Pgc-1α.

In another embodiment, the modulator of a target gene of LSD1 is an inhibitor of Nrf1.

In another embodiment, the modulator of a target gene of LSD1 is an inhibitor of Prdm16. In another embodiment, the modulator of a target gene of LSD1 is an inhibitor of Pgc-1α.

Preferably, an activator is capable of increasing the expression of the target gene, or activating a function of the gene product of said target gene. Typically, an inhibitor is capable of inhibiting the expression of the target gene, or inhibiting a function of the gene product of said target gene.

The above-mentioned modulators are useful in the treatment and/or prevention of type 2 diabetes, obesity and/or related disorders. The above-mentioned modulators may further be useful in the treatment and/or prevention of a metabolic disorder.

One of skill in the art will appreciate that the LSD1 modulators can be used alone or in combination with other compounds and therapeutic regimens to inhibit obesity or obesity-related disorders or obesity-related symptoms, or metabolic disorders.

An effective amount of the activator will be determined by the existence, nature, and extent of any adverse side-effects that accompany the administration of the composition; the $LD_{50}$ of the composition; and the side-effects of the composition at various concentrations. Typically, the amount of the composition administered will range from about 0.01 to about 20 mg per kg, more typically about 0.05 to about 15 mg per kg, even more typically about 0.1 to about 10 mg per kg body weight.

The activator can be administered, for example, by intravenous infusion, orally, intraperitoneally, or subcutaneously. Oral administration is the preferred method of administration. The formulations of compounds can be presented in unit-dose or multi-dose sealed containers, such as ampoules and vials.

The LSD1 activators are typically formulated with a pharmaceutically acceptable carrier before administration to an individual or subject. Pharmaceutically acceptable carriers are determined, in part, by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

Figure 5:
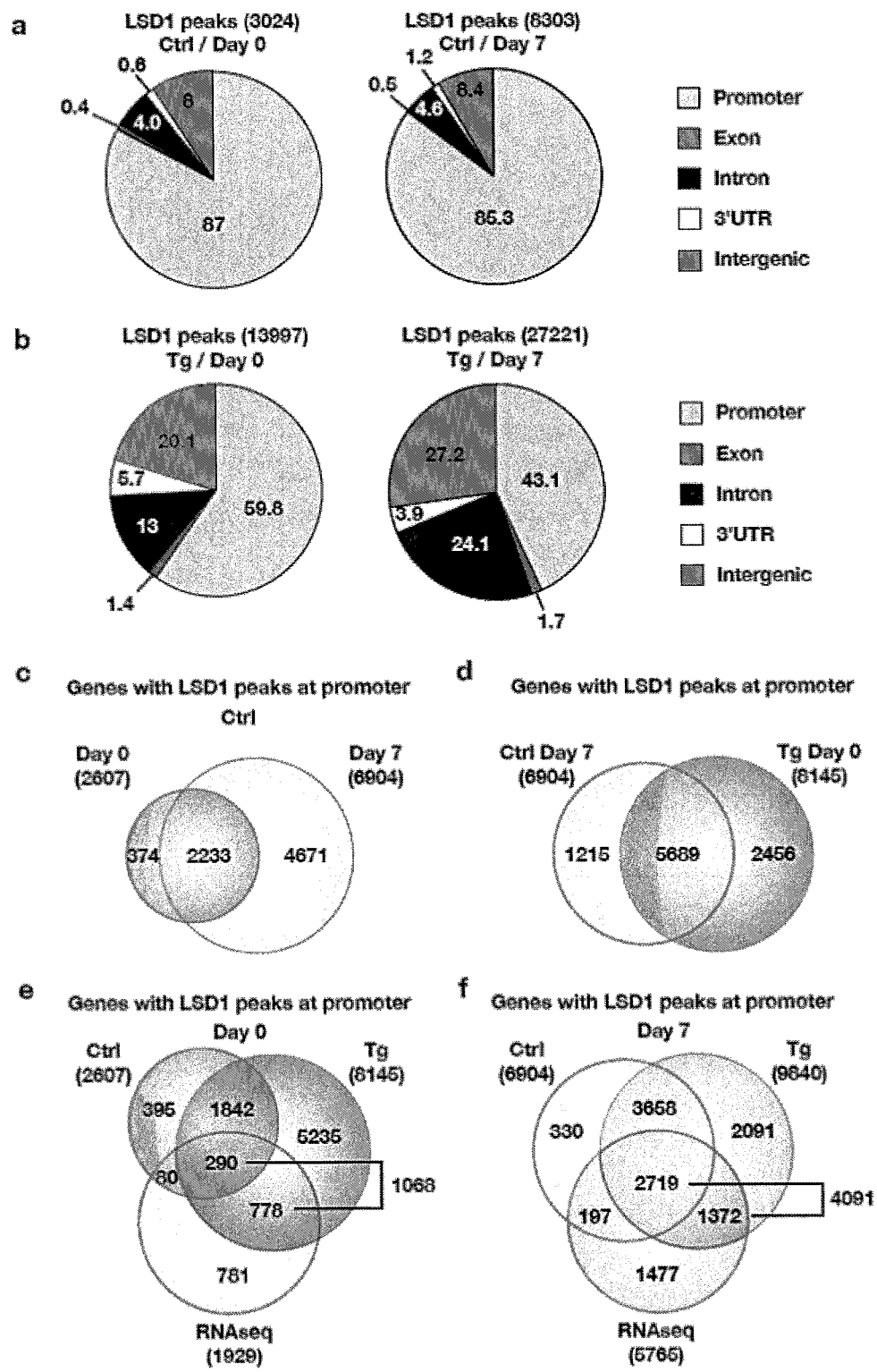

FIG. 5. LSD1 positively regulates multiple metabolic pathways to promote beige fat formation. a, b, Pie charts displaying genomic distribution of LSD1 peaks in (a) control (Ctrl) and (b) LSD1 overexpressing (Tg) 3T3-L1 cells determined by ChIP-seq analysis. c, d, Venn diagram showing the number of genes with LSD1 peaks at promoters in (c) 3T3-L1(Ctrl) cells at days 0 and 7 of differentiation, and (d) in 3T3-L1(Ctrl) cells at day 7 and 3T3-L1(Tg) cells at day 0 of differentiation. e, f, Venn diagram showing the number of genes with LSD1 peaks at promoters and differentially regulated genes deduced from RNA-seq data in 3T3-L1 (Ctrl) and 3T3-L1(Tg) cells at (e) day 0 and (f) day 7 of differentiation.

Figure 6:
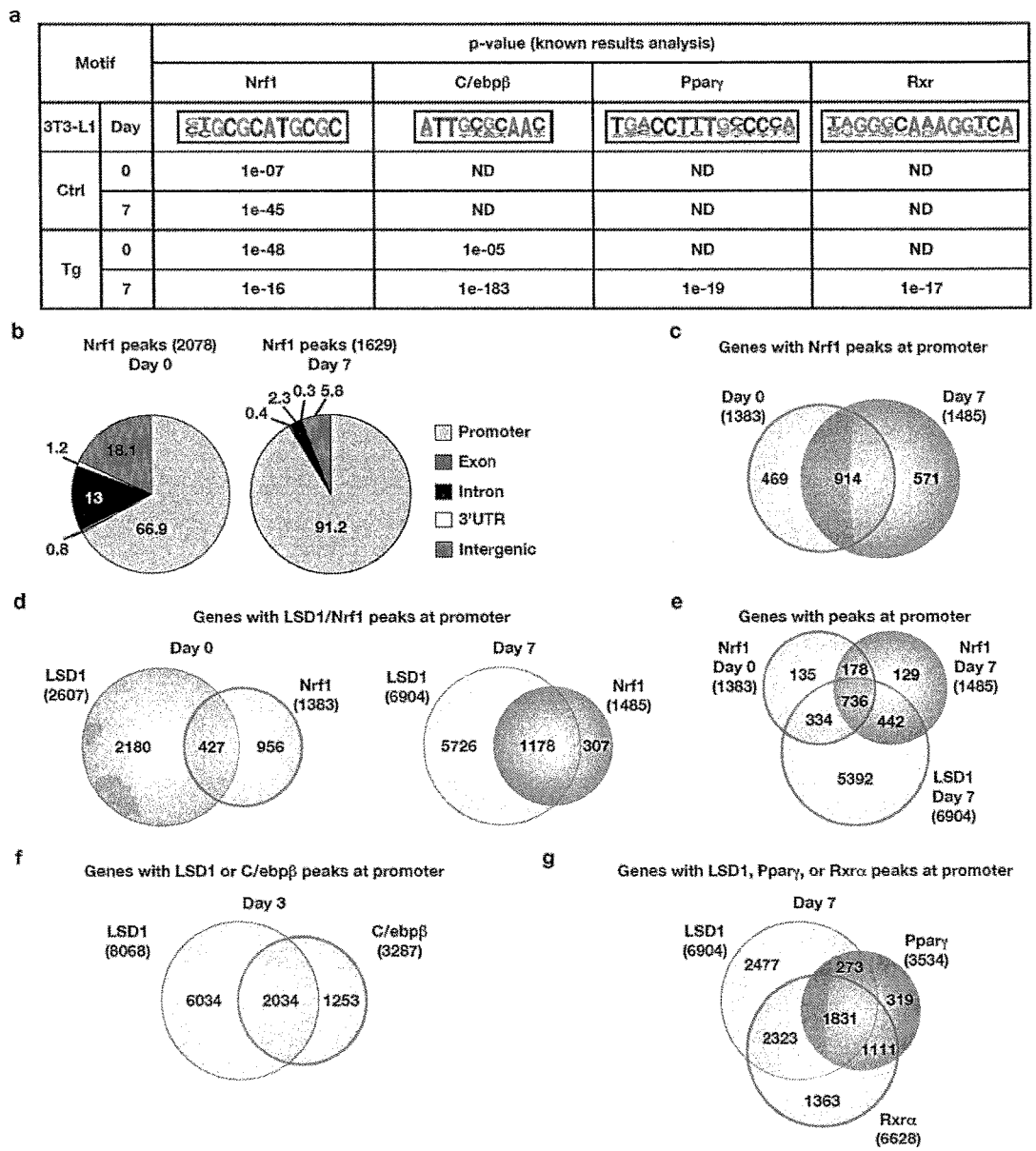

FIG. 6. LSD1 controls beige fat formation through Nrf1, C/ebpβ and Pparγ/Rxrα. a, HOMER motif analyses of LSD1 ChIP-seq data unravel Nrf1, C/ebpβ, Pparγ, and Rxr binding sites among the top scoring motifs. ND: motif not determined by HOMER. b, Pie charts displaying genomic distribution of Nrf1 peaks in 3T3-L1 cells at days 0 and 7. c, Venn diagram showing number and intersection of genes with Nrf1 promoter peaks in 3T3-L1 cells at days 0 and 7. d, e, Venn diagram depicting the number of genes with LSD1 and Nrf1 peaks at promoters in 3T3-L1 cells at days 0 and 7 of differentiation. f, g, Venn diagram depicting the number of genes with LSD1 and (f) C/ebpβ, or (g) Pparγ and Rxrα peaks at promoters in 3T3-L1 cells at days 3 and 7 of differentiation.

Figure 7:
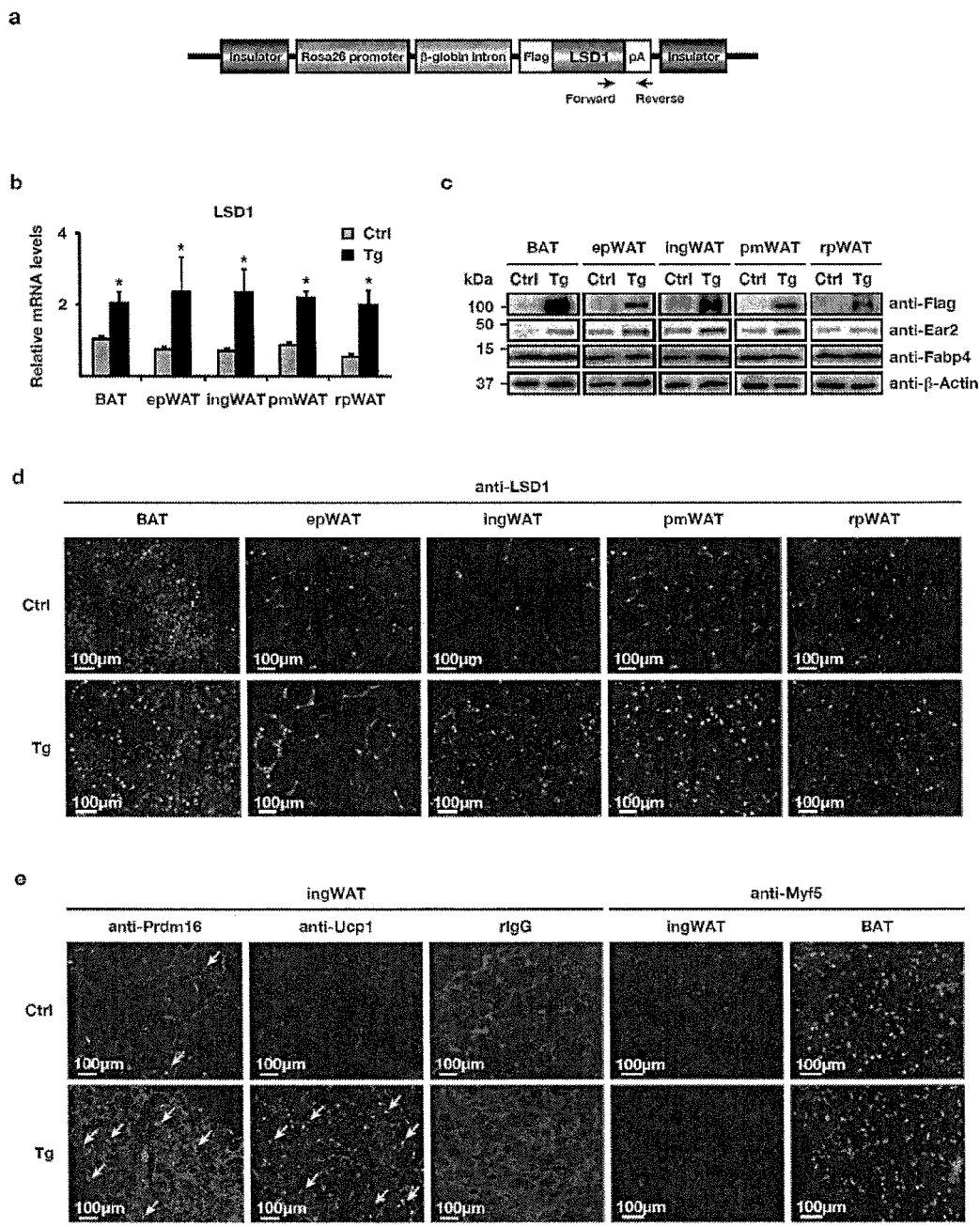

FIG. 7. Expression of LSD1 in transgenic mice promotes the formation of functional beige fat in white adipose tissue. a, Schematic representation of the Rosa26-LSD1 transgene. Arrows indicate the location of primers used to characterize the LSD1 allele. b, QRT-PCR analyses of total LSD1 (human and mouse) levels in interscapular brown adipose tissue (BAT), epididymal (epWAT), inguinal (ingWAT), perimuscular (pmWAT), and retroperitoneal (rpWAT) white adipose tissue of control (Ctrl) and transgenic (Tg) mice. c, Western blot analyses of Ear2 and Fabp4 in the indicated adipose tissues of Ctrl and Tg mice. Flag antibody was used to detect expression of the LSD1 transgene. β-Actin served as a loading control. d, Immunofluorescence analysis of LSD1 (yellow) in the indicated adipose tissues of Ctrl and Tg mice. Rabbit IgG was used as a negative control. e, Immunofluorescence analysis of Prdm16 and Ucp1 (yellow arrows) in ingWAT and of Myf5 in ingWAT and BAT of Ctrl and Tg mice. Rabbit IgG was used as a negative control. n=10 mice. Standard deviation represents+SEM, *p<0.05.

Figure 8:
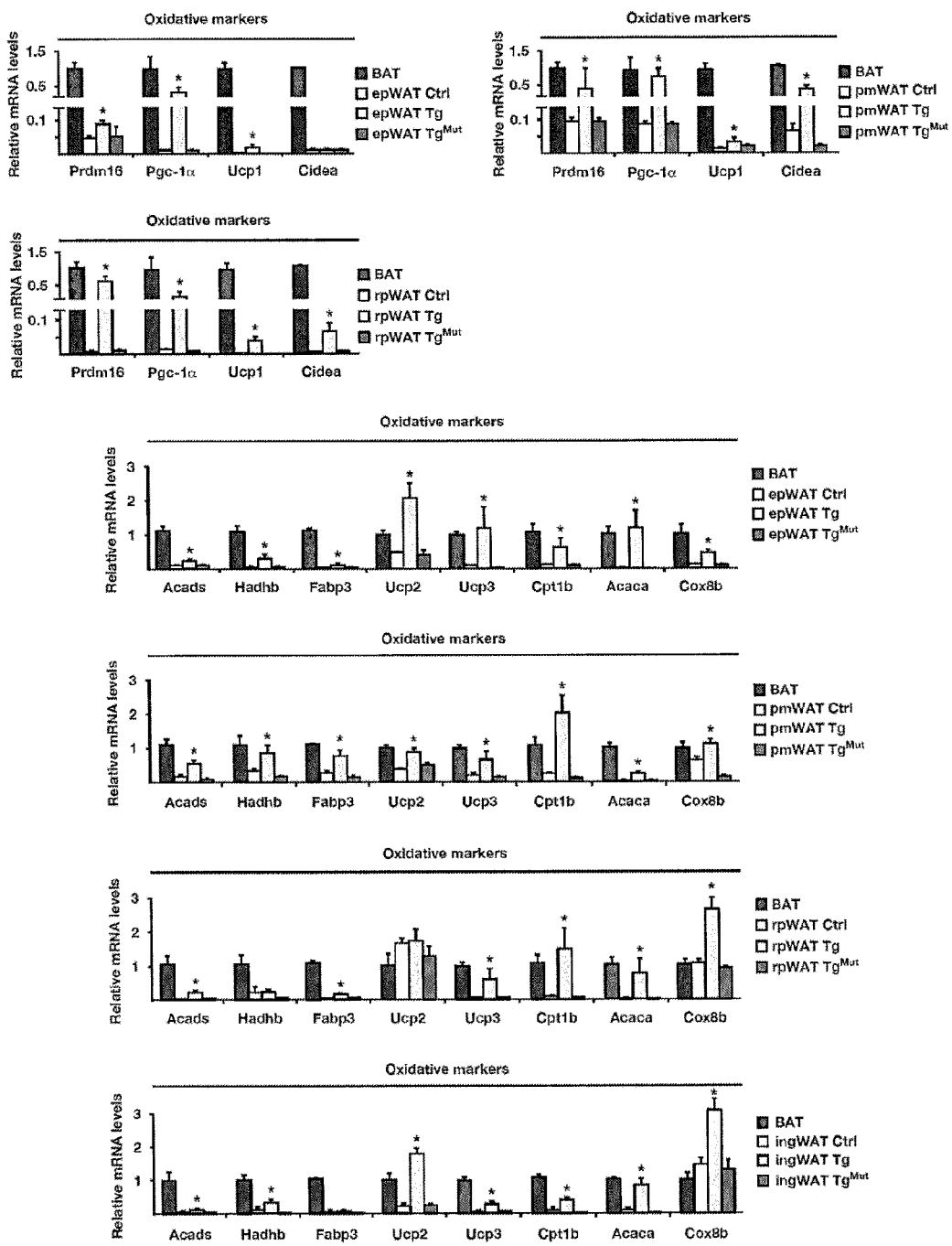

FIG. 8. Expression of LSD1 in transgenic mice promotes oxidative capacities in white adipose tissue. Relative transcript levels of oxidative markers in the indicated adipose tissues of control (Ctrl), transgenic (Tg), and transgenic mice expressing enzymatic inactive LSD1 (Tg$^{Mut}$). BAT of Ctrl mice was used as a control. n=10 mice. Standard deviation represents+SEM, *p<0.05 between Ctrl and Tg WAT.

Figure 9:
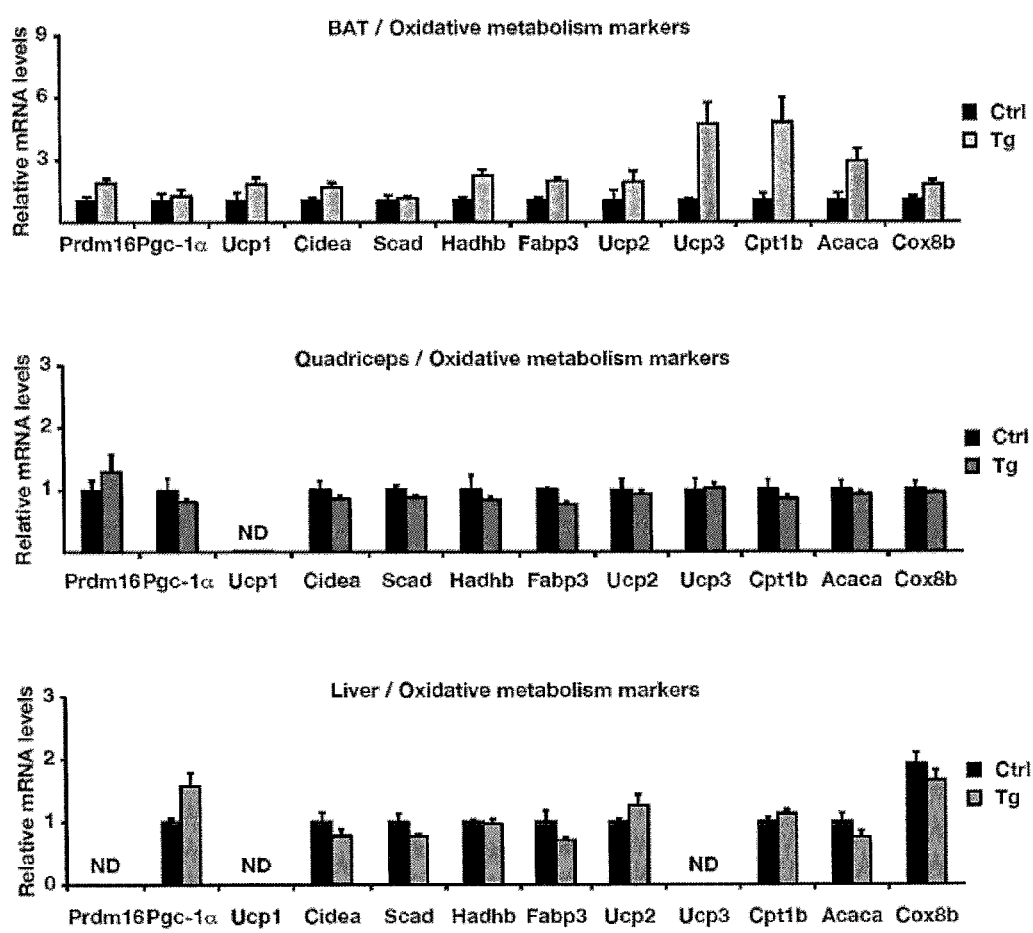

FIG. 9. Expression of LSD1 in transgenic mice does not promote oxidative capacities in brown adipose tissue, skeletal muscle, and liver. Relative transcript levels of oxidative markers in the indicated tissues of control (Ctrl) and transgenic (Tg) mice. n=10 mice. Standard deviation represents+SEM. ND: Not detected.

Figure 10:
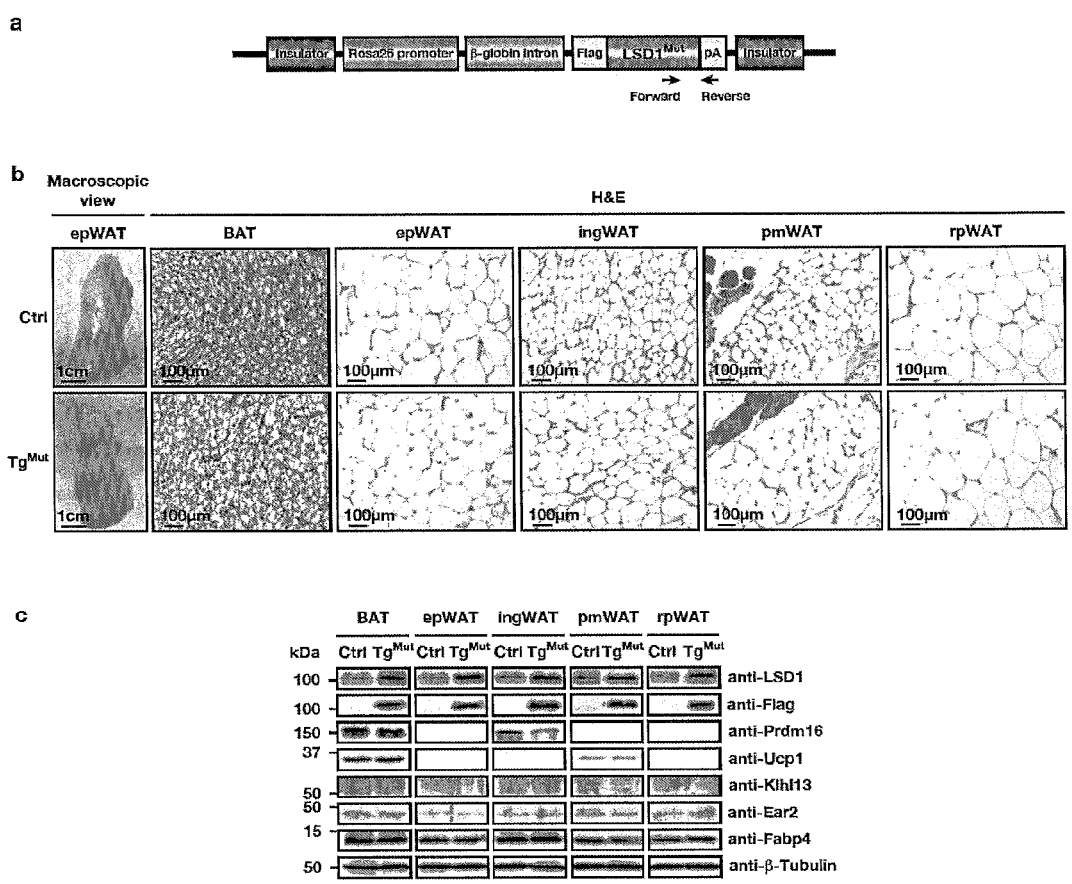

FIG. 10. Expression of enzymatic inactive LSD1 in transgenic mice does not promote the formation of functional beige fat in white adipose tissue. a, Schematic representation of the Rosa26-LSD1$^{Mut}$ transgene. Arrows indicate the location of primers used to characterize the LSD1$^{Mut}$ allele. b, Macroscopic view of epididymal fat and haematoxylin and eosin staining (H&E) of BAT, epWAT, ingWAT, pmWAT, and rpWAT of Ctrl and Tg$^{Mut}$ mice. c, Western blot analyses of LSD1, Prdm16, Ucp1, Klhl13, Ear2, and Fabp4 in the indicated adipose tissues of Ctrl and Tg$^{Mut}$ mice. Flag antibody was used to detect expression of the LSD1$^{Mut}$ transgene. β-Tubulin served as a loading control.

Figure 11:
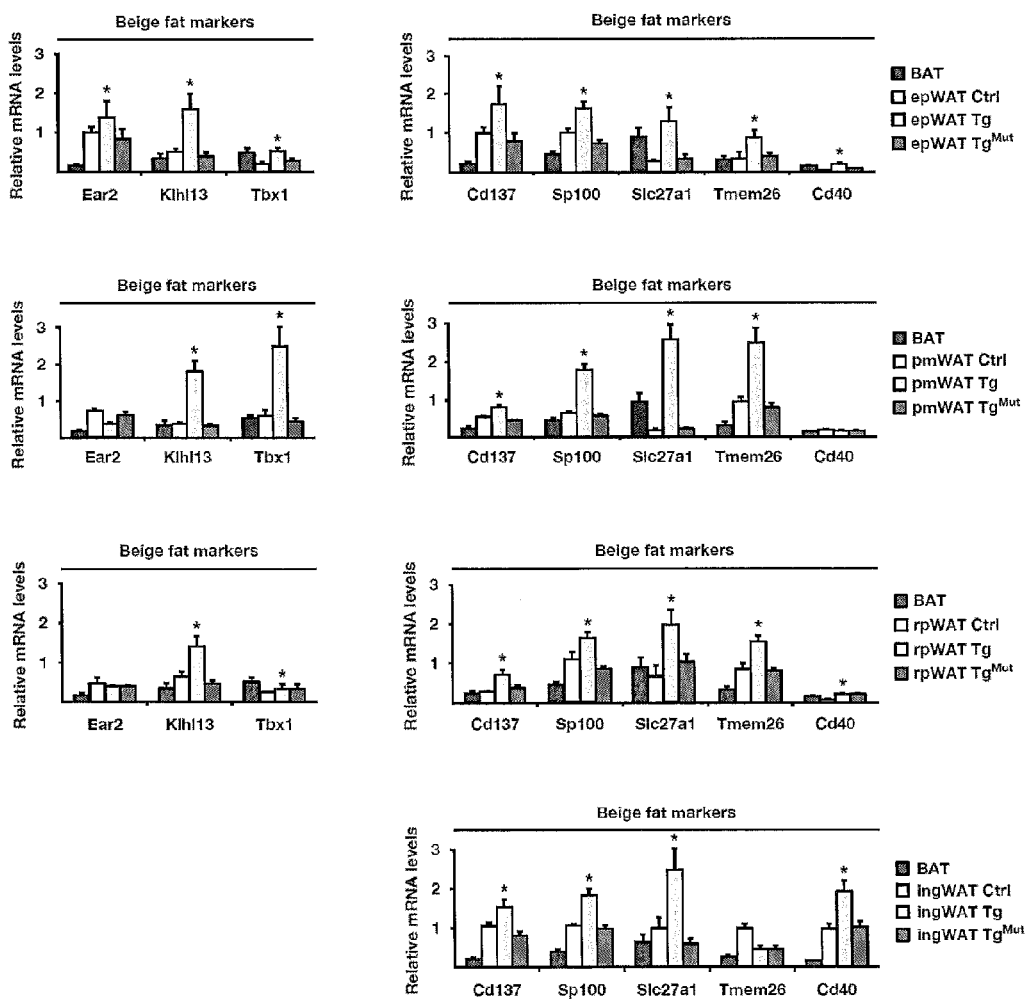

FIG. 11. Expression of LSD1 in transgenic mice promotes beige fat-selective markers in white adipose tissue. Relative transcript levels of beige fat-selective markers in the indicated adipose tissues of Ctrl, Tg, and Tg$^{Mut}$ mice. n=10 mice. Standard deviation represents+SEM, *p<0.05 between Ctrl and Tg WAT.

Figure 12:
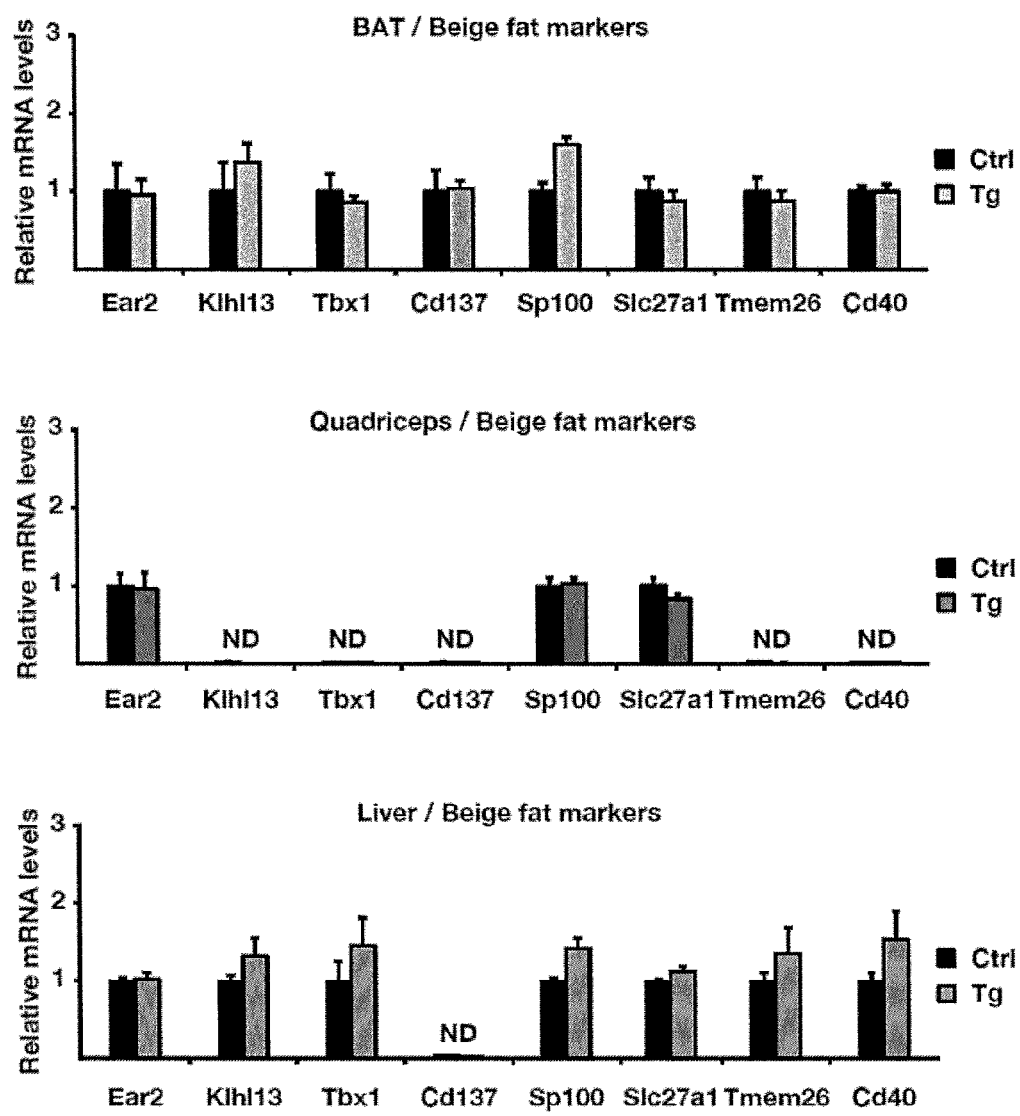

FIG. 12. Expression of LSD1 in transgenic mice does not foster the beige fat-selective gene programme in brown adipose tissue, skeletal muscle, and liver. Relative transcript levels of beige fat-selective markers in the indicated tissues of Ctrl and Tg mice. n=10 mice. Standard deviation represents+SEM. ND: Not detected.

Figure 13:
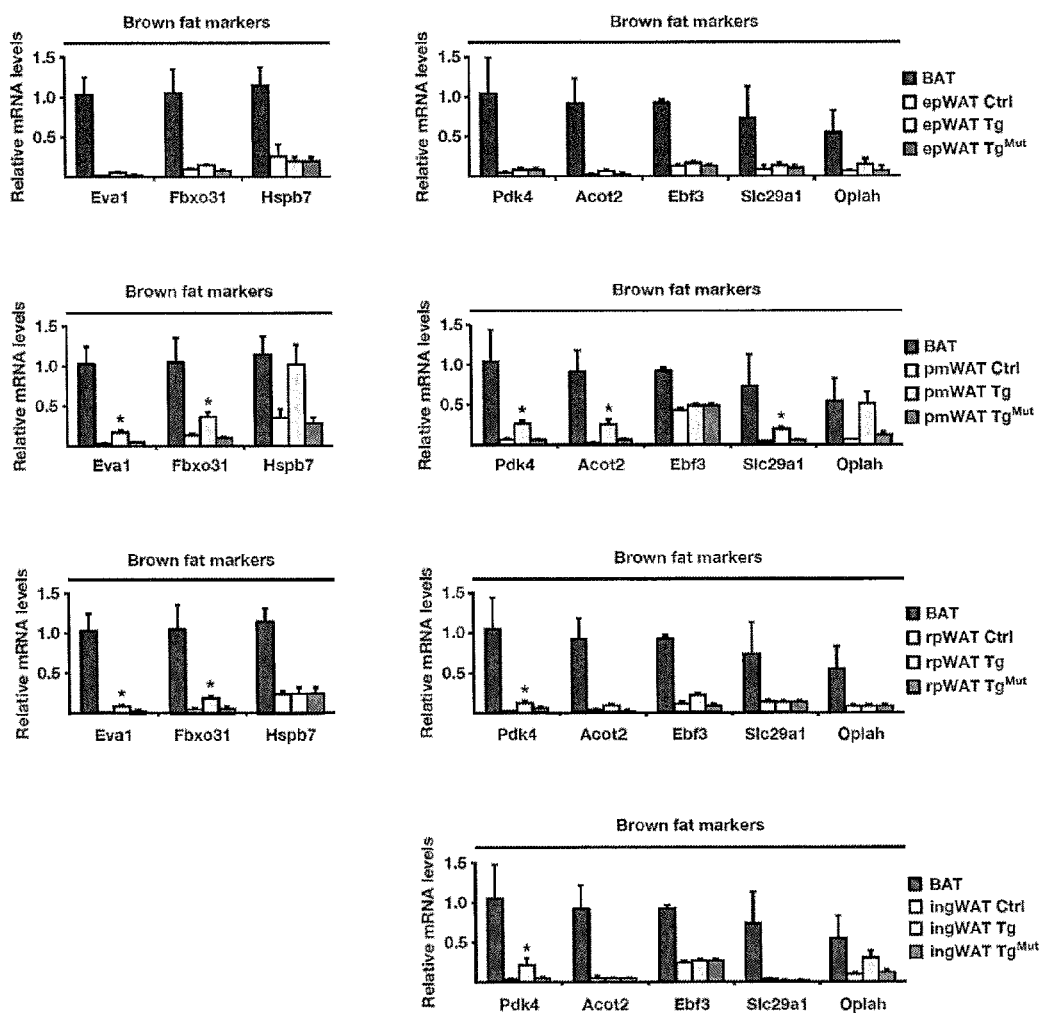

FIG. 13. Expression of LSD1 in transgenic mice does not promote brown fat-selective markers in white adipose tissue. Relative transcript levels of brown fat-selective markers in the indicated adipose tissues of Ctrl, Tg, and Tg$^{Mut}$ mice. BAT of Ctrl mice was used as a control. n=10 mice. Standard deviation represents+SEM, *p<0.05 between Ctrl and Tg WAT.

Figure 14:
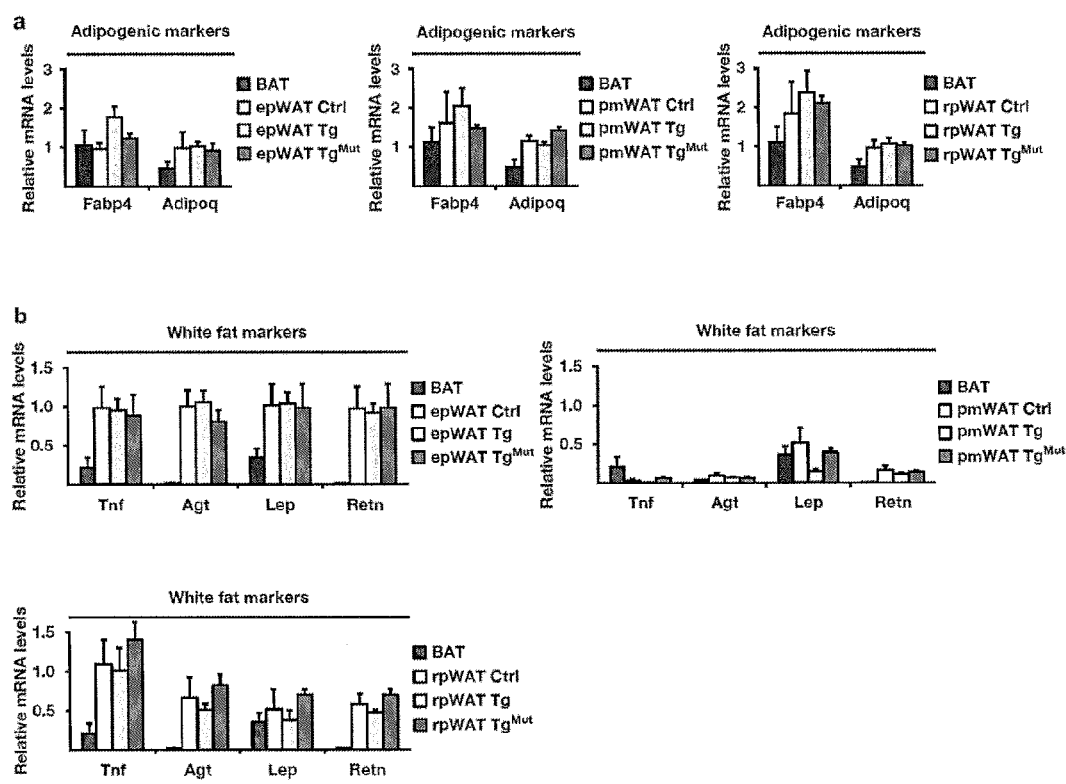

FIG. 14. Expression of LSD1 in transgenic mice does not alter white adipogenesis in white adipose tissue. a,b, Relative transcript levels of adipogenic (a), and white fat-selective (b) markers in the indicated adipose tissues of Ctrl, Tg, and Tg$^{Mut}$ mice. BAT of Ctrl mice was used as a control for adipogenic markers. n=10 mice. Standard deviation represents+SEM.

Figure 15:
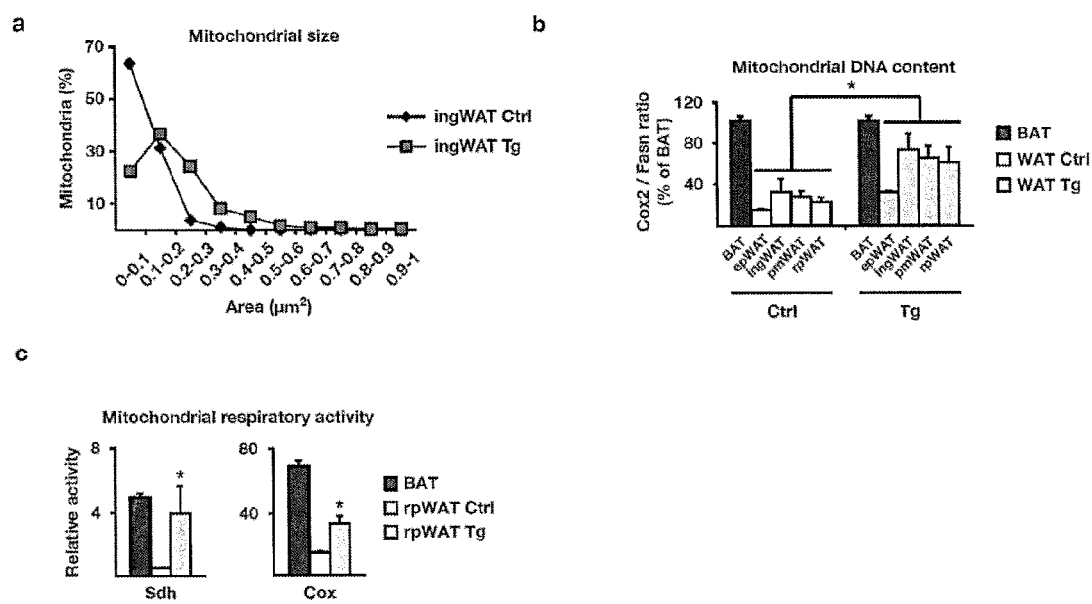

FIG. 15. Expression of LSD1 in transgenic mice promotes mitochondrial biogenesis in white adipose tissue. a, Distribution of mitochondria size determined from ultrastructure analysis. b, Ratio of mitochondrial to nuclear DNA content assessed by quantitative PCR of the mitochondrial-encoded Cox2 and the nuclear-encoded Fasn gene in the indicated adipose tissues of Ctrl and Tg mice. c, Determination of Sdh (mitochondrial respiratory chain complex II) and Cox (mitochondrial respiratory chain complex IV) activities in rpWAT of Ctrl and Tg mice. BAT of Ctrl mice was used as a positive control. n=5 mice. Standard deviation represents+SEM, *p<0.05.

Figure 16:
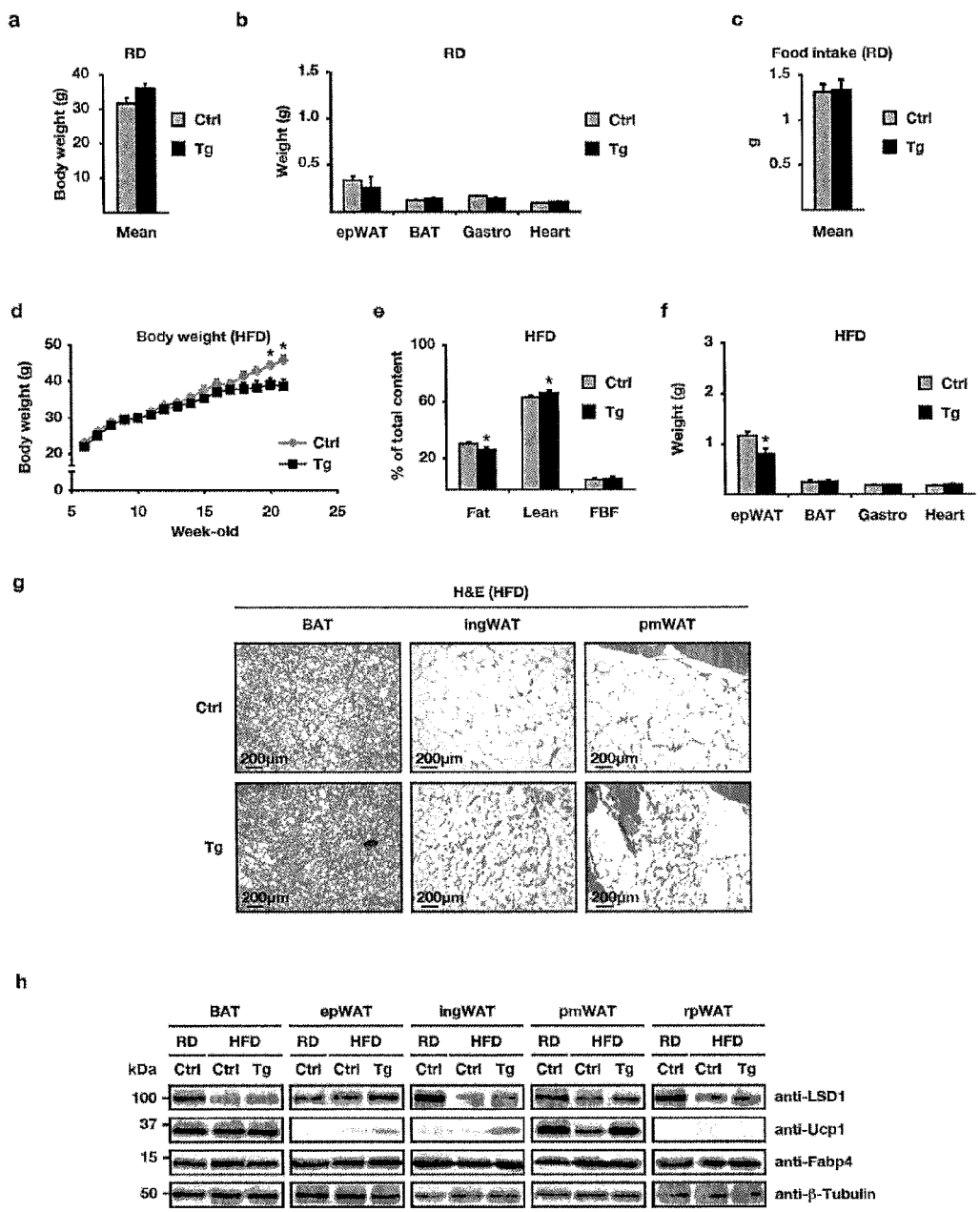

FIG. 16. LSD1 Tg mice display limited weight gain in response to a high-fat diet. a, Body weight of Ctrl and Tg mice fed a regular diet (RD). b, Weight of the indicated tissues of Ctrl and Tg mice fed a RD. c, Food consumption of Ctrl and Tg mice fed a RD. d, Body weight of Ctrl and Tg mice fed a high-fat diet (HFD). e, Fat, lean, and free body fluid (FBF) content of Ctrl and Tg mice fed a HFD. f, Weight of the indicated tissues of Ctrl and Tg mice fed a HFD. g, H&E staining of indicated adipose tissues of Ctrl and Tg mice fed a HFD. h, Western blot analyses of LSD1, Ucp1, and Fabp4 in the indicated adipose tissues of Ctrl and Tg mice fed a RD or HFD. β-Tubulin was used as a loading control. n=10 mice. Standard deviation represents+SEM, *p<0.05.

Figure 17:
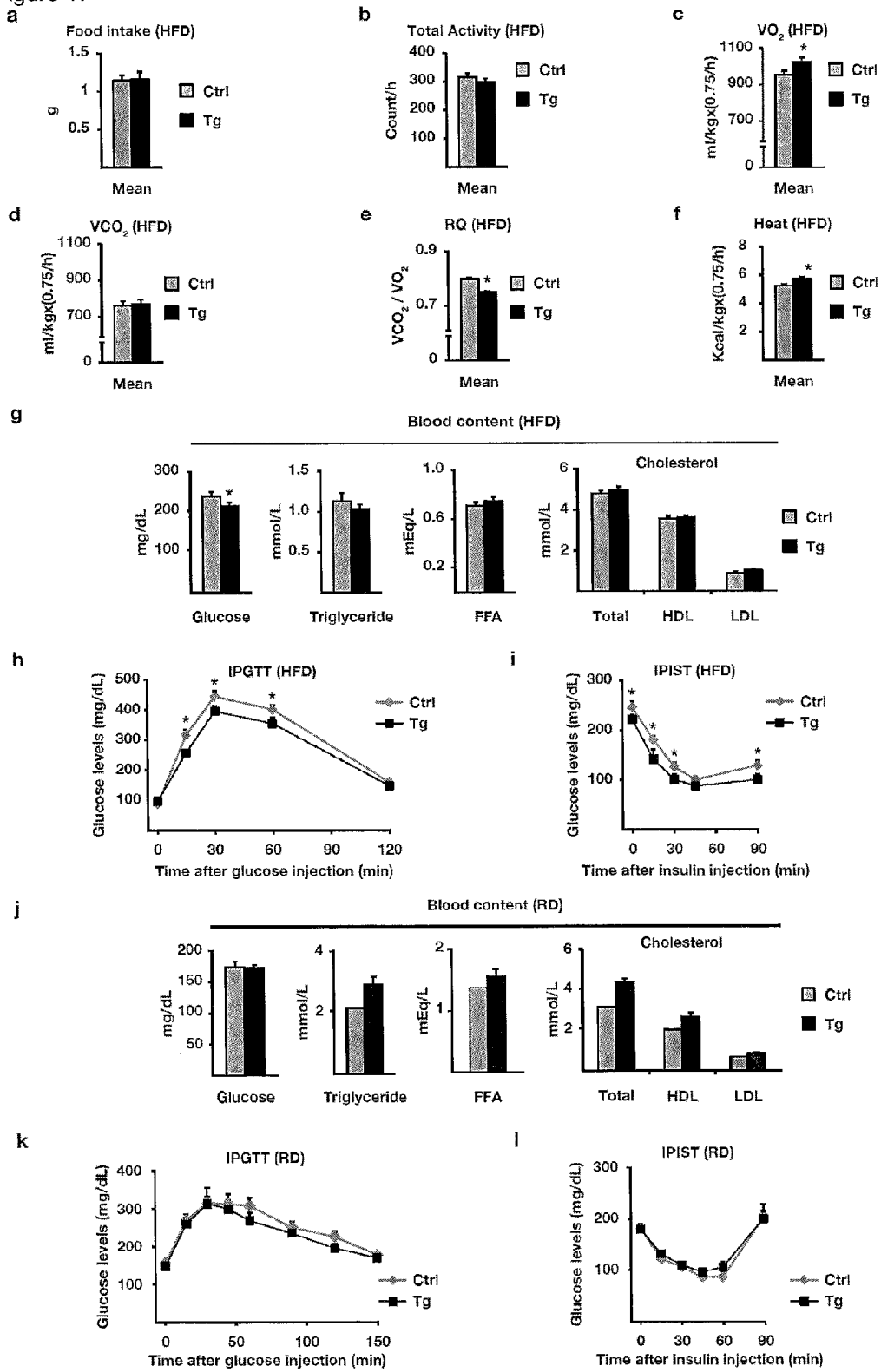

FIG. 17. LSD1 Tg mice are more resistant to high-fat diet-induced obesity and type-2 diabetes. a-h, (a) Food consumption, (b) spontaneous activity, (c) VO$_2$, (d) VCO$_2$, (e) respiratory quotient (RQ), (f) heat production, (g) serum glucose, triglyceride free fatty acid (FFA), and cholesterol (Total: total cholesterol, HDL: high density lipoprotein, and LDL: low density lipoprotein) levels of Ctrl and Tg mice fed a HFD. h,i, Intraperitoneal glucose tolerance test (h, IPGTT), and intraperitoneal insulin sensitive test (i, IPIST) of Ctrl and Tg mice fed a HFD. j, Serum glucose, triglyceride, free fatty acid (FFA), and cholesterol (Total: total cholesterol, HDL: high density lipoprotein, and LDL: low density lipoprotein) levels of Ctrl and Tg mice fed a RD. k,l, (k) IPGTT and (l) IPIST of Ctrl and Tg mice fed a RD. n=10 mice. Standard deviation represents+SEM, *p<0.05.

Figure 18:
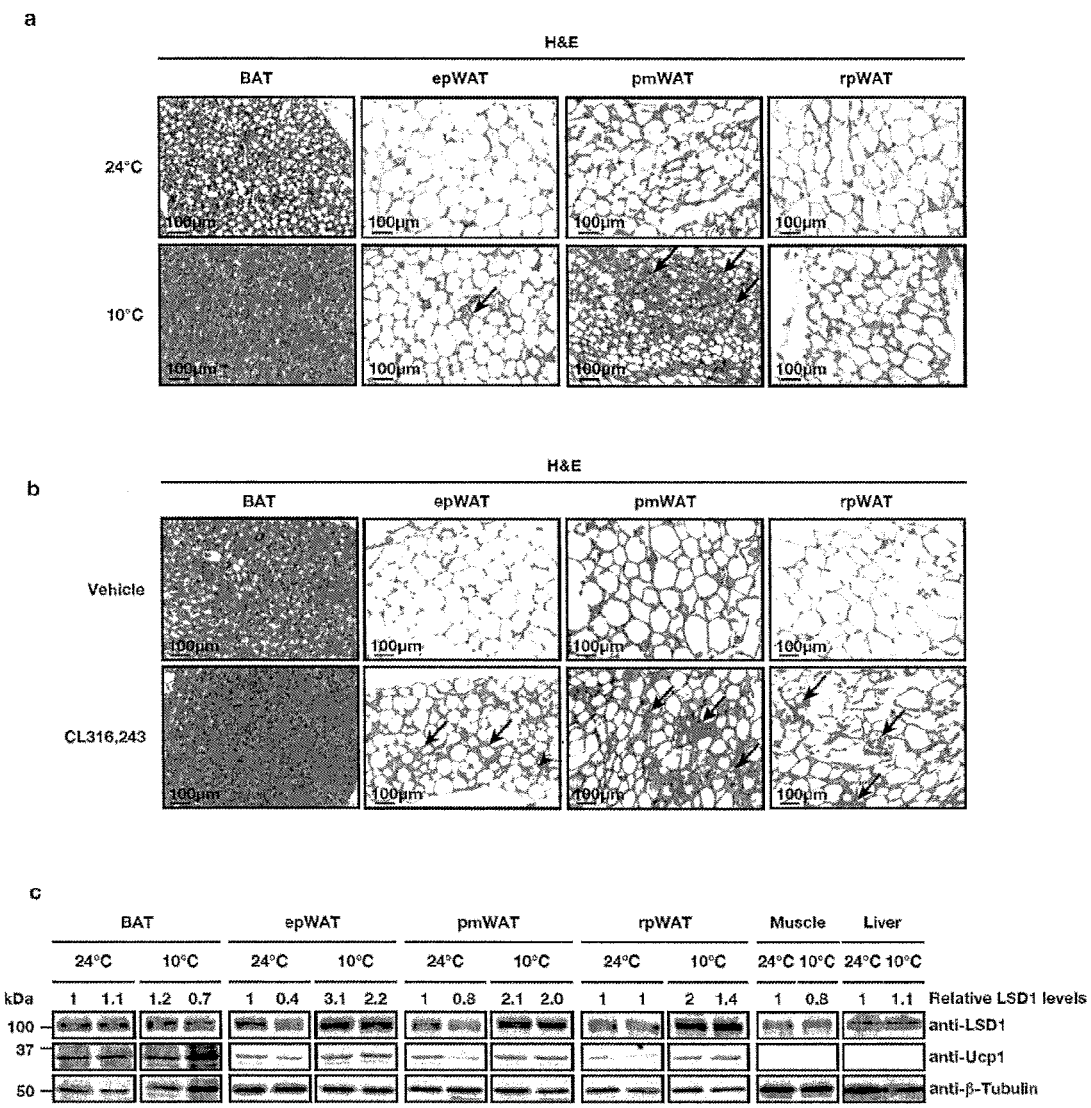

FIG. 18. LSD1 is induced in white fat pads after cold exposure or β3-adrenergic treatment of mice. a,b, H&E staining of indicated adipose tissues of mice (a) maintained at either 24 or 10° C., or (b) treated with vehicle or the β3-adrenergic agonist CL316,243. Black arrows show beige fat islets. c, Western blot analysis of LSD1 and Ucp1 in the indicated tissues of mice maintained at 24 or 10° C. Indicated LSD1 levels were normalized to β-Tubulin.

Figure 19:
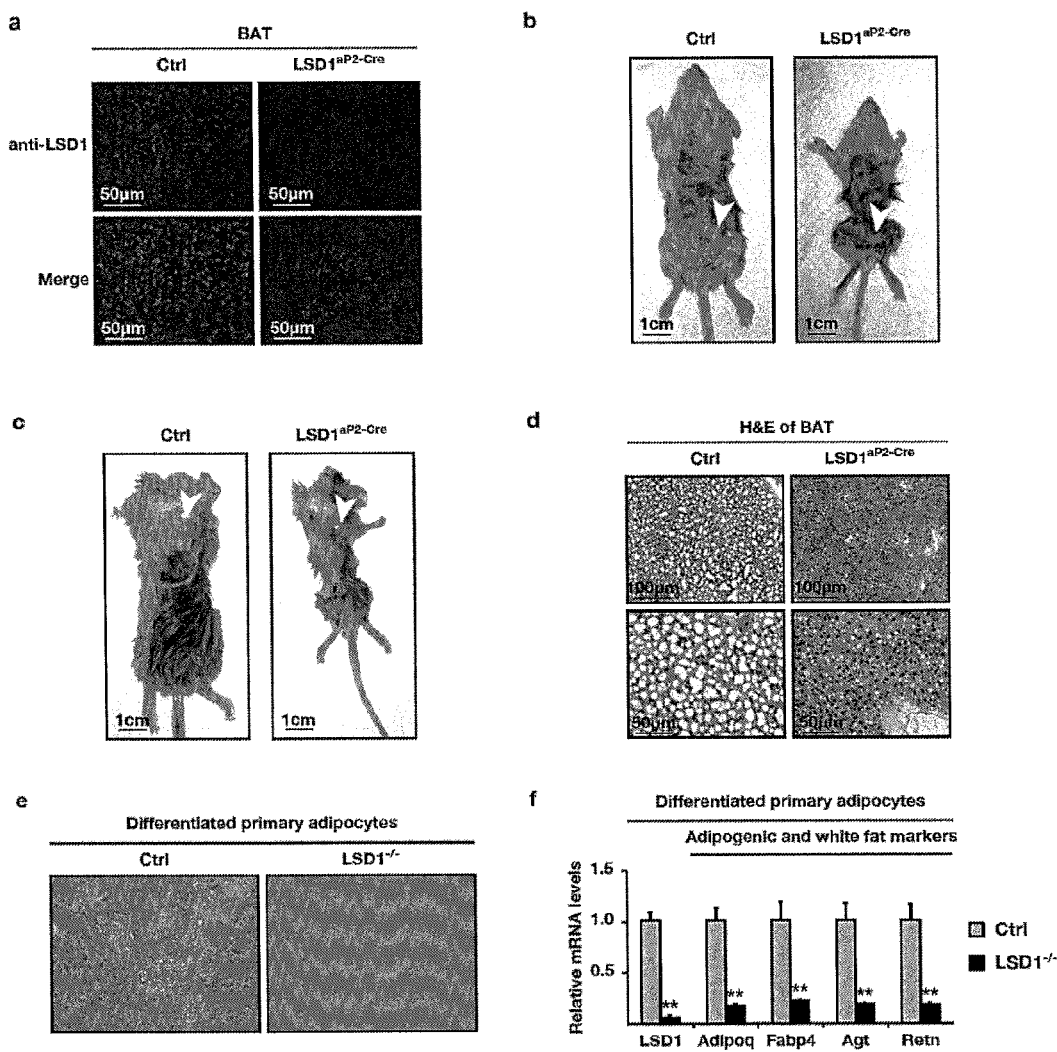

FIG. 19. Fat-specific deletion of LSD1 impairs WAT adipogenesis. a, Immunofluorescence analysis of LSD1 (red) in interscapular brown adipose tissue (BAT) of control (Ctrl) and $LSD1^{aP2-Cre}$ mice. Nuclei were counterstained with DAPI. b-d, Macroscopic view of (b) epWAT and (c) BAT of Ctrl and $LSD1^{aP2-Cre}$ mice. Fat depots are indicated by arrow heads (d) H&E staining of BAT of Ctrl and $LSD1^{aP2-Cre}$ mice. e, Microscopic view of stromal vascular fraction of fat from Ctrl and $LSD1^{Rosa26-CreERT}$ mice treated for five days with tamoxifen and differentiated into adipocytes. Magnification: 200×. f, Relative transcript levels of LSD1 and the indicated adipogenic and white fat-selective markers in differentiated Ctrl and $LSD1^{-/-}$ primary adipocytes. a-d, n=6; e,f, n=5. Standard deviation represents+SEM, **p<0.01.

Figure 20:
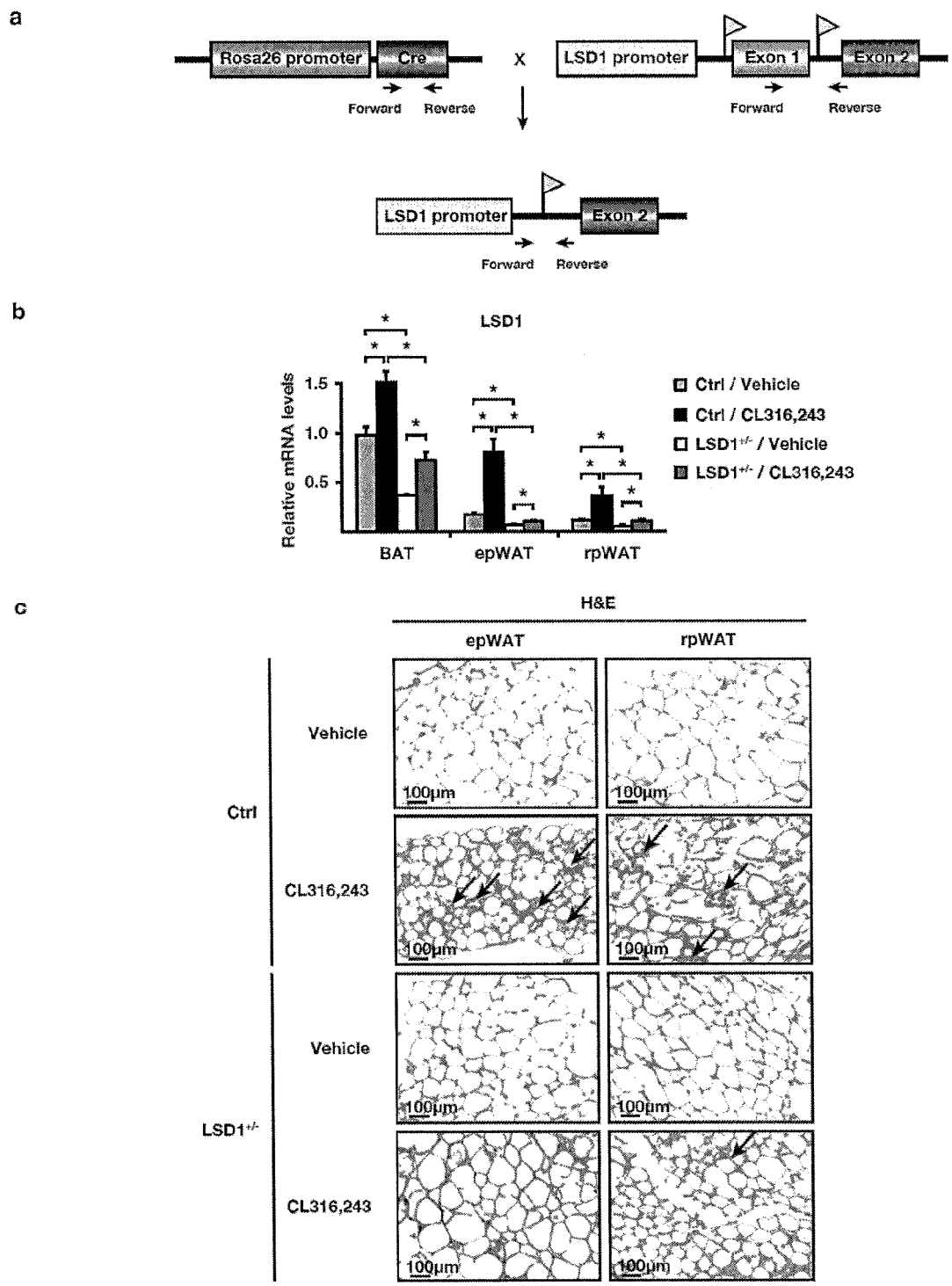

FIG. 20. β3-adrenergic signalling is impaired in $LSD1^{+/-}$ mice. a, Schematic representation of the Rosa26-Cre transgene and the floxed L2 LSD1 allele. Arrows indicate the locations of primers used to characterize the different alleles. Yellow flags show LoxP sites. b, Relative LSD1 transcript levels in the indicated adipose tissues of control (Ctrl) and heterozygous LSD1 ($LSD1^{+/-}$) mice treated with vehicle or CL316,243. c, H&E staining of indicated adipose tissues of Ctrl and $LSD1^{+/-}$ mice treated with vehicle or CL316,243. Black arrows indicate beige fat islets. b and c, n=5 mice. Standard deviation represents+SEM, *p<0.05.

Figure 21:
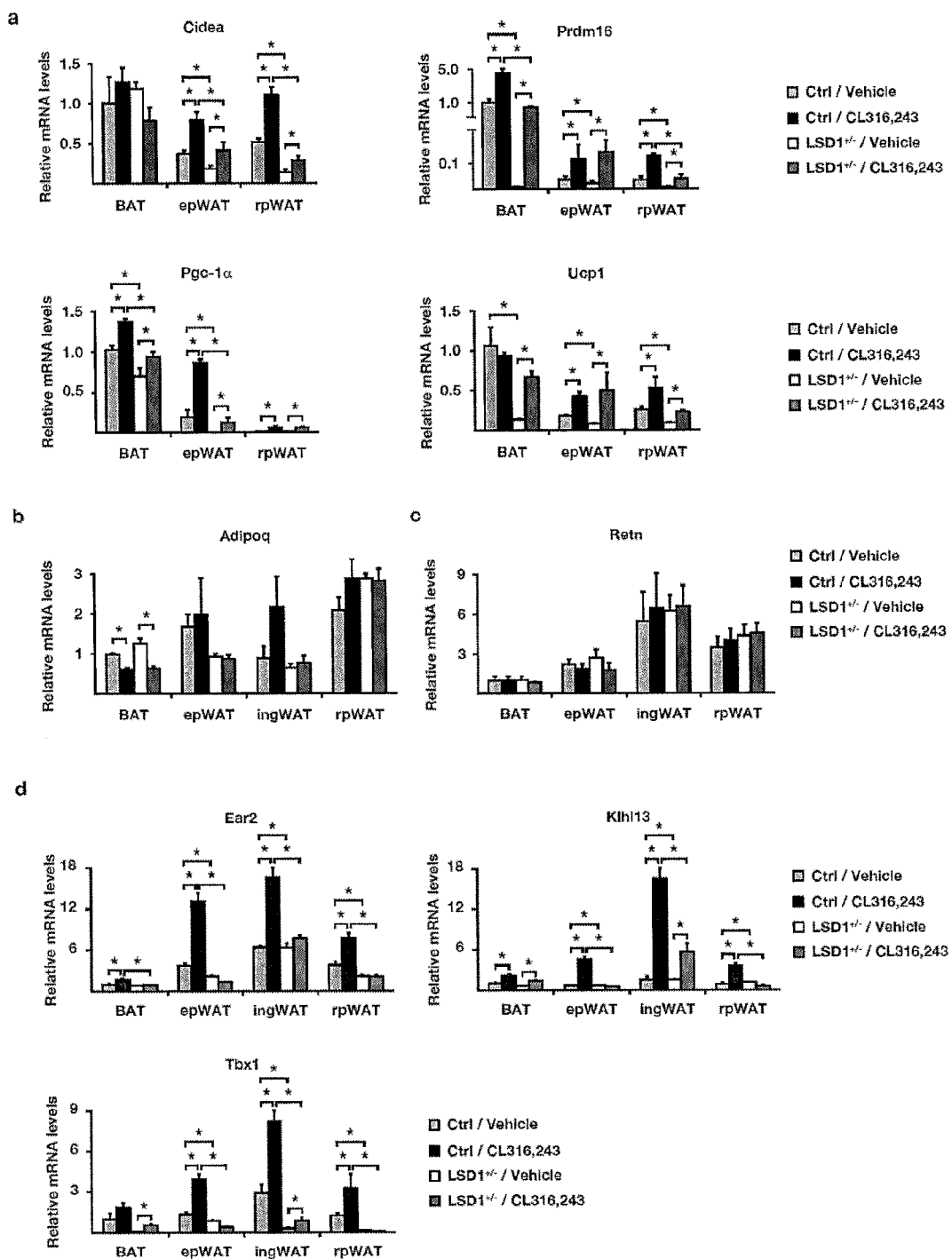

FIG. 21. β3-adrenergic signalling promotes the beige fat programme through LSD1. Relative transcript levels of (a) oxidative, (b) adipogenic, (c) white, and (d) beige fat-selective markers in the indicated adipose tissues of Ctrl and $LSD1^{+/-}$ mice treated with vehicle or CL316,243. n=10 mice. Standard deviation represents+SEM, *p<0.05.

Figure 22:
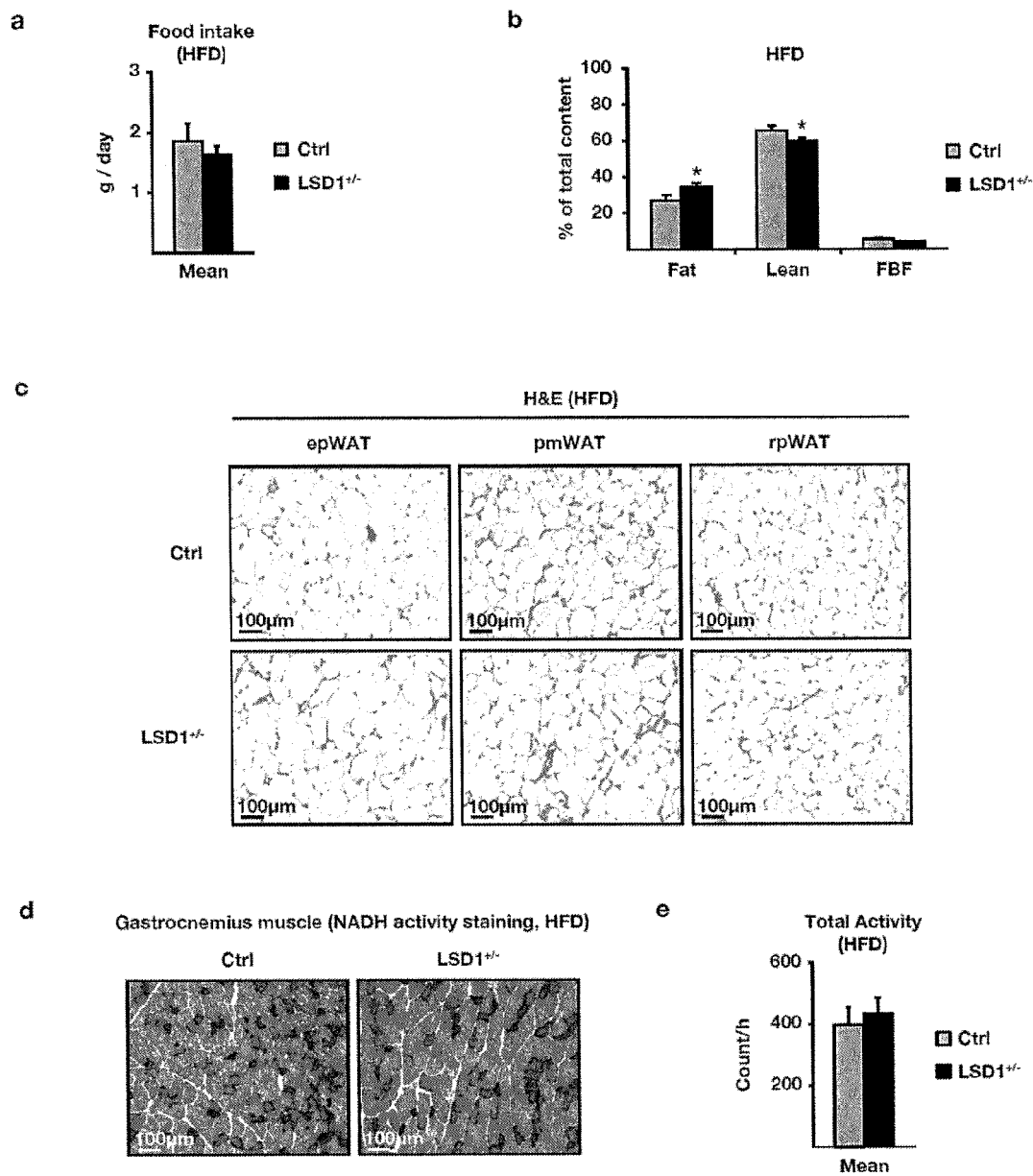

FIG. 22. $LSD1^{+/-}$ mice are prone to obesity due to decreased oxidative capacities in adipose tissue. a-e, (a) Food consumption, (b) fat, lean, and FBF content, (c) H&E staining of indicated adipose tissues, (d) histochemical staining of NADH dehydrogenase activity in gastrocnemius muscle, (e) spontaneous activity of Ctrl and $LSD1^{+/-}$ mice fed a HFD. n=6 mice. Standard deviation represents+SEM, *p<0.05.

Figure 23:
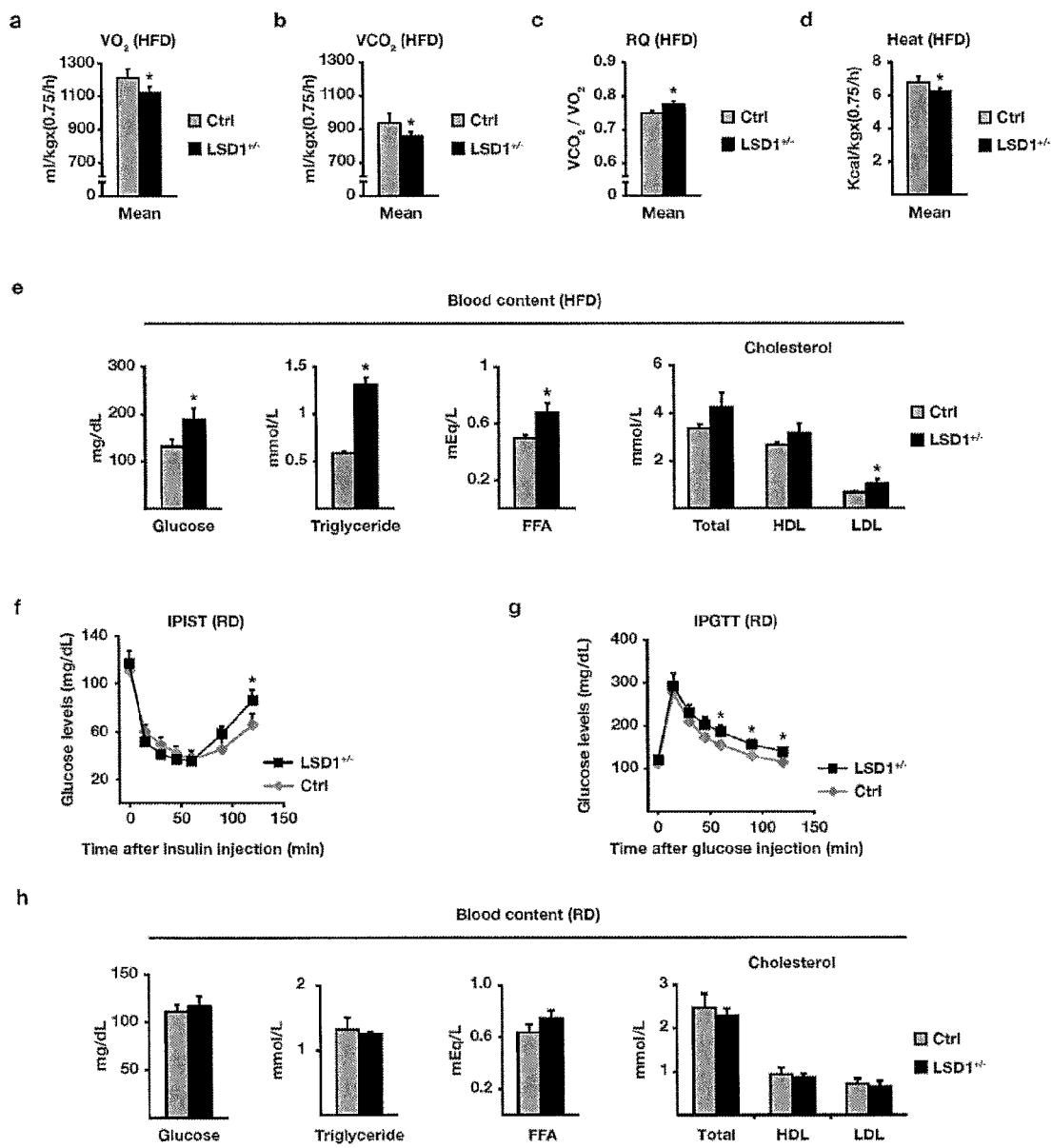

FIG. 23. $LSD1^{+/-}$ mice are prone to obesity and type-2 diabetes. a-e, (a) $VO_2$, (b) $VCO_2$, (c) respiratory quotient (RQ), (d) heat production, (e) serum glucose, triglyceride, levels, free fatty acid (FFA), and cholesterol (Total: total cholesterol, HDL: high density lipoprotein, and LDL: low density lipoprotein) levels of Ctrl and $LSD1^{+/-}$ mice fed a HFD. f,g, (f) IPIST and (g) IPGTT of Ctrl and $LSD1^{+/-}$ mice fed a RD. h, Serum glucose, triglyceride, levels, FFA, and cholesterol levels of Ctrl and $LSD1^{+/-}$ mice fed a RD. n=6 mice. Standard deviation represents+SEM, *p<0.05.

Figure 24:
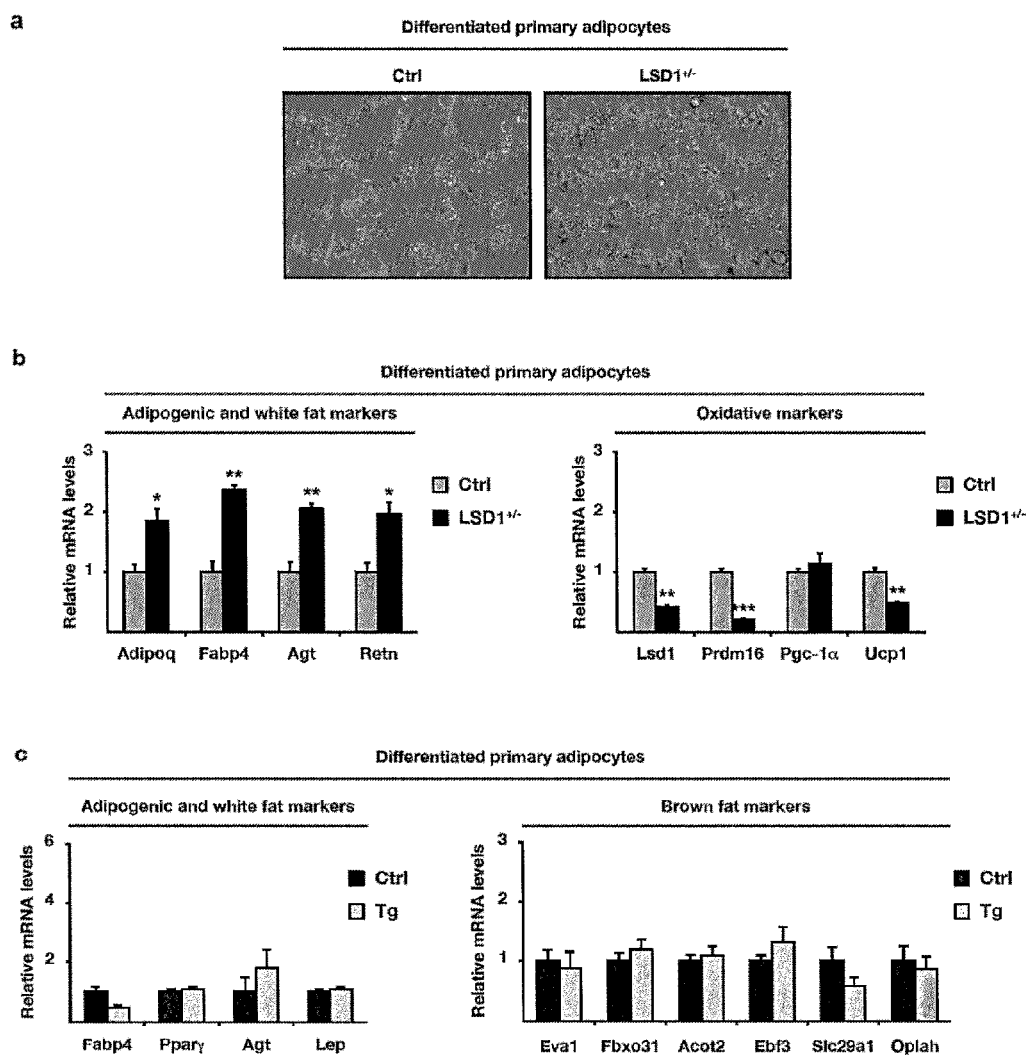

FIG. 24. LSD1 is essential to maintain oxidative capacities of adipocytes. a, Microscopic view of primary adipocytes isolated from the stromal vascular fraction of fat from Ctrl and $LSD1^{+/-}$ mice and differentiated in vitro. Magnification: 200×. b, Relative transcript levels of the indicated adipogenic, white fat-selective, and oxidative markers in differentiated Ctrl and $LSD1^{+/-}$ primary adipocytes. c, Pre-adipocytes isolated from the stromal vascular fraction from Ctrl and Tg LSD1 mice were differentiated in vitro. Relative transcript levels of the indicated adipogenic, white, and brown fat-selective markers in differentiated Ctrl and Tg primary adipocytes. Standard deviation represents+SEM (n=5), *p<0.05, p<0.01, *p<0.001.

Figure 25:
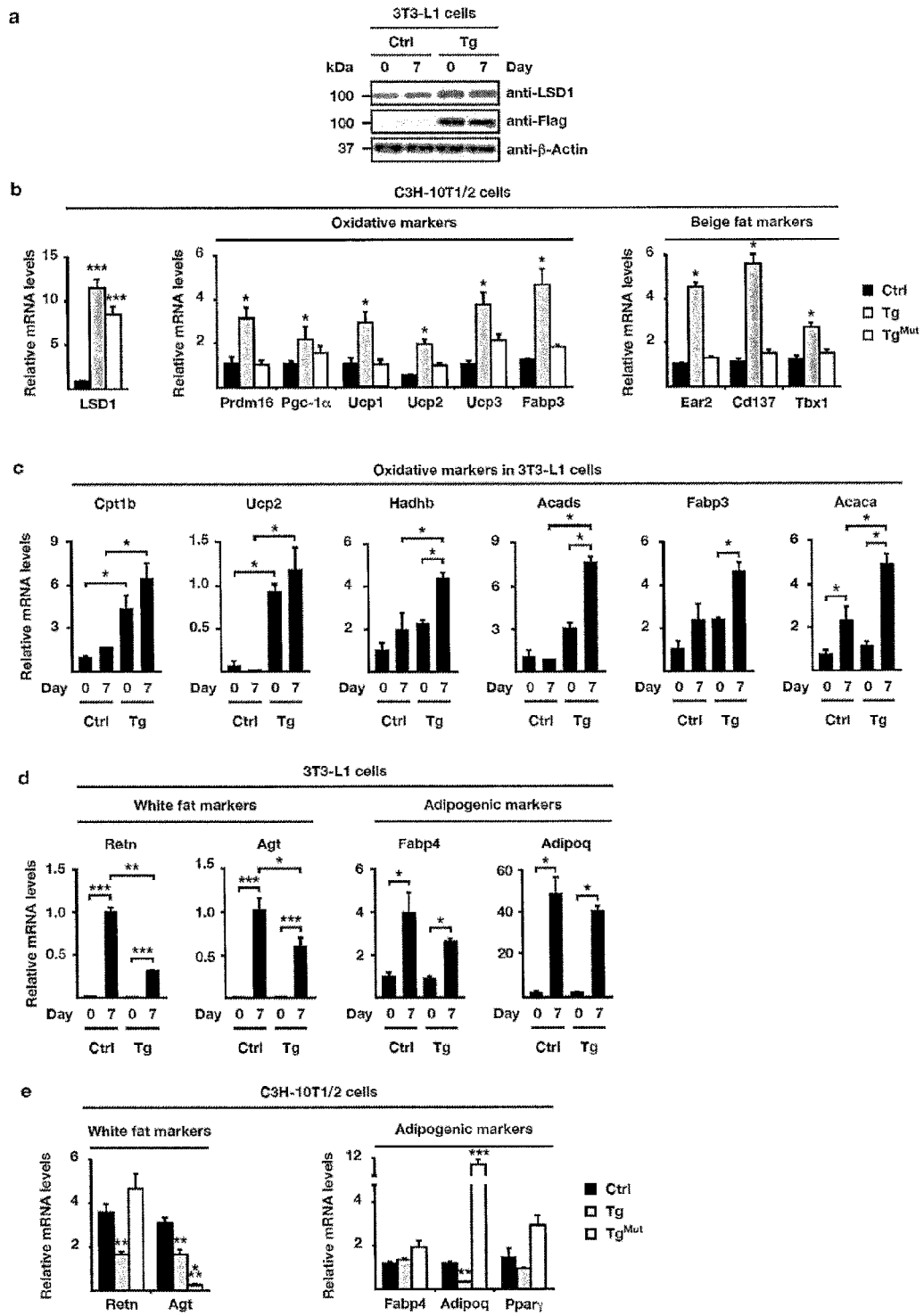

FIG. 25. LSD1 promotes the formation of functional beige adipocytes in vitro. a, Western blot analysis of LSD1 in undifferentiated (day 0) and differentiated (day 7) control (Ctrl) 3T3-L1 and LSD1 overexpressing (Tg) cells. Flag antibody was used to detect expression of the transgene. β-Actin served as a loading control. b, Relative transcript levels of LSD1, oxidative, and beige fat-selective markers in differentiated C3H-10T1/2 control (Ctrl), LSD1 (Tg), or inactive LSD1 ($Tg^{Mut}$) overexpressing cells. c, Relative transcript levels of oxidative markers in 3T3-L1(Ctrl) and 3T3-L1(Tg) cells at days 0 and 7 of differentiation. d, Relative transcript levels of white fat-selective, and adipogenic markers in 3T3-L1(Ctrl) and 3T3-L1(Tg) cells at days 0 and 7 of differentiation. e, Relative transcript levels of white fat-selective and adipogenic markers in differentiated Ctrl, Tg, and $Tg^{Mut}$ C3H-10T1/2 cells. Standard deviation represents+SEM (n=6), *p<0.05, p<0.01, *p<0.001.

Figure 26:
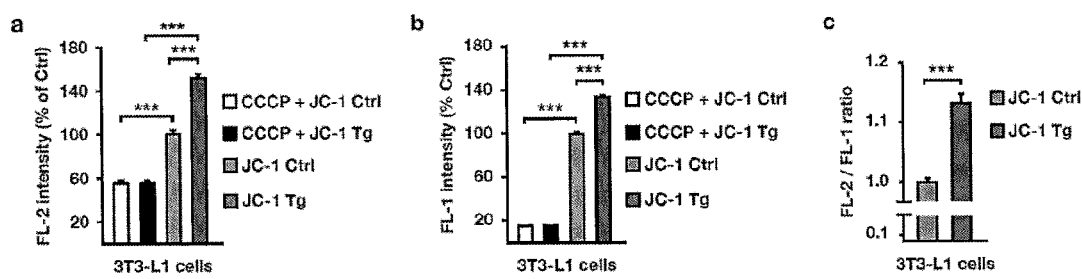

FIG. 26. LSD1 promotes mitochondrial biogenesis and function. a,b, (a) Relative mitochondrial activity determined by red fluorescence intensity of JC-1 aggregates (FL-2) and (b) relative mitochondrial mass determined by green fluorescence intensity of JC-1 aggregates (FL-1) in 3T3-L1(Ctrl) and 3T3-L1(Tg) cells at day 7 of differentiation. Samples treated with the mitochondrial membrane potential disrupter CCCP represent background staining. c, Ratio of mitochondrial activity (FL-2) relative to mitochondrial mass (FL-1) in 3T3-L1(Ctrl) and 3T3-L1(Tg) cells at day 7 of differentiation. Standard deviation represents+SEM (n=6), ***p<0.001.

Figure 27:
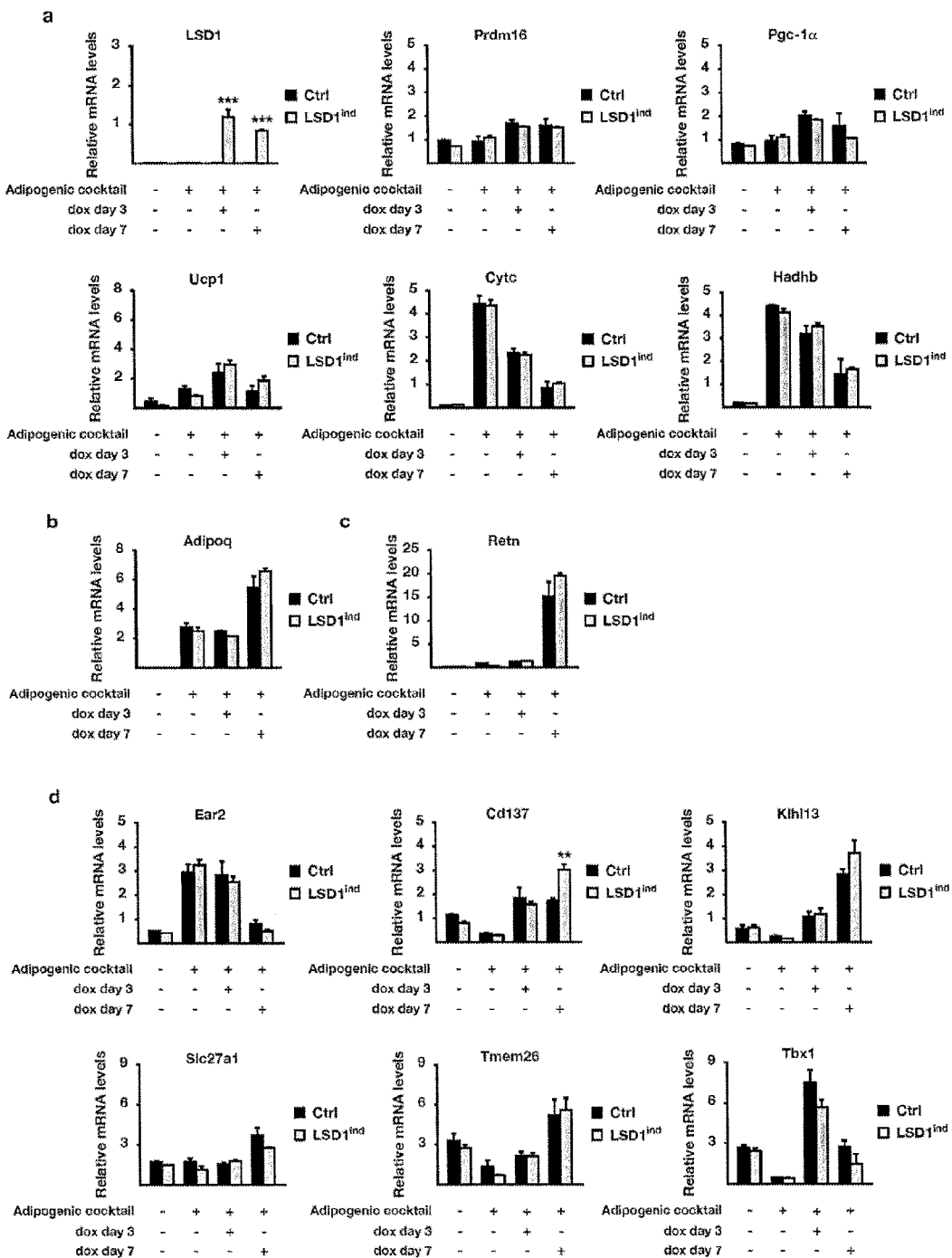

FIG. 27. LSD1 does not promote transdifferentiation of white adipocytes. Relative transcript levels of (a) LSD1 and oxidative, (b) adipogenic, (c) white fat-selective, and (d) beige fat-selective markers in 3T3-L1 cells infected with either control virus (Ctrl) or virus expressing LSD1 upon doxycyclin (dox) treatment ($LSD1^{ind}$). Time points of dox treatment are indicated by +. Standard deviation represents+SEM (n=6), p<0.01, *p<0.001.

Figure 28:
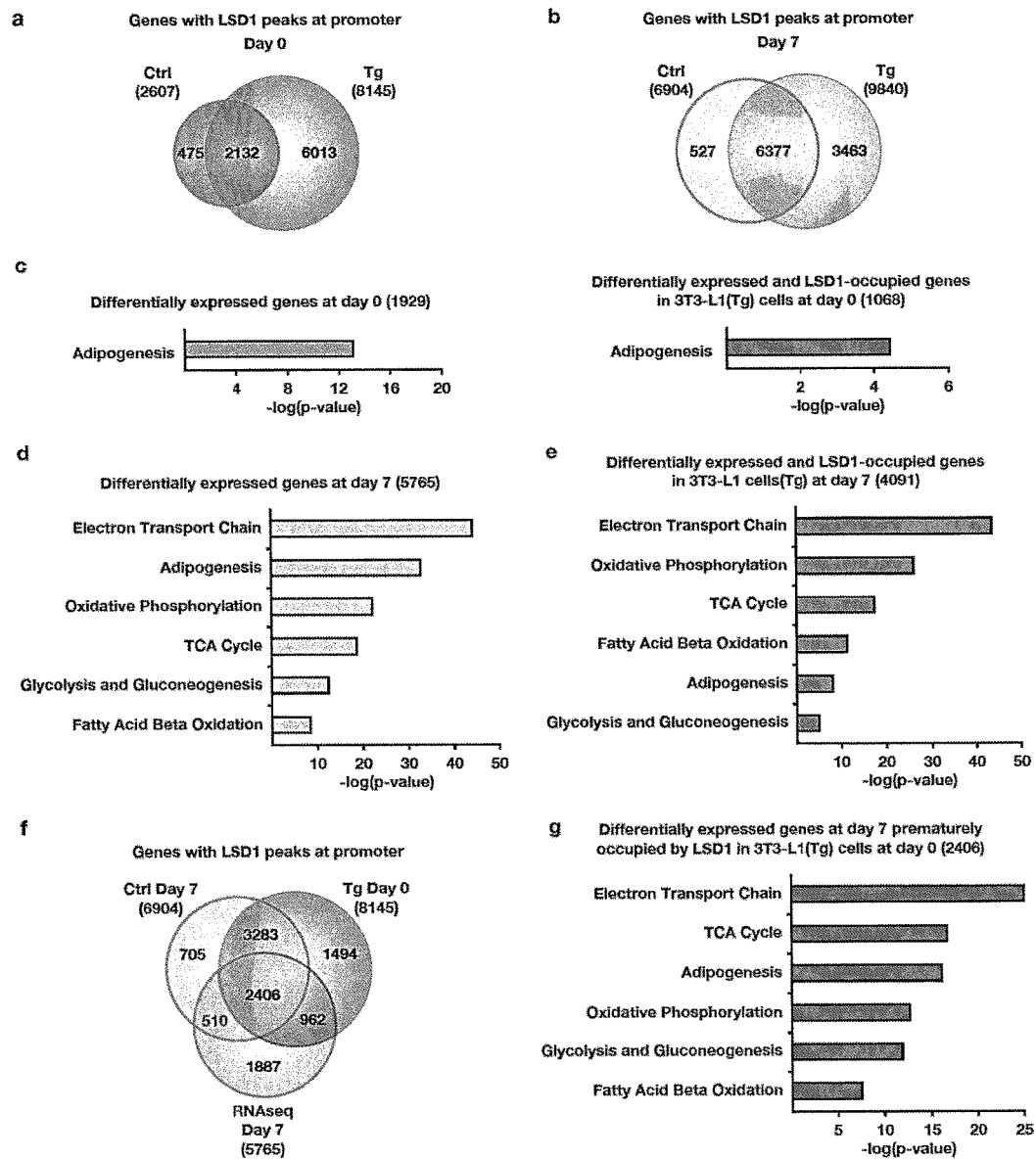

FIG. 28. LSD1 promotes oxidative metabolic pathways. a,b, Venn diagram depicting the number of genes with LSD1 peaks at promoters in 3T3-L1(Ctrl) and 3T3-L1(Tg) cells at (a) day 0 and (b) day 7 of differentiation. c-e, Enriched pathways obtained from GOterm analyses for the indicated sets of genes. f, Venn diagram depicting the number of genes with LSD1 peaks at promoters in 3T3-L1(Ctrl) and 3T3-L1 (Tg) cells at days 7 and 0, respectively, and differentially expressed genes between 3T3-L1(Tg) and 3T3-L1(Ctrl) cells at day 7 of differentiation. g, Enriched pathways obtained from a GOterm analysis for the indicated sets of genes.

FIG. 29. LSD1 promotes mitochondrial functions. a, Localization of LSD1 at promoters of Cpt1 and Cpt2 in 3T3-L1(Ctrl) and 3T3-L1(Tg) cells at day 0. Differential expression of the indicated genes between 3T3-L1(Tg) and 3T3-L1(Ctrl) cells at days 0 and 7 of differentiation. (FC) Logarithmic fold change. b, Relative transcript levels of representative genes encoding the mitochondrial electron transport chain in 3T3-L1(Ctrl) and 3T3-L1(Tg) cells at days 0 and 7. c,d, (left panel) Relative transcript levels of representatives of (c) glycolysis and (d) TCA cycle in 3T3-L1(Ctrl) and 3T3-L1(Tg) cells at days 0 and 7, and (right panel) in the indicated adipose tissues of Ctrl and Tg mice. b-d, n=6; c,d, n=10 mice. BAT served as a positive control. Standard deviation represents+SEM, *p<0.05.

Figure 30:
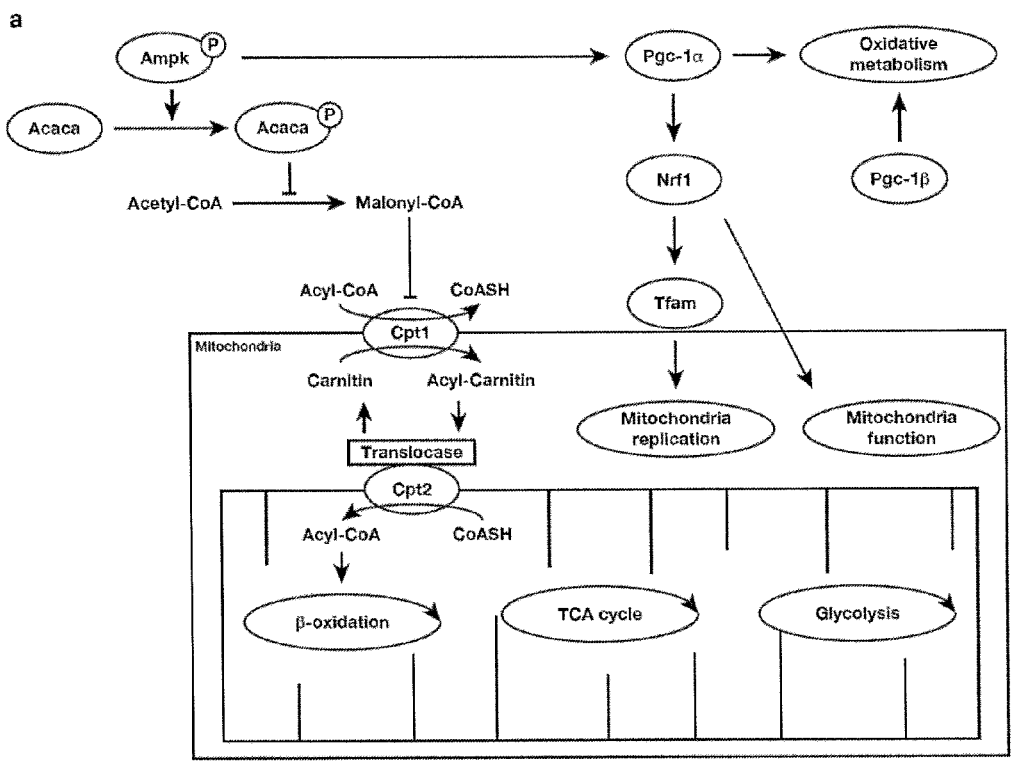

FIG. 30. LSD1 fosters oxidative metabolism. a, Modified "energy metabolism pathway" from Hood et al[64]. b, Localization of LSD1 at promoters of Acaca, Pgc-1α, Pgc-1β, Nrf1, and Tfam in 3T3-L1(Ctrl) and 3T3-L1(Tg) cells at day 0. Differential expression of the indicated genes between 3T3-L1(Tg) and 3T3-L1(Ctrl) cells at days 0 and 7 of differentiation. (FC) Logarithmic fold change.

Figure 31:
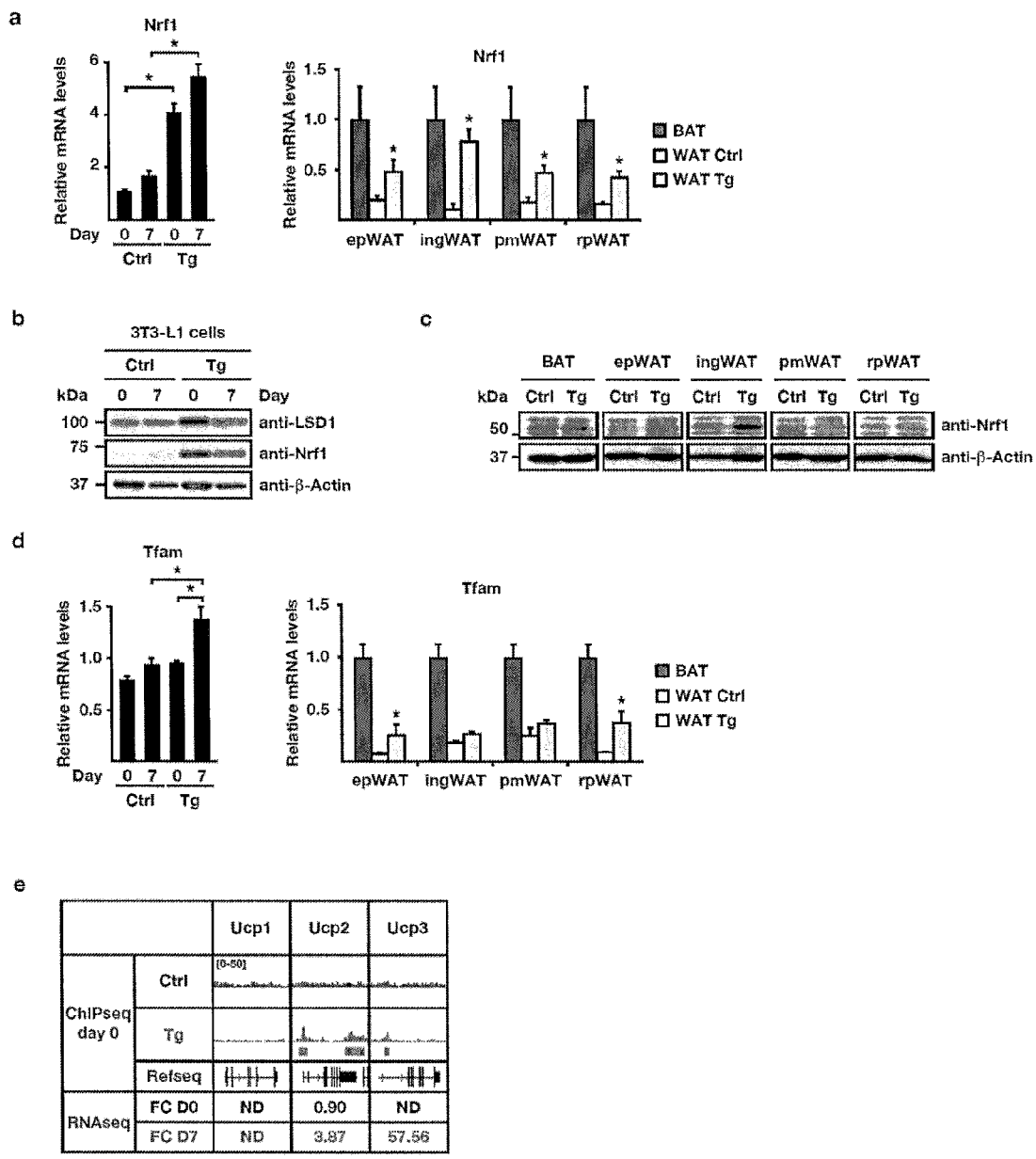

FIG. 31. LSD1 induces expression of Nrf1, Tfam, and Ucp. a, (left panel) Relative transcript levels of Nrf1 in 3T3-L1(Ctrl) and 3T3-L1(Tg) cells at days 0 and 7, and (right panel) in the indicated adipose tissues of Ctrl and Tg mice. b, Western blot analysis of LSD1 and Nrf1 of 3T3-L1(Ctrl) and 3T3-L1(Tg) cells at indicated days. β-Actin served as a loading control. c, Western blot analysis of Nrf1 in the indicated adipose tissues of Ctrl and Tg mice. β-Actin was used as a loading control. d, (left panel) Relative transcript levels of Tfam in 3T3-L1(Ctrl) and 3T3-L1(Tg) cells at days 0 and 7, and (right panel) in the indicated adipose tissues of Ctrl and Tg mice. e, Localization of LSD1 at promoters of Ucp1, Ucp2, and Ucp3 in 3T3-L1(Ctrl) and 3T3-L1(Tg) cells at day 0, and differential expression of the Ucp genes between 3T3-L1(Tg) and 3T3-L1(Ctrl) cells at days 0 and 7 of differentiation. a,b,d, n=6; a,c,d, n=10 mice. BAT served as a positive control. Standard deviation represents+SEM, *p<0.05.

FIG. 32. LSD1 and Nrf1 control the OXPHOS gene programme. Overlap of LSD1 and Nrf1 peaks at promoters of representative mitochondrial electron transport chain (complex I-V) genes in 3T3-L1 cells at indicated time points of differentiation, and differential expression of the representatives between 3T3-L1(Tg) and 3T3-L1(Ctrl) cells at days 0 and 7 of differentiation. (FC) Logarithmic fold change.

Figure 33:
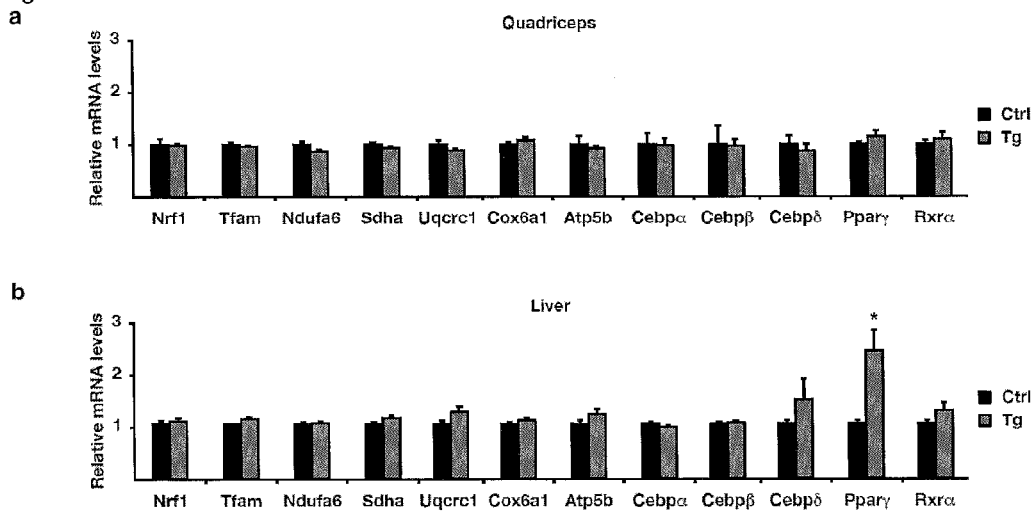

FIG. 33. Tissue-specific action of LSD1. a,b, Relative transcript levels of the indicated genes in (a) quadriceps muscle and (b) liver of Ctrl and Tg mice. n=10 mice. Standard deviation represents+SEM, *p<0.05.

Figure 34:
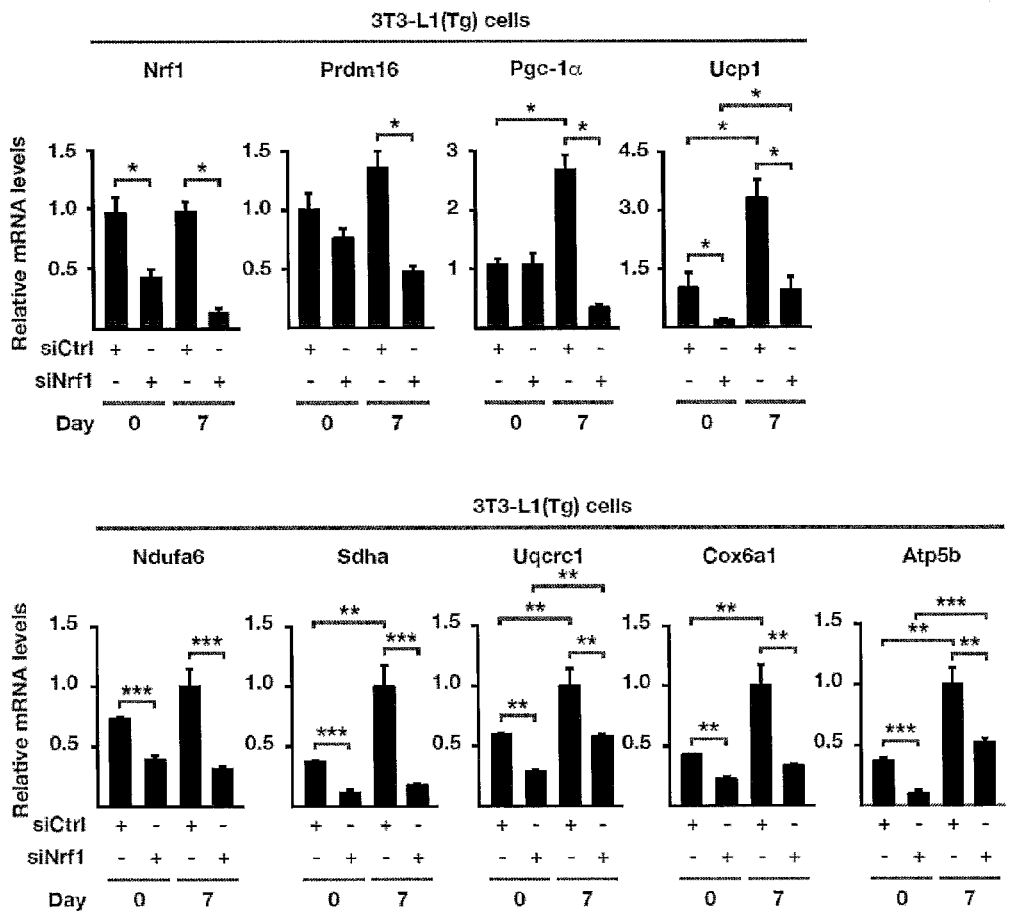

FIG. 34. LSD1 and Nrf1 control the OXPHOS gene programme. Relative transcript levels of the indicated genes in 3T3-L1(Tg) cells at days 0 and 7, treated with unrelated control siRNA or siRNA directed against Nrf1. Standard deviation represents+SEM n=6, *p<0.05, p<0.01, and *p<0.001.

Figure 35:
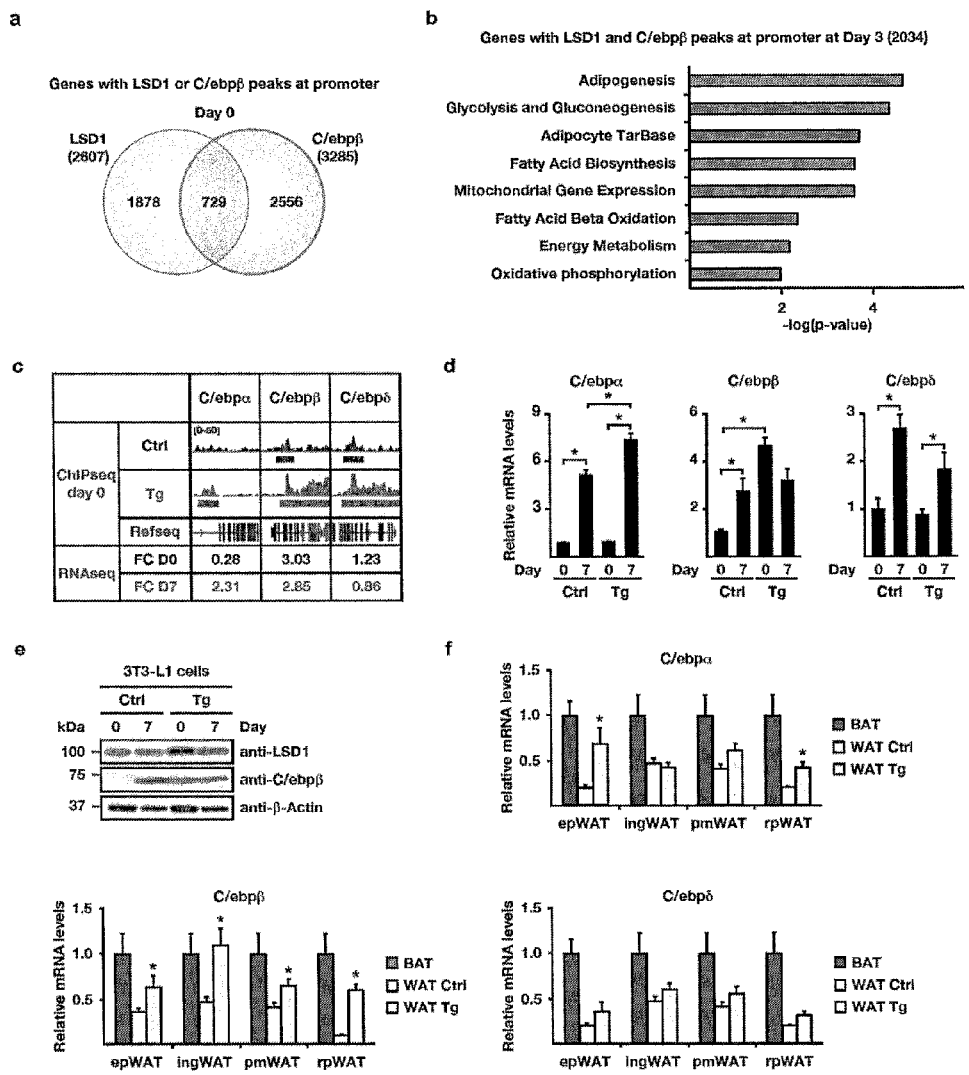

FIG. 35. Genome-wide binding pattern of LSD1 and C/ebpβ. a, Venn diagram showing the number of genes occupied by LSD1 or C/ebpβ in 3T3-L1(Ctrl) cells at day 0. b, Enriched pathways identified by a GOterm analysis of the common target genes at day 3 of differentiation c, LSD1 occupancy of the indicated C/ebp promoters in 3T3-L1(Ctrl) and 3T3-L1(Tg) cells at day 0 of differentiation, and differential expression of the indicated C/ebp genes between 3T3-L1(Tg) and 3T3-L1(Ctrl) cells at days 0 and 7 of differentiation. (FC) Logarithmic fold change. d, Relative transcript levels of C/ebpα, C/ebpβ, and C/ebpδ from undifferentiated (day 0) and differentiated (day 7) 3T3-L1(Ctrl) and 3T3-L1(Tg) cells. e, Western blot analysis of LSD1 and C/ebpβ of 3T3-L1(Ctrl) and 3T3-L1(Tg) cells at indicated days. β-Actin served as a loading control. f, Relative transcript levels of C/ebpα, C/ebpβ, and C/ebpδ in the indicated adipose tissues of Ctrl and Tg mice. d,e, n=6; f, BAT served as a positive control, n=10 mice. Standard deviation represents+SEM, *p<0.05 between Ctrl and Tg WAT (for f).

Figure 36:
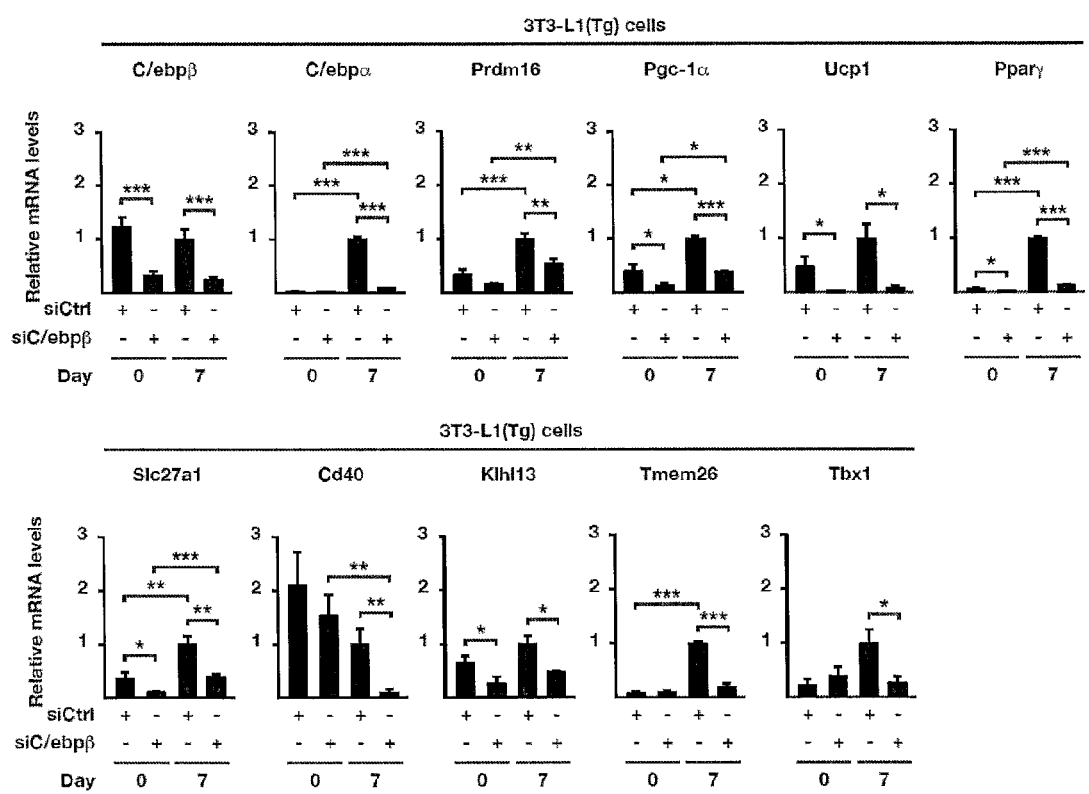

FIG. 36. LSD1 controls beige adipogenesis via C/ebpβ. Relative transcript levels of the indicated genes in 3T3-L1(Tg) cells at days 0 and 7, treated with unrelated control siRNA or siRNA directed against C/ebpβ. Standard deviation represents+SEM (n=6), *p<0.05, p<0.01, and *p<0.001.

Figure 37:
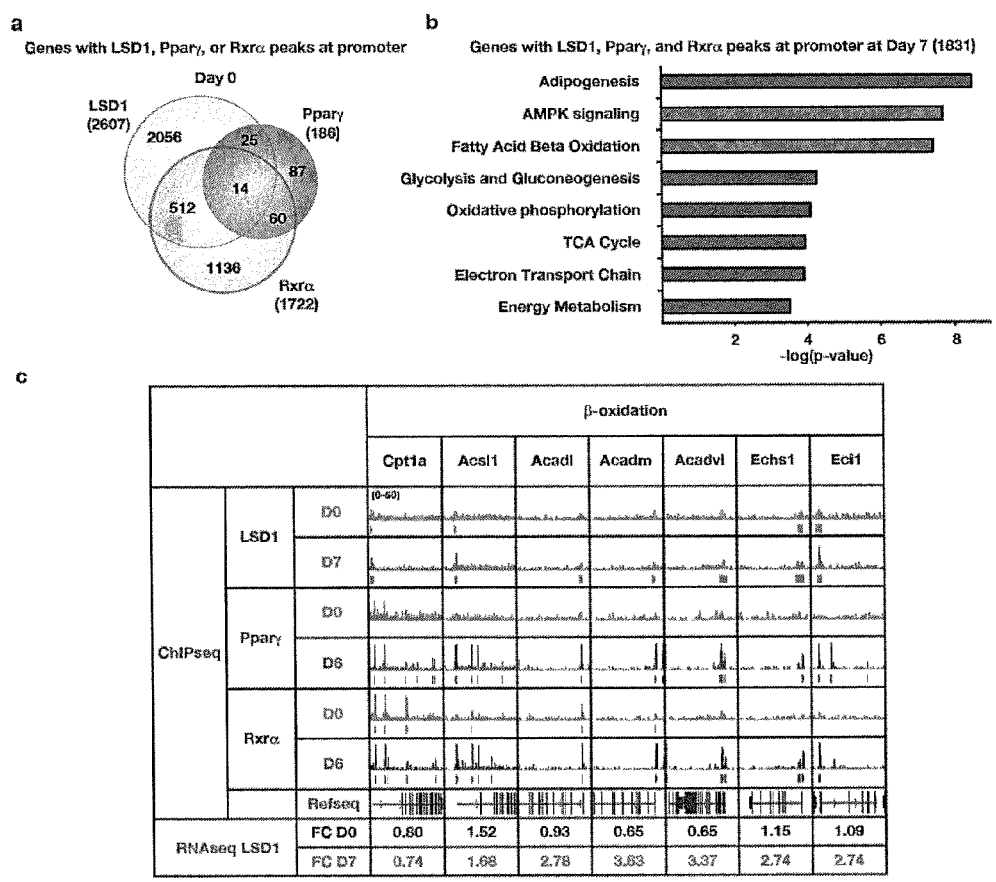

FIG. 37. a, Genome-wide binding pattern of LSD1, Pparγ, and Rxrα. Venn diagram showing the number of genes occupied by LSD1, Pparγ, and Rxrα in 3T3-L1 cells at day 0. b, Enriched pathways identified by a GOterm analysis of the common target genes in 3T3-L1 cells at day 7 of differentiation. c, Overlap of LSD1, Pparγ, and Rxrα peaks at promoters of representative genes of fatty acid β-oxidation at indicated days of differentiation in 3T3-L1 cells, and differential expression of representative between 3T3-L1(Tg) and 3T3-L1(Ctrl) cells at days 0 and 7 of differentiation. (FC) Logarithmic fold change.

Figure 38:
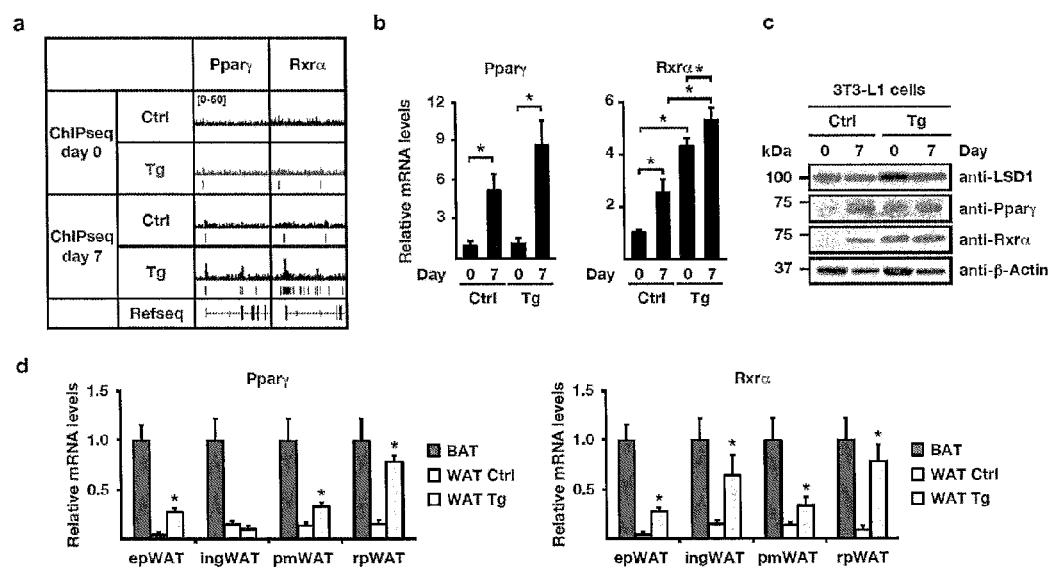

FIG. 38. Control of gene expression by LSD1. a, LSD1 occupancy of Pparγ and Rxrα promoters in 3T3-L1(Ctrl) and 3T3-L1(Tg) cells at days 0 and 7 of differentiation. b, Relative transcript levels of Pparγ, and Rxrα from undifferentiated (day 0) and differentiated (day 7) 3T3-L1(Ctrl) and 3T3-L1(Tg) cells. c, Western blot analysis of LSD1, Pparγ, and Rxrα of 3T3-L1(Ctrl) and 3T3-L1(Tg) cells at indicated days. β-Actin served as a loading control. d, Relative transcript levels of Pparγ, and Rxrα in the indicated adipose tissues of Ctrl and Tg mice. b,c, n=6; d, BAT served as a positive control, n=10 mice. Standard deviation represents+SEM, *p<0.05 between Ctrl and Tg WAT (for d).

Figure 39:
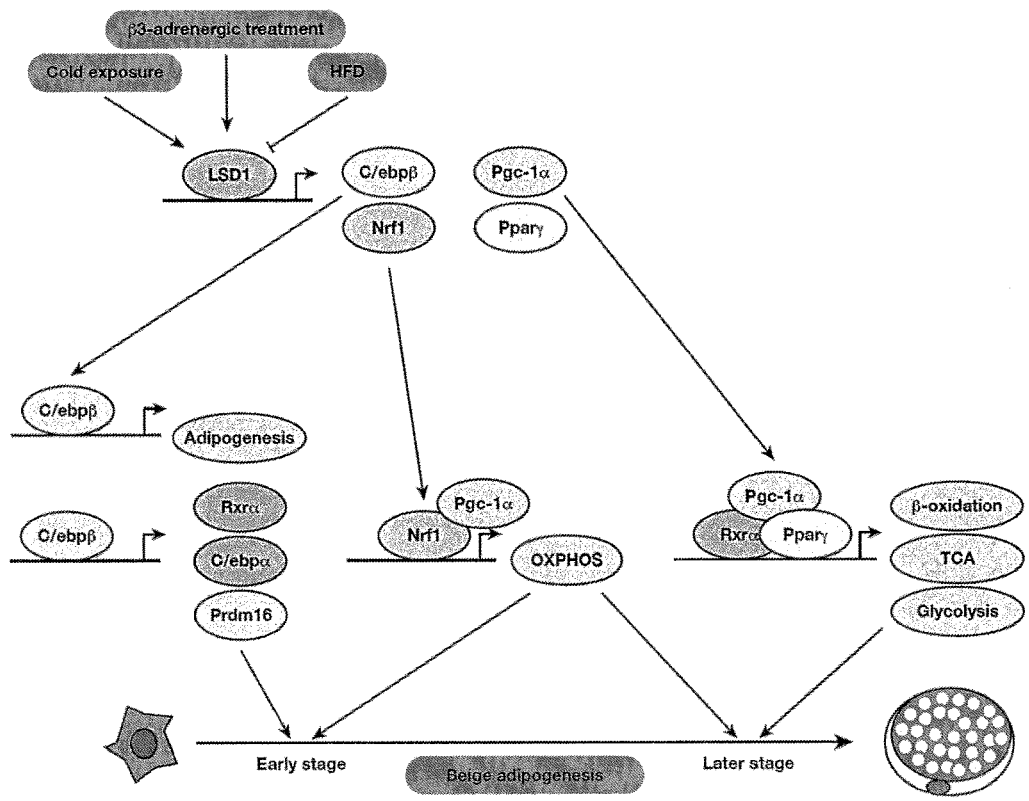

FIG. 39. LSD1 controls beige adipogenesis. LSD1 levels are regulated by environmental cues. LSD1 levels are increased by cold exposure or β3-adrenergic stimulation and decreased on a HFD. During early phase of differentiation, LSD1 controls adipogenesis via cooperation with C/ebpβ. C/ebpβ in concert with Prdm16 induces the beige fat programme. In cooperation with Nrf1 and Pgc-1α, LSD1 promotes mitochondrial biogenesis and OXPHOS. LSD1 reinforces adipogenesis via Pparγ/Rxrα/Pgc-1α by positively regulating metabolism (glycolysis, TCA cycle, and β-oxidation).

Figure 40:
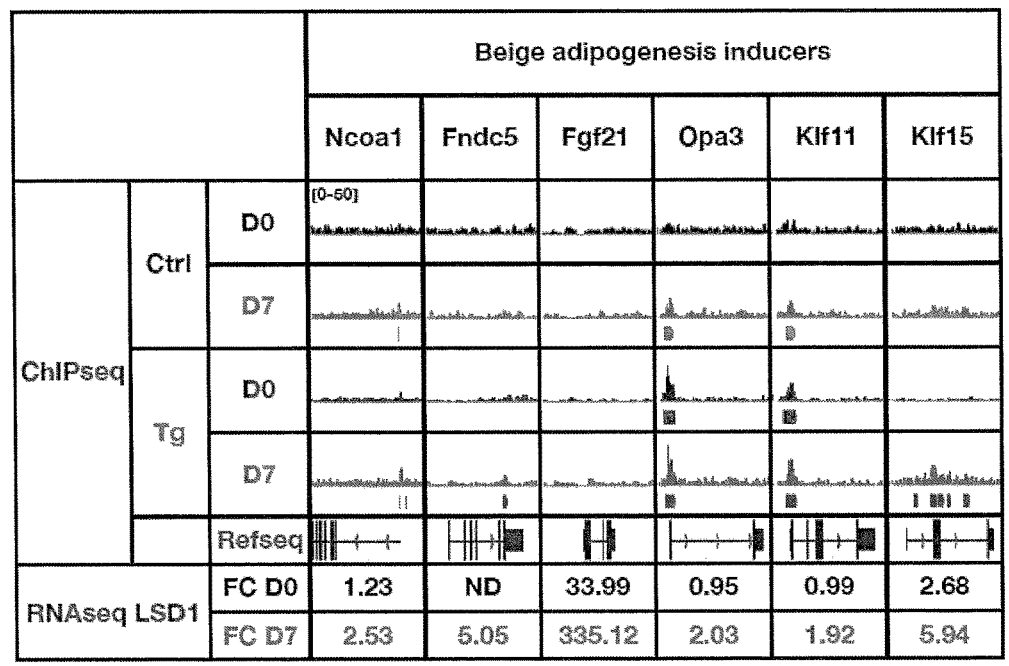

FIG. 40. LSD1 occupancy of the indicated promoters of beige adipogenesis inducers in 3T3-L1(Ctrl) and 3T3-L1(Tg) cells at days 0 and 7 of differentiation, and differential expression of the indicated genes between 3T3-L1(Tg) and 3T3-L1(Ctrl) cells at days 0 and 7 of differentiation. (FC) Logarithmic fold change.

EXAMPLES

Results
LSD1 Promotes Formation of Functional Beige Fat

Figure 1:
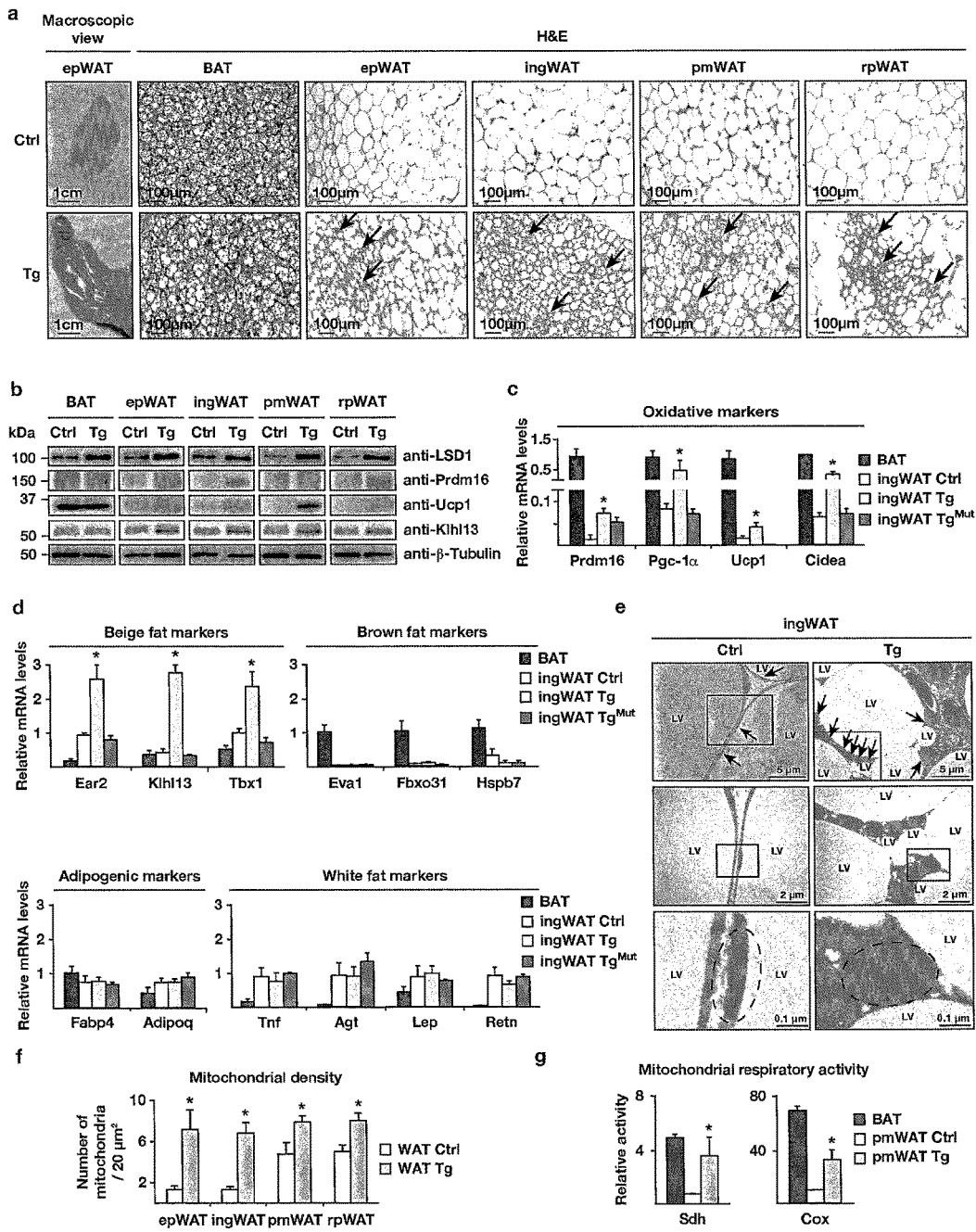
FIG. 1. Expression of LSD1 in transgenic mice induces the formation of functional beige fat in white adipose tissue. a, Macroscopic view of epididymal fat and haematoxylin and eosin staining (H&E) of interscapular brown adipose tissue (BAT), epididymal (epWAT), inguinal (ingWAT), perimuscular (pmWAT), and retroperitoneal (rpWAT) white adipose tissue of control (Ctrl) and LSD1 transgenic (Tg) mice. Black arrows indicate beige fat islets. b, Western blot analyses of LSD1, Prdm16, Ucp1, and Klhl13 in the indicated adipose tissues of Ctrl and Tg mice. β-Tubulin was used as a loading control. c, d, Relative transcript levels of the indicated (c) oxidative, (d) beige fat-selective, brown fat-selective, adipogenic, and white fat-selective markers in ingWAT of Ctrl, Tg, and transgenic mice expressing enzymatically inactive LSD1 mutant ($Tg^{Mut}$). e, Ultrastructure analysis of ingWAT of Ctrl and Tg mice. Black arrows indicate mitochondria. LV: lipid vesicle. Magnified regions are delimited by squares. f, Density of mitochondria determined from ultrastructure analysis of indicated adipose tissues of Ctrl and Tg mice. g, Determination of Sdh (mitochondrial respiratory chain complex II) and Cox (mitochondrial respiratory chain complex IV) activities in pmWAT of Ctrl and Tg mice. BAT of Ctrl mice was used as a positive control. a-d, n=10 mice. e-g, n=5 mice. Standard deviation represents+SEM, *$p<0.05$.

To investigate physiological functions of LSD1 in vivo, we analysed transgenic (Tg) mice ubiquitously expressing human LSD1 under the control of the Rosa26 promoter (FIG. 7a). Macroscopic inspection revealed intense browning of white fat pads of Tg mice (FIG. 1a). Detailed histological analyses showed the presence of multilocular brown or beige fat islets in all types of WAT [i.e. epididymal (ep), inguinal (ing), perimuscular (pm), and retroperitoneal (rp) WAT], whereas the morphology of interscapular BAT was not altered (FIG. 1a). Western blot, qRT-PCR, and immunofluorescence analyses confirmed elevated LSD1 levels in WAT and BAT of Tg compared to control mice (FIG. 1b, and FIG. 7b-d).

Consistent with the appearance of brown or beige adipocytes in WAT of Tg mice, analyses of transcript and protein levels revealed significantly increased expression of Prdm16, Pgc-1α, Ucp1, and several genes involved in oxidative metabolism (FIGS. 1b,c, and FIGS. 7e, and 8). Of note, elevated amounts of LSD1 did not result in altered transcript levels of Prdm16, Pgc-1α, Ucp1, and oxidative markers in BAT and the metabolically active tissues muscle and liver, thus uncovering selective action of LSD1 in WAT (FIG. 9). Importantly, Tg mice expressing a catalytic inactive mutant of LSD1 (Tg$^{Mut}$, FIG. 10a)[36] show normal appearance of WAT, no signs of browning and unaltered expression of Prdm16, Pgc-1α, Ucp1, and oxidative markers (FIG. 1c, and FIGS. 8 and 10b,c), demonstrating that the demethylase activity is essential for the LSD1-induced phenotype.

Next, we screened WAT of Tg mice for the presence of Myf5, a marker of brown adipocyte precursors[20]. Since we did not observe Myf5-positive preadipocytes (FIG. 7e), we hypothesised that the islets emerged from a non-Myf5 lineage and thus might represent beige fat cells. Consequently, we compared the expression pattern of beige, brown, and white fat-selective marker genes in Tg and control mice. The expression of beige fat-selective markers was significantly upregulated in white fat pads of Tg mice (FIG. 1b,d, and FIGS. 7c and 11), whereas no alterations in the metabolically active tissues BAT, muscle, and liver (FIG. 12), or in WAT of Tg$^{Mut}$ mice (FIG. 1d, and FIGS. 10c and 11) were observed. Furthermore, the levels of brown fat-selective, adipogenic, and white fat-selective markers were not altered in WAT of Tg mice (FIG. 1d and FIGS. 6c, 13, and 14). Thus, the gene expression profile identifies the LSD1-induced adipocytes as beige fat cells.

Ultrastructure analyses revealed an increased number of hypotrophic lipid droplets (FIG. 1e), as well as dramatically elevated mitochondria size and number (FIG. 1e,f, and FIG. 15a) in beige adipocytes of Tg mice. These findings were corroborated by an increased ratio between mitochondrial cytochrome C oxidase 2 (Cox2) DNA and nuclear fatty acid synthase (Fasn) DNA (FIG. 15b). In addition, determination of the activities of succinate dehydrogenase (Sdh, mitochondria complex II) and Cox (mitochondria complex IV), two key enzymes of oxidative phosphorylation (OXPHOS), revealed a significantly increased mitochondrial oxidative capacity in WAT of Tg mice (FIG. 1g and FIG. 15c). Together, our observations demonstrate that elevated expression of enzymatically active LSD1 results in the formation of thermogenically active beige fat islets in WAT.

LSD1 Tg Mice Show Limited Weight Gain and Improved Glucose Tolerance and Insulin Sensitivity in Response to a High-Fat Diet To investigate whether the presence of beige fat has physiological consequences, we subjected Tg mice on regular diet (RD) or high-fat diet (HFD) to metabolic analyses. On RD, Tg mice and their control littermates did not display any notable differences in total body weight or in the weight of specific tissues and had a similar food intake (FIG. 16a-c). In contrast, during HFD feeding Tg mice gained significantly less weight (~20%) than their control littermates (FIG. 16d). Body composition analyses assessed by quantitative Nuclear Magnetic Resonance Spectroscopy (qNMR) after 15 weeks of HFD showed that Tg animals had accumulated less fat, resulting in a higher lean/fat mass ratio compared to control mice (FIG. 16e). These data were corroborated by a decreased epWAT mass (FIG. 16f). In accordance, histological analyses revealed adipocyte hypotrophy as well as the presence of beige fat cells and increased Ucp1 levels in Tg mice (FIG. 16g,h). The limited weight gain of Tg mice was not associated with decreased food intake (FIG. 17a) or altered physical activity (FIG. 17b). However, we observed higher energy expenditure (determined by oxygen consumption, $VO_2$) in Tg mice (FIG. 17c). $CO_2$ production ($VCO_2$) was not altered, resulting in a decreased respiratory quotient (RQ, $VCO_2/VO_2$ ratio), demonstrating a shift in fuel consumption from carbohydrate to fatty acid usage (FIG. 17d,e). calorimetric parameters deduced from these analyses indicated that heat production was increased in Tg mice fed a HFD (FIG. 17f). Taken together, these data show that Tg mice are less susceptible to obesity on HFD due to increased energy expenditure.

Diet-induced obesity is frequently associated with glucose intolerance and progressive metabolic dysfunction[37]. Notably, Tg mice on HFD displayed decreased blood glucose levels (FIG. 17g), associated with improved glucose tolerance relative to control mice (FIG. 17h). Tg mice were also more insulin sensitive, as determined by insulin sensitive test (FIG. 17i), showing that Tg mice are more resistant to HFD-induced type-2 diabetes. These effects were not observed in cohorts on RD (FIG. 17j-l). The blood content in triglycerides, free fatty acids (FFA), and cholesterol was not altered in both RD- and HFD-fed animals (FIG. 17g,j). In summary, these observations demonstrate that increased LSD1 levels results in raised energy expenditure, which counteracts HFD-induced obesity and type-2 diabetes associated dysfunction.

LSD1 Levels are Regulated by Environmental Cues

Figure 2:
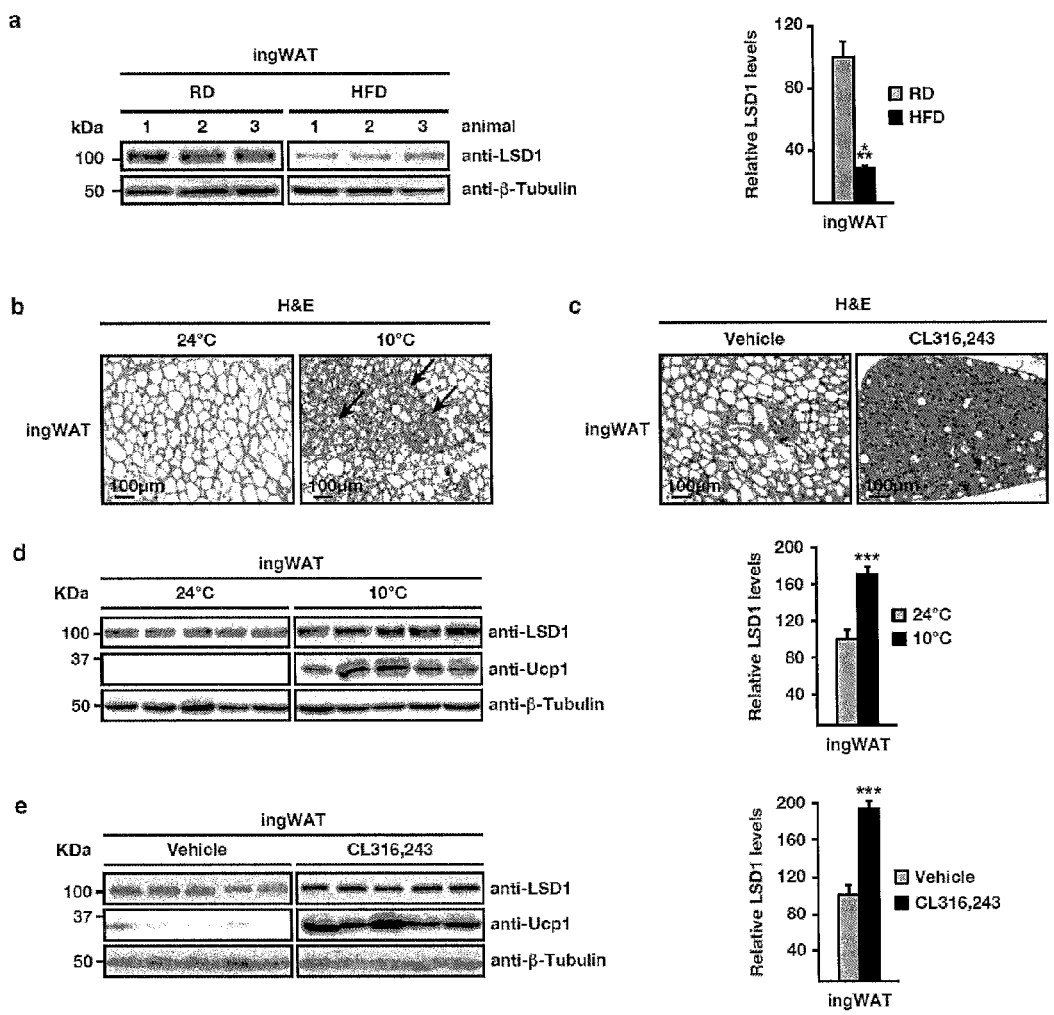
FIG. 2. LSD1 is induced in white fat pads after cold exposure or β3-adrenergic treatment of mice. a, (left panel) Western blot analysis showing LSD1 in ingWAT of mice on regular diet (RD) or high-fat diet (HFD). β-Tubulin was used as a loading control. (right panel) Amount of LSD1 protein relative to β-Tubulin. b, c, H&E staining of ingWAT of mice (b) maintained at either 24 or 10° C., or (c) treated with vehicle or the β3-adrenergic agonist CL316,243. Black arrows show beige fat islets. d, e, (left panels) Western blot analysis of LSD1 and Ucp1 in ingWAT of mice (d) maintained at either 24 or 10° C., or (e) treated with vehicle or CL316,243. β-Tubulin was used as a loading control. (right panels) Amount of LSD1 protein relative to β-Tubulin. Standard deviation represents+SEM (n=10 mice), ***$p<0.001$.

Interestingly, LSD1 protein levels decreased upon HFD in control mice (FIG. 2a), suggesting the existence of regulatory mechanisms controlling physiological amounts of LSD1. Thus, we asked whether other extracellular cues might affect LSD1 levels in wild-type mice. Since cold exposure or treatment of mice with the β3-adrenergic agonist CL316,243 have previously been shown to promote beige fat formation in WAT[19,20,32], we analysed whether protein levels of LSD1 in WAT of mice respond to these stimuli. In both experimental settings, we observed the appearance of multilocular beige adipocytes together with increased LSD1 protein levels in WAT (FIG. 2b-e and FIG. 18a-c), which was not observed in the other metabolically active tissues BAT, muscle, and liver (FIG. 18c). These in vivo data reveal an increase in the amount of LSD1 in WAT as physiological response to environmental challenges such as cold stress or β3-adrenergic stimulation.

Beige Adipogenesis is Impaired in LSD1$^{+/-}$ Mice

Our results suggest that elevated levels of LSD1 initiate a transcriptional cascade that induces the formation of functional beige adipocytes in WAT, which implies that β3-adrenergic signalling should not efficiently induce beige fat islets in mice lacking or expressing reduced levels of endogenous LSD1. Since ubiquitous LSD1-deficient mice die before day E7.5 of embryonic development[3-6], we engineered a conditional LSD1 allele by flanking exon 1 with loxP sites and deleted LSD1 by crossing mice harbouring the conditional allele to the well-described aP2-Cre deleter strain[38], which mediates Cre recombination specifically in WAT and BAT (LSD1$^{aP2-Cre}$, FIG. 19a). Of importance for this study, Cre activity is not restricted to mature adipocytes, but has been observed in white and brown adipocyte precursors[39]. LSD1$^{aP2-Cre}$ mice show a complete absence of white fat pads (FIG. 19b), while BAT is developed, but displays low lipid accumulation (FIG. 19c,d). To demonstrate that the absence of WAT in LSD1$^{aP2\text{-}Cre}$ mice is due to cell autonomy of LSD1, we crossed mice harbouring the conditional LSD1 allele to the Rosa26-CreERT deleter strain[40], which allows tamoxifen (Tx)-inducible Cre recombination (LSD1$^{Rasa26\text{-}CreERT}$). Adipocyte precursors of the stromal-vascular fraction (SVF) from control and LSD1$^{Rosa26\text{-}CreERT}$ mice were isolated, treated with Tx for 5 days, and then induced to undergo adipogenesis. As shown in FIG. 19e,f, LSD1-deficient cells of the SVF neither expressed markers of mature adipocytes nor accumulated lipid droplets, which is accordance with the absence of WAT in LSD1$^{aP2\text{-}Cre}$ mice. While the phenotype of these mice requires more detailed future analyses, a likely explanation for the complete absence of WAT in LSD1$^{aP2\text{-}Cre}$ mice is an essential role of LSD1 in adipocyte differentiation. Together, our data provide in vivo evidence for an essential and cell autonomous function of LSD1 in the control of white adipogenesis.

Figure 3:
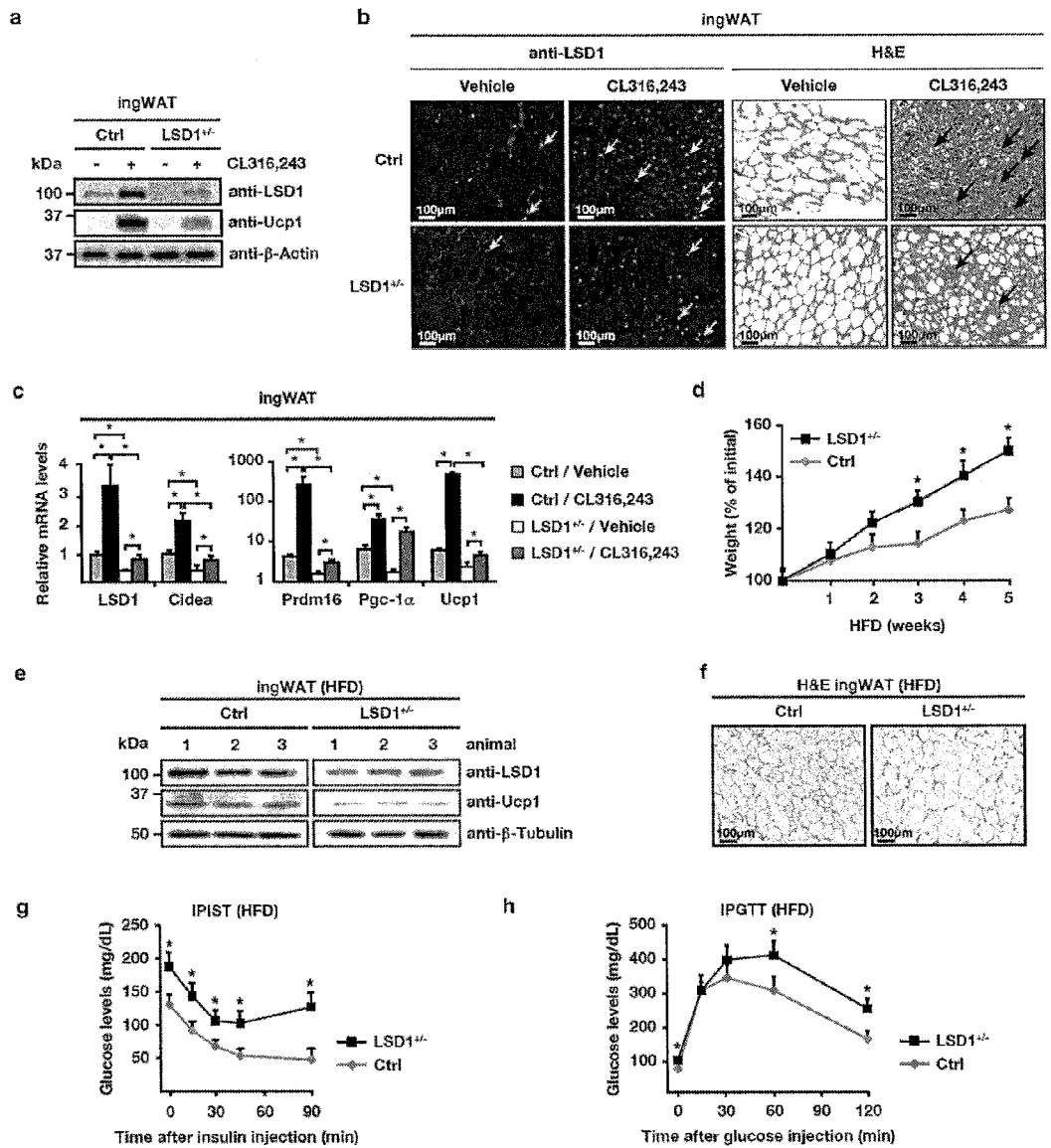
FIG. 3. β3-adrenergic signalling promotes the beige fat programme through LSD1. $LSD1^{+/-}$ mice are prone to obesity and type-2 diabetes due to decreased oxidative capacities in adipose tissue. a, Western blot analysis of LSD1 and Ucp1 in ingWAT of control (Ctrl) and heterozygous LSD1 ($LSD1^{+/-}$) mice treated with vehicle (−) or CL316,243 (+). β-Actin was used as a loading control. b, Immunofluorescent staining of LSD1 (yellow arrows, left panel) and H&E staining (right panel) of ingWAT of Ctrl and $LSD1^{+/-}$ mice treated with vehicle or CL316,243. Black arrows indicate beige fat islets. c, Relative transcript levels of the indicated genes in ingWAT of Ctrl and $LSD1^{+/-}$ mice treated with vehicle or CL316,243. d, Relative body weight of Ctrl and $LSD1^{+/-}$ mice fed a HFD. e, Western blot analysis showing LSD1 and Ucp1 in ingWAT of Ctrl and $LSD1^{+/-}$ mice fed a HFD. β-Tubulin was used as a loading control. f, H&E staining of ingWAT of Ctrl and $LSD1^{+/-}$ mice fed a HFD. g, h, Intraperitoneal insulin sensitive test (g, IPIST), and intraperitoneal glucose tolerance test (h, IPGTT) of Ctrl and $LSD1^{+/-}$ mice fed a HFD. Standard deviation represents+SEM (n=6 mice), *: $p<0.05$.

However, neither ubiquitous nor adipose-specific LSD1 knockout mice were suitable models to validate our hypothesis that β3-adrenergic signalling should not efficiently induce beige fat islets in mice having reduced levels of LSD1. Therefore, we chose heterozygous mice (LSD1$^{+/-}$) (FIG. 20a), in which LSD1 mRNA and protein levels are significantly reduced in WAT and BAT (FIG. 3a-c and FIG. 20b). Compared to control mice, no apparent difference is observed in the morphology of white fat pads of LSD1$^{+/-}$ mice (FIG. 3b and FIG. 20c). Transcript levels of the oxidative markers Cidea, Prdm16, Pgc-1α, and Ucp1 are significantly reduced in fat pads of LSD1$^{+/-}$ mice (FIG. 3c and FIG. 21a), whereas adipogenic and white fat-selective markers are not affected (FIG. 21b,c).

Importantly, treatment of LSD1$^{+/-}$ mice with the β3-selective adrenergic agonist CL316,243 results in fewer clusters of beige fat cells in WAT compared to control mice (FIG. 3b and FIG. 20c). Accordingly, qRT-PCR analyses show that treatment of control mice with CL316,243 significantly increases expression of Cidea, Prdm16, Pgc-1α, and Ucp1 as well as that of beige fat-selective markers in WAT, whereas adrenergic induction is impaired in LSD1$^{+/-}$ mice (FIG. 3c and FIG. 21a,d). In comparison, expression of white fat-selective and adipogenic markers is not significantly affected (FIG. 21b,c). These in vivo results demonstrate that reduction of LSD1 strongly impedes the efficient induction of the beige fat programme by β3-adrenergic signalling, thus establishing LSD1 as an important mediator of this pathway.

LSD1$^{+/-}$ Mice are Prone to Obesity and Type-2 Diabetes

Our data led us to the question whether LSD1$^{+/-}$ mice possess decreased metabolic activities compared to control mice and are prone to obesity and type-2 diabetes when challenged with HFD. Upon HFD, LSD1$^{+/-}$ mice gained substantially more weight than their age-matched control littermates (FIG. 3d) despite similar food intake (FIG. 22a). Consistent with the reduced LSD1 protein levels, Ucp1 protein levels were decreased in LSD1$^{+/-}$ mice (FIG. 3e). qNMR analyses revealed that the body fat content was 16% higher in LSD1$^{+/-}$ mice than in control littermates (FIG. 22b). In agreement with these results, histological analyses revealed adipocyte hypertrophy (FIG. 3f and FIG. 22c). Increased body fat mass was neither due to altered muscle oxidative capacities as shown by assaying NADH dehydrogenase activity in gastrocnemius muscle nor to decreased mobility (FIG. 22d,e). Energy expenditure assessed by oxygen consumption ($VO_2$) (FIG. 23a) as well as $CO_2$ production ($VCO_2$) (FIG. 23b) was decreased in LSD1$^{+/-}$ mice leading to a higher respiratory quotient (RQ) (FIG. 23c). This reveals a shift in fuel consumption from fatty acid to carbohydrate usage. calorimetric parameters deduced from these analyses indicated that heat production was lower in LSD1$^{+/-}$ mice fed a HFD (FIG. 23d). Blood glucose, triglyceride, and free fatty acid (FFA) levels were higher in LSD1$^{+/-}$ than in control mice upon HFD, whereas cholesterol levels were similar (FIG. 23e). Importantly, insulin sensitivity and glucose uptake were significantly reduced in LSD1$^{+/-}$ mice (FIG. 3g,h), indicating that LSD1$^{+/-}$ mice are prone to type-2 diabetes. Of note, we did not observe such alterations in mice fed a RD (FIG. 23f-h). In summary, the in vivo analyses of LSD1$^{+/-}$ mice demonstrate that decreased LSD1 levels lead to altered metabolic capacities resulting in increased susceptibility to obesity and type-2 diabetes.

LSD1 is a Cell-autonomous Regulator of Adipogenesis

To determine whether decreased oxidative capacities observed in WAT of LSD1$^{+/-}$ mice are due to cell-autonomous dysfunctions of the fat tissue, we analysed adipocyte precursors from the SVF of LSD1$^{+/-}$ and control mice. Upon differentiation, primary adipocytes from LSD1$^{+/-}$ mice carried increased lipid content compared to control (FIG. 24a). In accordance with this observation, LSD1$^{+/-}$ adipocytes expressed increased levels of general adipogenic and white fat-selective markers (FIG. 24b) and expression of genes involved in thermogenesis, including Prdm16 and Ucp1 was reduced in LSD1$^{+/-}$ adipocytes (FIG. 24b).

Figure 4:
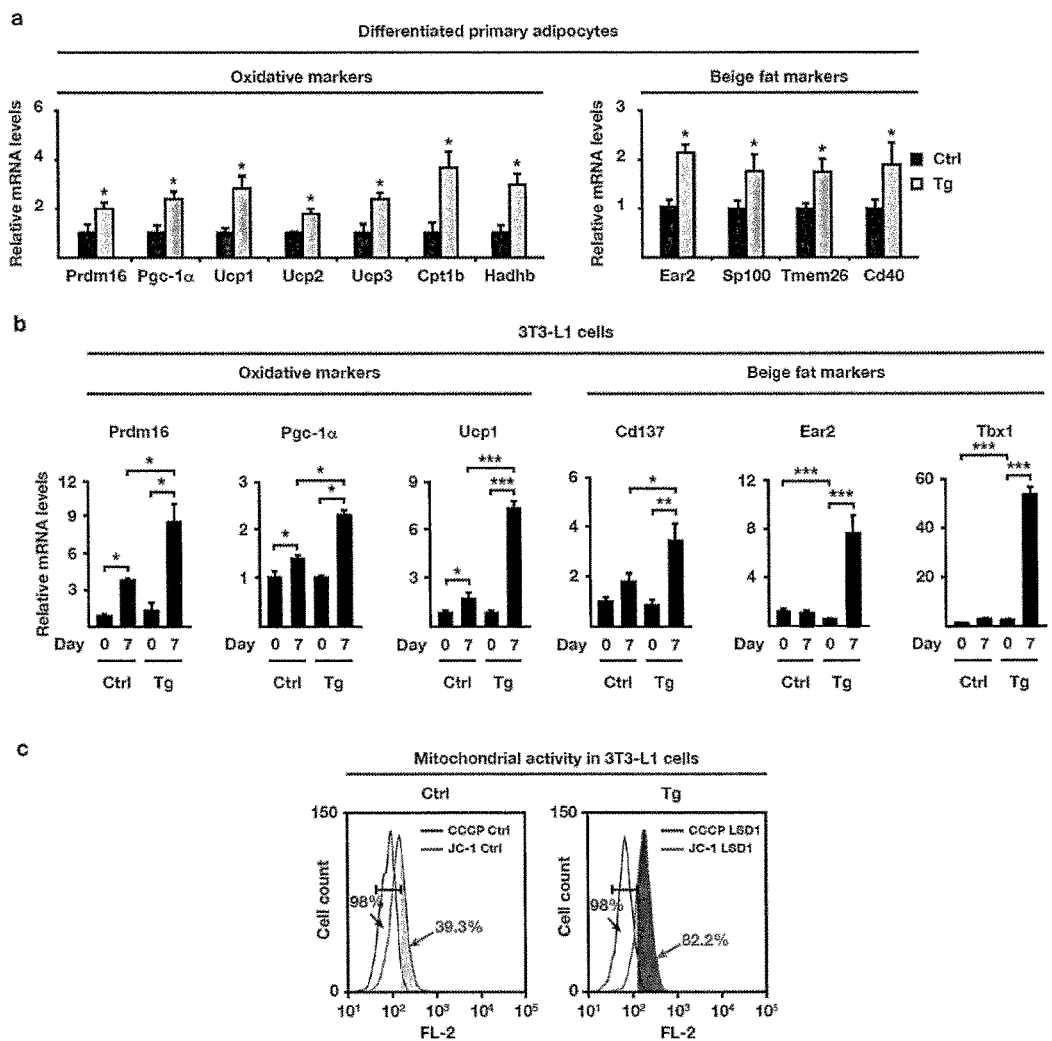
FIG. 4. LSD1 promotes the formation of functional beige adipocytes in vitro. a, Relative transcript levels of the indicated oxidative and beige fat-selective markers in in vitro differentiated primary adipocytes isolated from stromal-vascular fraction of control (Ctrl) and LSD1 transgenic (Tg) mice. b, Relative transcript levels of the indicated oxidative and beige fat-selective markers in undifferentiated (day 0) and differentiated (day 7) control (Ctrl) and LSD1 overexpressing (Tg) 3T3-L1 cells. c, Mitochondrial activity in 3T3-L1(Ctrl) and 3T3-L1(Tg) cells at day 7 reflected by red fluorescent JC-1 aggregates (FL-2). Black curves represent the background staining (CCCP). Numbers in red show the percentage of cells with increased mitochondrial activity. Standard deviation represents+SEM (n=6), *p<0.05, ***p<0.001.

Similarly, to investigate cell autonomy of beige fat formation in Tg mice, adipocyte precursors from the SVF of Tg and control mice were induced to undergo adipogenesis. Tg and control adipocyte cultures expressed equivalent levels of general adipogenic, white fat-selective, and brown fat-selective markers (FIG. 24c). In contrast, elevated levels of LSD1 in primary Tg adipocyte induced expression of genes involved in oxidative metabolism, including Prdm16, Pgc-1α, and Ucp1, and beige fat-selective markers (FIG. 4a). Taken together, these data demonstrate that LSD1 regulates oxidative capacities of adipocytes and beige adipogenesis in a cell-autonomous manner.

To establish a cell culture model for mechanistic studies, we transduced C3H-10T1/2 mouse mesenchymal cells and 3T3-L1 preadipocytes with lentivirus driving constitutive expression of LSD1 (Tg), LSD1 inactive mutant (Tg$^{Mut}$), or empty control virus (Ctrl) (FIG. 25a,b). Expression levels of genes involved in oxidative metabolism such as Prdm16, Pgc-1α, and Ucp1 and of beige fat-selective markers were increased upon differentiation of 3T3-L1(Tg) and C3H-10T1/2(Tg) compared to Ctrl cells (FIG. 4b and FIG. 25b,c). Vice versa, both Tg cell lines showed slightly decreased transcript levels of white adipocyte-selective markers and similar transcript levels of general adipogenic markers (FIG. 25d,e). In agreement with the in vivo data, oxidative and beige fat-selective markers were not altered in C3H-10T1/2(Tg$^{Mut}$)-derived adipocytes expressing the catalytically inactive LSD1 mutant (FIG. 25b).

Analysis of the oxidative capacities of differentiated 3T3-L1(Tg) and 3T3-L1(Ctrl) cells by staining with the fluorescent dye JC-1 revealed that 3T3-L1(Tg) cells exhibit a significantly increased respiratory activity indicated by red fluorescence (FIG. 4c and FIG. 26a). More intense green fluorescence revealed an augmentation in mitochondrial mass (FIG. 26b). The increased ratio between red and green fluorescence (FL-2/FL-1) in adipocytes derived from 3T3-L1(Tg) cells demonstrated an enhanced mitochondrial activity (FIG. 26c). Thus, consistent with our observations in mice and primary adipocytes from the SVF, increased LSD1 expression suffices to induce the beige fat programme in vitro. Consequently, we used 3T3-L1 and C3H-10T1/2 cells for further mechanistic studies.

To determine whether LSD1 promotes the beige fat programme via commitment of white adipocyte precursors or transdifferentiation of mature adipocytes, we transduced 3T3-L1 cells with lentivirus driving doxycyclin-inducible expression of LSD1 (LSD1$^{Ind}$). LSD1 expression was induced at days 3 or 7 of differentiation. While we observed a strong increase in LSD1 levels upon doxycyclin treatment (FIG. 27a), transcript levels of oxidative markers such as Prdm16, Pgc-1α, and Ucp1, adipogenic, white fat-selective, and beige fat-selective markers (FIG. 27) were not affected by LSD1 induction. These data show that LSD1 does not induce the beige fat programme once adipogenesis has been initiated. Thus, LSD1 appears to act at an early time point by triggering the commitment of adipocyte precursors towards the beige lineage.

LSD1 Targets Genes that Induce the Beige Fat Programme and Account for Beige Adipocyte Metabolism Beige adipogenesis requires induction of adipogenic factors and activation of specific gene sets facilitating thermogenesis and energy consumption. To identify LSD1 direct target genes that mediate induction of the beige fat programme and account for beige adipocyte metabolism, we combined chromatin immunoprecipitation followed by massive parallel sequencing (ChIP-seq) and global transcriptome analysis (RNA-seq) of 3T3-L1(Tg) and 3T3-L1(Ctrl) cells at days 0 and 7 of differentiation.

In ChIP-seq analyses, 3024 high-confidence LSD1 peaks [false discovery rate (FDR) less than 1%] were identified at day 0 in 3T3-L1(Ctrl) cells, with the majority (87%) located at the promoter (defined as ±2000 bp around the transcription start site) of 2607 genes (FIG. 5a and FIG. 28a). At day 7, we identified 8303 LSD1 peaks, of which 85% are located at the promoter of 6904 genes (FIG. 5a and FIG. 28b). In 3T3-L1(Tg) cells, the number of LSD1 peaks at day 0 reached 13997, with 60% located at the promoter of 8145 genes (FIG. 5b and FIG. 28a), while at day 7, 27221 LSD1 peaks were identified with 43% located at the promoter of 9840 genes (FIG. 5b and FIG. 28b).

The comparison of genes with LSD1 promoter occupancy in 3T3L1(Ctrl) cells showed that the vast majority [2233 out of 2607 (86%)] of genes bound at day 0 is still occupied at day 7 (FIG. 5c). On the other hand, 4671 out of 6904 genes (68%) are associated with LSD1 at day 7 only. Importantly, the comparison with 3T3-L1(Tg) cells revealed that most of the genes occupied in 3T3-L1(Ctrl) cells at day 7 are already associated with LSD1 in 3T3-L1(Tg) cells at day 0 [5689 out of 6904 genes (82%)] (FIG. 5d). Thus, promoter occupancy by LSD1 in undifferentiated 3T3-L1(Tg) cells at day 0 resembles that in differentiated 3T3-L1(Ctrl) cells at day 7.

Next, we established differential gene expression patterns for 3T3-L1(Tg) and 3T3-L1(Ctrl) cells at days 0 and 7 of differentiation. At day 0, our RNA-seq analyses revealed 1929 genes differentially expressed between 3T3-L1(Tg) and 3T3-L1(Ctrl) cells (FIG. 5e) [p-value<10$^{-5}$ and logarithm base 2 of fold change (FC)<0.7 or >1.4]. Out of these, 1068 genes were found in the intersection between differentially expressed and LSD1-occupied genes in 3T3-L1(Tg) cells at day 0 (FIG. 5e). Pathway analyses for the 1929 differentially expressed and the 1068 genes in the intersection revealed "adipogenesis" as significantly enriched cluster (FIG. 28c). While 3T3-L1(Tg) cells might be committed to become beige adipocytes due to these differentially expressed genes, they are apparently not sufficient to induce adipocyte maturation, for which additional adipogenic stimuli are required.

At day 7, the number of genes differentially expressed between 3T3-L1(Tg) and 3T3-L1(Ctrl) cells increases to 5765 (FIG. 5f). In the intersection between these differentially expressed and LSD1-occupied genes in 3T3-L1(Tg) cells, 4091 genes were found. Importantly, pathway analyses for the 5765 differentially expressed and the 4091 intersection genes unravelled the major metabolic pathways "electron transport chain", "oxidative phosphorylation", "tricarboxylic acid (TCA) cycle", "glycolysis and gluconeogenesis", and "fatty acid beta oxidation" in addition to "adipogenesis" (FIG. 28d,e). Furthermore, the intersection between LSD1 promoter occupancy in 3T3-L1(Ctrl) cells at day 7, 3T3-L1(Tg) cells at day 0, and differentially expressed genes at day 7 revealed that 2406 genes with premature promoter occupancy at day 0 are indeed deregulated in differentiated 3T3-L1(Tg) cells (FIG. 28f). Pathway analyses confirmed that these genes account for metabolic properties of 3T3-L1(Tg) cells (FIG. 28g). Together, we conclude that increased LSD1 levels result in premature chromatin occupancy, which upon adipogenic stimuli causes deregulated gene expression accounting for differentiation and metabolic properties of beige adipocytes.

A detailed inspection of the identified metabolic pathways uncovered that in 3T3-L1(Tg) cells LSD1 occupies and positively regulates the expression of most genes involved in oxidative phosphorylation (84/92 genes), TCA cycle (10/12 genes)$^{41}$, fatty acid β-oxidation (¾ rate limiting Cpt enzymes, and 22/35 genes of (3-oxidation), and glycolysis (17/21 genes) (FIG. 29a and Table 1). Consistently, expression of representatives of these pathways is increased in C3H-10T1/2(Tg) and 3T3-L1(Tg) cells and in beige fat of Tg mice in vivo (FIGS. 8, 25b,c, and 29b-d).

Next, we asked whether known upstream regulators of the identified metabolic pathways are also targeted by LSD1. A central player in the initiation of signalling events is AMP kinase (Ampk, also referred to as Prka) (schematically depicted in FIG. 30a). Active Ampk phosphorylates Acaca, which in turn activates Cpt1, the rate-limiting enzyme of (3-oxidation, and positively regulates Pgc-1α expression. Pgc-1α and Pgc-1β act as key regulators of oxidative metabolism, promoting 8-oxidation, glycolysis, and TCA cycle. Pgc-1α also serves as a coactivator for Nrf1, a key player in the transcriptional control of nuclear genes required for respiration, mitochondrial DNA transcription and replication via Tfam. Importantly, in 3T3-L1(Tg) cells LSD1 is present at the promoter of 90% of Ampk subunits (Table 1), as well as at the promoter of Acaca, Pgc-1α, Pgc-1β, Nrf1, and Tfam (FIG. 30b). In all cases, our RNA-seq results and independent qRT-PCR analyses showed that expression of these genes is increased in 3T3-L1(Tg) compared to 3T3-L1(Ctrl) cells at day 7 (FIG. 4b and FIGS. 25c, 30b, and 31a,b,d) as well as in beige fat of Tg mice (FIGS. 1c, 4a and FIGS. 8, 31a,c,d). Furthermore, LSD1 occupies and positively regulates the genes required for uncoupled respiration (Ucp2 and Ucp3) (FIG. 31e), which contributes to increased heat production by mitochondria. Taken together, our ChIP-seq, RNA-seq, and qRT-PCR analyses demonstrate that increased LSD1 levels regulate gene programmes essential for mitochondrial biogenesis and metabolic pathways thereby accounting, at least in part for, the phenotype of 3T3-L1(Tg) cells in vitro and beige adipocytes of Tg mice in vivo.

TABLE 1

Regulation of metabolic pathways by LSD1. Pathway, total number of genes encoding pathway proteins, promoter occupancy by LSD1 in 3T3-L1(Ctrl) and 3T3-L1(Tg) cells at day 0, and average logarithmic fold change (FC) of differential gene expression between 3T3-L1(Tg) and 3T3-L1(Ctrl) cells at day 7 of differentiation.

| Pathway | Total genes | Gene promoters occupied by LSD1 | | Average FC day 7 |
|---|---|---|---|---|
| | | 3T3-L1(Ctrl) cells day 0 | 3T3-L1(Tg) cells day 0 | |
| Ampk (Prka) sub-units | 8 | 3 (37.5%) | 7 (87.5%) | 2.0 |
| β-oxidation | 35 | 7 (20.0%) | 22 (62.9%) | 2.7 |
| Glycolysis | 21 | 5 (23.8%) | 17 (81.0%) | 2.1 |
| TCA cycle | 12 | 2 (16.7%) | 10 (83.3%) | 2.6 |
| Complex I | 41 | 9 (22.0%) | 38 (92.7%) | 2.9 |
| Complex II | 4 | 1 (25.0%) | 3 (75.0%) | 2.9 |
| Complex III | 9 | 2 (22.2%) | 9 (100.%) | 3.3 |
| Complex IV | 21 | 6 (28.6%) | 18 (85.7%) | 2.4 |
| Complex V | 17 | 3 (17.6%) | 16 (94.1%) | 2.4 |
| OXPHOS (Complexes I-V) | 92 | 21 (22.8%) | 84 (91.3%) | 2.7 |

LSD1 Regulates Mitochondrial Functions Through Nrf1

To identify transcription factors that cooperate with LSD1 in the control of beige adipogenesis and beige adipocyte metabolism, we performed HOMER motif searches[42]. These analyses revealed that in 3T3-L1(Ctrl) cells at day 7 and in 3T3-L1(Tg) cells at days 0 and 7 promoter occupancy of LSD1 significantly correlates with the presence of binding sites for the transcription factor Nrf1 (FIG. 6a). To investigate whether LSD1 and Nrf1 coordinately control gene expression, we first established by ChIP-seq the genome-wide binding pattern of Nrf1 in 3T3-L1 cells at days 0 and 7 of differentiation. At day 0, we identified 2078 peaks (FIG. 6b), with the majority (67%) found at the promoter of 1383 genes (FIG. 6c). At day 7, 1629 Nrf1 peaks were observed (FIG. 6b) with 91% located at the promoter of 1485 genes (FIG. 6c). 914 genes with Nrf1 peaks at the promoter were found in the intersection between days 0 and 7 (FIG. 6c). Whereas only 427 out of 1383 (31%) gene promoters bound by Nrf1 are cooccupied by LSD1 at day 0 (FIG. 6d), the majority (1178 out of 1485, 79%) is bound by LSD1 at day 7 (FIG. 6d). The intersection of genes occupied by Nrf1 at days 0 and 7, and LSD1 at day 7 revealed a robust overlap, i.e. 736 out of 914 (81%) genes (FIG. 6e). This finding suggests that LSD1 and Nrf1 coordinately control gene expression during 3T3-L1 cell differentiation. Pathway analyses for this common gene set (736 genes) revealed "electron transport chain" and "oxidative phosphorylation" among the top scoring clusters as exemplified by components of the mitochondrial electron transport chain (FIG. 32). Of note, we also identified the Nrf1 gene among the prominent LSD1 targets (FIG. 30b). RNA-seq, qRT-PCR, and Western blot analyses showed increased Nrf1 transcript and protein levels in differentiated 3T3-L1(Tg) cells and beige fat of Tg mice (FIGS. 31a-c). In contrast, Nrf1 levels were not altered in skeletal muscle and liver of Tg mice (FIG. 33). Short interfering RNA (siRNA)-mediated knockdown of Nrf1 in 3T3-L1(Tg) cells significantly decreased expression of Prdm16, Pgc-1α, and Ucp1, as well as representative genes of the mitochondrial electron transport chain (FIG. 34). Together, these data suggest that LSD1 promotes mitochondrial respiratory properties of fat cells, at least in part, by induction of and in cooperation with Nrf1.

LSD1 Regulates Beige Adipogenesis Through C/Ebpβ and Pparγ/Rxrα

HOMER motif searches revealed a significant enrichment of C/ebpβ, Pparγ, and Rxr binding sites for 3T3-L1(Tg) cells at day 7, whereas for 3T3-L1(Ctrl) cells these binding sites were not identified among the top scoring motifs (FIG. 6a). Since C/ebpβ and Pparγ, in cooperation with Prdm16 or Pgc-1α, have been shown to promote the browning of fat cells[16,20], this observation suggested that in 3T3-L1(Tg) cells LSD1 acts in cooperation with C/ebpβ and Pparγ/Rxrα to regulate early and late phases of beige adipogenesis, respectively. Indeed, previously reported C/ebpβ ChIP-seq data[43] from 3T3-L1 cells illustrated that at day 0, 729 out of 3285 (22%) of C/ebpβ target genes are cooccupied by LSD1 (FIG. 35a), whereas at day 3, 2034 out of 3287 (62%) of C/ebpβ targets are cooccupied by both proteins (FIG. 6f). Pathway analyses of the common target genes at day 3 of differentiation suggested that LSD1 and C/ebpβ control adipogenesis as well as main metabolic pathways (FIG. 35b). As shown by ChIP-seq and RNA-seq analyses, C/ebpα, C/ebpβ, and C/ebpδ are direct LSD1 target genes, and LSD1 upregulates expression of C/ebpa at day 7, and C/ebpβ at days 0 and 7 of 3T3-L1 cell differentiation (FIG. 35c). These data were corroborated in both, differentiated 3T3-L1(Tg) cells and beige fat of Tg mice (FIG. 35d-f). In contrast, C/ebp transcript levels were neither altered in skeletal muscle nor in liver of Tg mice (FIG. 33). Finally, RNAi-mediated knockdown of C/ebpβ in 3T3-L1(Tg) cells significantly decreased expression of the beige-selective gene programme (FIG. 36) demonstrating that C/ebpβ, at least in part, mediates LSD1-controlled beige adipogenesis.

C/ebpβ and C/ebp6 also promote expression of Pparγ[44]. Pparγ/Rxr heterodimers act as a transcriptional activator of numerous adipocyte-specific genes[45]. ChIP-seq analysis of Pparγ and Rxrα in 3T3-L1 cells[46] confirmed that at day 0 only a minimal fraction (0.5%) of LSD1 target genes is cooccupied by Pparγ/Rxrα (FIG. 37a). However, at day 7, Pparγ/Rxrα occupy 1831 out of 6904 (27%) of LSD1 target genes (FIG. 6g). These 1831 common target genes define "adipogenesis" (FIG. 37b) in addition to the main metabolic pathway clusters, as exemplified by representative genes of fatty acid β-oxidation (FIG. 37c), demonstrating that LSD1 in concert with Pparγ/Rxrα controls late adipogenesis. Furthermore, LSD1 binds to the Pparγ and Rxrα gene promoter (FIG. 38a) and induces expression of Pparγ and Rxrα in 3T3-L1(Tg) cells and beige fat of Tg mice (FIG. 38b-d).

In summary, our data show that LSD1 controls beige adipogenesis by increasing mitochondrial biogenesis and respiration via Nrf1, inducing early adipogenesis through C/ebpβ, and enforcing late adipogenesis by Pparγ/Rxr (FIG. 39).

Methods

Mouse Studies

All mice were housed in the pathogen-free barrier facility of the University Medical Center Freiburg in accordance with institutional guidelines and approved by the regional board. Mice were maintained in a temperature- and humidity-controlled animal facility with a 12-hour light/dark cycle, free access to water, and a standard rodent chow (Kliba, breeding, 3807). The high-fat diet (HFD) study was carried out with a chow containing 4.056 kcal/kg (fat: 1.600 kcal/kg and sucrose: 1.600 kcal/kg; Research Diets). HFD was given to mice at 5 weeks of age. Mice were analysed at 25 weeks of age. For cold exposure experiments, mice were maintained at 10° C. with a 12 hour light/dark cycle, free access to water, and a standard rodent chow. Animals were killed by cervical dislocation, tissues were immediately collected, weighted, frozen in liquid nitrogen or processed for further analyses. Nomenclature for dissected adipose depots was used according to Seale et al.[17]. Epididymidal WAT (epWAT): prominent bilateral intra-abdominal visceral depots in male mice attached to the epididymis. Inguinal WAT (ingWAT): bilateral superficial inguinal depots between the skin and muscle fascia just anterior to the lower segment of the hind limbs. Perimuscular WAT (pmWAT): depots located on the upper part of the quadriceps muscle. Retroperitoneal WAT (rpWAT): bilateral depots in abdominal cavity behind the peritoneum on the dorsal side of the kidney. Interscapular BAT (BAT): most prominent depot of brown adipocytes in rodents, found between the scapulae. In vivo experiments including food consumption, serum analysis, glucose tolerance and insulin sensitivity tests, temperature measurements, body lean and fat contents, and energy expenditure were described[48]. CL316,243 (Sigma-Aldrich) was injected intraperitoneally at 1 mg/kg.

Generation of Rosa26-LSD1 and Rosa26-LSD1 Inactive Mutant Transgenic Mice

To generate transgenic (Tg) mice or inactive mutant transgenic ($Tg^{Mut}$) mice, the complete human wild type or K661A/W751A/Y761S mutated LSD1 cDNA was cloned 3' to the Rosa26 promoter/enhancer (FIGS. 7a and 10a, respectively). Tg and $Tg^{Mut}$ mice were generated by pronuclear injection into fertilized FVB oocytes. For analyses wild-type littermates were used as controls. Mice were genotyped by PCR amplification of genomic DNA extracted from tail biopsies using the DirectPCR extraction kit (Viagen) with primers for detection of the transgene Rosa26-LSD1 or Rosa26-LSD1$^{Mut}$ (Table 2).

TABLE 2

Primers used for genotyping

| Gene | Sense | Primer 5'-3' |
|---|---|---|
| Rosa26-LSD1 | fw | AATGCCTTCGAATTCAGCAC |
| Rosa26-LSD1 | rev | CCTTGTCATCGTCGTCCTTG |
| Rosa26-LSD1$^{Mut}$ | fw | TCTTCTTTGCGGGAGAACAT |
| Rosa26-LSD1$^{Mut}$ | rev | CGCCTCTAGCTCACATGCTT |
| LSD1 WT/L2 | fw | CCTCAGTAGGCCTGGTTTGT |
| LSD1 WT/L2 | rev | TTGGTTTTGGTTGACCCTTC |
| LSD1 L- | fw | CCGTGGAAATTCGTGCACTC |
| LSD1 L- | rev | GCAGGCGGTTTGAAATGTATTC |
| Cre | fw | TTCCCGCAGAACCTGAAGATGTTCG |
| Cre | rev | GGGTGTTATAAGCAATCCCCAGAAATGC |

Generation of Conditional LSD1 Mice

The targeting strategy for the conditional deletion of the first exon of LSD1 (LSD1$^{tm1Schüle}$) is available upon request. To delete LSD1, conditional LSD1 mice were crossed to either Rosa26-Cre$^{(Tg/0)}$ transgenic mice that ubiquitously express the Cre recombinase (FIG. 20a), aP2-Cre mice[38] to selectively ablate LSD1 in adipose tissue, or Rosa26-CreERT$^{(Tg/0)}$ transgenic mice, which mediates tamoxifen-inducible Cre recombination (LsD1$^{Rosa26-CreERT}$)[40]. Mice were maintained on a mixed C57/Bl6NCrl; 129S2/Sv background. Homozygous conditional mice were used as controls. Mice were genotyped with primers for detection of the conditional LSD1 and the deleted alleles (Table 2).

Analysis of Mitochondrial Activity

Tissues obtained from mice were immediately frozen in liquid nitrogen. The activities of the respiratory chain enzyme complex II (Sdh) and complex IV (Cox) were determined as described[50].

Food Consumption

Mice were individually housed. Food pellets (150 g) were delivered and weighed after 1 week. Weekly food consumption was calculated by subtracting the final from the initial pellet weight.

Serum Analysis

Blood was collected from retro orbital sinus after a 6 hr fast that started at the beginning of the light cycle. Serum glucose, cholesterol, triglyceride, and free fatty acid levels were analysed as described[51].

Glucose Tolerance and Insulin Sensitivity Tests

Intraperitoneal glucose tolerance test (IPGTT) and insulin sensitivity test (IPIST) were performed with mice fed a RD or a HFD after 6 h or 16 h of fasting, respectively. For IPGTT, following measurement of the basal glucose level (time 0), mice were intraperitoneally injected with 20% glucose in sterile saline solution (0.9% NaCl) at a dose of 2 g glucose/kg body weight. Blood was collected from the tail vein after 15, 30, 45, 60, 90, and 120 min for glucose determination. For IPIST, mice were intraperitoneally injected with porcine insulin (0.5 U/kg; Sigma). Blood was collected at 15, 30, 60, and 90 min.

Body Lean and Fat Content

Body lean and fat content were recorded in anaesthetized mice by quantitative nuclear magnetic resonance (qNMR, PIXIMUS, GE Medical Systems) according to the manufacturer's instructions.

Energy Expenditure

Total activity, oxygen consumption ($O_2$) and carbon dioxide ($CO_2$) production were measured with a LabMaster (TSE systems) at 26 min intervals for 24 h. $VO_2$ and $VCO_2$ values were normalized to body mass. The respiratory quotient (RQ) corresponds to $VCO_2/VO_2$. Heat (Cal/h) was calculated using the formula: Heat (H)=(Caloric Value× $VO_2$×0.001)/body weight×0.75; (Caloric Value=3.815+

1.232×RQ). Body temperature was measured with a rectal probe linked to a digital thermometer (Bioseb).

Histological and Immunofluorescence Analysis

Tissues were fixed in 10% buffered formalin and embedded in paraffin. For immunofluorescence analyses, 5 µm paraffin sections were deparaffinised, rehydrated, boiled in antigen unmasking solution (Vector laboratories, H-3300) for 10 min, cooled to room temperature, washed 3 times with PBS, 0.1% Triton-X100 for 5 min, incubated for 1 h in 5% FBS (Gibco, 10270-106) in PBS, 0.1% Triton-X100, followed by overnight incubation at 4° C. with anti-LSD1[1] (1/1000), anti-Myf5 (Santa Cruz, C-20, sc-302, 1/500), anti-Prdm16 (abcam, ab118573, 1/500), or anti-Ucp1 (abcam, ab10983, 1/200) antibody. Slides were then incubated with secondary antibody conjugated to Alexa546 (Invitrogen, 1/400) and mounted in aqueous medium (Fluoromount-G, SouthernBiotech, 0100-01) with DAPI (Sigma, D-9542, 1/1000). Between each step, sections were washed with PBS, 0.1% Triton-X100.

For NADH-tetrazolium reductase activity staining, 10 µm cryosections were incubated in 0.2 M Tris-HCl pH 7.4, containing 1.5 mM NADH (Roche) and 1.5 mM nitrobluetetrazolium (Sigma) for 15 min at 55° C., dehydrated, and mounted[52].

For ultrastructural analyses samples were fixed by immersion in 2.5% glutaraldehyde and 2.5% paraformaldehyde in cacodylate buffer (0.1 M, pH 7.4), washed in cacodylate buffer for 30 min and kept at 4° C. Post-fixation was performed with 1% osmium tetraoxide in 0.1 M cacodylate buffer for 1 h at 4° C. and dehydration through graded alcohol (50, 70, 90 and 100%) and propylene oxide for 30 min each. Samples were embedded in Epon 812. Ultrathin sections were cut at 70 nm and contrasted with uranyl acetate and lead citrate and examined at 70 kV with a Morgagni 268D electron microscope. Images were captured digitally by a Mega View III camera (Soft Imaging System). Mitochondria number and cross section areas were determined with the Image J software (NIH).

RNA Preparation and Analysis

RNA was isolated with TRIzol Reagent (Invitrogen). Two micrograms of RNA were converted to cDNA with SuperScript II reverse transcriptase (Invitrogen) and polyT oligonucleotides according to the supplier's protocol. Quantitative RT-PCR was performed using the Abgene SYBR Green PCR kit (Invitrogen) according to the supplier's protocol. Data were analysed using the standard curve method[53]. 36b4, Hprt, Tbp, or β-actin were used for normalization. Primer sequences are given in Table 3.

RNA Sequencing (RNA-Seq)

RNA samples were sequenced by the standard Illumina protocol to create raw sequence files (.fastq files). We aligned these reads to the mm10 build of the mouse genome using TopHat version 2[54]. The aligned reads were counted with the homer software (analyze RNA) and DEG's were identified using EdgeR[55] and DESeq version 1.8.3[56].

Protein Preparation, Western Blot Analysis, and Coimmunoprecipitation Assays

Experiments were performed as described[1]. Fat tissues were grounded in RIPA buffer [50 mM Tris pH 7.5, 1% NP40, 0.5% sodium deoxycholate, 0.1% SDS, 150 mM NaCl, 5 mM EDTA, and protease inhibitor cocktail (45 µg/ml, Roche, 11 873 580 001)] at 4° C.

Homogenates were separated in 10% polyacrylamide gels and blotted to Hybond nitrocellulose membranes (GE Healthcare). Membranes were decorated using following antibodies: anti-LSD1[1] (1/1000), anti-Prdm16 (abcam, ab118573, 1/500), anti-Pgc-1 (Santa-Cruz, H300, sc-13067, 1/1000), anti-Nrf1 (abcam, ab55744, 1/1000), anti-Ucp1 (abcam, ab10983, 1/1000), anti-Klhl13 (Santa-Cruz, H-286, sc-99119, 1/500), Fabp4 (Santa-Cruz, sc-18661, 1/2000), anti-Flag (Sigma, F3165, 1/500), anti-Ear2 (Proteintech, 60117-2-Ig, 1/400), anti-C/ebpβ (Santa-Cruz, sc-746, 1/500), anti-Ppary (AbD Serotec, AHP1461, 1/500), anti-Rxrα (Santa-Cruz, sc-553, 1/500), anti-β-Tubulin (Sigma, T6074, 1/10000), or anti-β-Actin (Sigma, A1978, 1/10000). Secondary antibodies conjugated to horseradish peroxidase (GE Healthcare) were detected using an enhanced chemiluminescence detection system (GE Healthcare). Protein levels were quantified using the Chemi Capt software (Peqlab).

ChIP Sequencing (ChIP-seq)

Chromatin immunoprecipitation experiments were performed using anti-LSD1 (20752, Schüle laboratory) or anti-Nrf1 (abcam, ab55744, lot GR 95770-1) antibodies, on protein A-Sepharose 4B (GE Healthcare) essentially as described[57]. Libraries were prepared from immunoprecipitated DNA according to standard methods. ChIP-seq libraries were sequenced using a HiSeq 2000 (Illumina) and mapped to the mm10 reference genome using bowtie 2[58]. Data were further analysed using the peak finding algorithm MACS 1.41[59] using input as control. All peaks with FDR greater than 1% were excluded from further analysis. The uniquely mapped reads were used to generate the genome-wide intensity profiles, which were visualized using the IGV genome browser[60]. HOMER[42] was used to annotate peaks, to calculate overlaps between different peak files, and for motif searches. The genomic features (promoter, exon, intron, 3' UTR, and intergenic regions) were defined and calculated using Refseq and HOMER. Genes annotated by HOMER were further used for a pathway analysis[42]. Previously reported ChIP-seq results for C/ebpβ (GSE27826)[43], Pparγ, and Rxrα (GSE13511)[46] were used for analysis.

Quantification of Mitochondrial and Nuclear DNA

Fat pads were digested overnight with Proteinase K and DNA was extracted with phenol-chloroform. Mitochondrial and nuclear DNA was amplified by quantitative PCR using Cox2 and Fasn primers (Table 3), respectively.

Plasmids

The following plasmids were used: pLenti4_Flag_HA_Puro, pLenti4_Flag_HA_Puro_LSD1, pRTS_Puro_GW, pRTS_Puro_GW-Flag_LSD1, pRTS_Puro_GW-Flag_LSD1-K661A-W751A-Y761S, pSlik-Neo, and pSlik-Neo_Flag-HA_LSD1. Plasmids were obtained by Gateway LRII cloning in pLenti4 vector (Invitrogen) or in a puromycin-selectable and doxycycline-inducible pRTS plasmid[61] modified to contain a Gateway cassette, V5, and His tags. Cloning details can be obtained upon request.

Cell Culture

Primary white fat stromal vascular and mature fat cells were fractionated according to published methods[62,63]. Primary SV cells were cultured in DMEM/F12 containing 10% fetal bovine serum (FBS). For induction of CreERT recombinase, primary cells were treated with 4-hydroxy-tamoxifen (Sigma) at 0.2 µM. Mouse 3T3-L1 and C3H-10T1/2 pre-adipocytes were maintained in Dulbecco's modified Eagle's medium (DMEM) or Eagle's minimal essential medium (EMEM), respectively, supplemented with 10% FBS and glutamine. Differentiation of primary SV cells, 3T3-L1, and C3H-10T1/2 was induced by treatment of confluent cells (designated day 0) with an adipogenic mixture consisting of 10 µg/ml insulin (Gibco), 1 µM dexamethasone (Calbiochem), 10 µM rosiglitazone (Cayman) and 500 µM isobutylmethylxanthine (Serva) in the presence of 10% FBS. The differentiation medium was replaced 3 days later (day 3)

with medium supplemented with 10% FBS and 10 µg/ml insulin for 2 days. Subsequently, the cells were cultured in the same medium for 2 more days (day 7). For the determination of mitochondrial metabolism 3T3-L1 cells were stained with fluorescent dye JC-1 (Invitrogen) followed by flow cytometric analysis. Following trypsin treatment, cells were exposed to 20 µg/ml of JC-1 in culture medium for 15 min at 37° C. and suspended in PBS for fluorescence-activated cell sorting (FACS) analysis. Green and red fluorescent signals corresponding to mitochondrial mass (FL-1) and mitochondrial membrane potential (FL-2), respectively, were detected using a FACS Canto cytometer (Becton Dickinson). 293FT cells were cultured in DMEM supplemented with 10% FBS, non-essential amino-acids (Gibco) and glutamine (Gibco). Viral production was performed as described[1]. 3T3-L1 cells were infected with pLenti4_Flag_HA_Puro, pLenti4_Flag_HA_Puro_LSD1, pSlik-Neo, or pSlik-Neo_Flag-HA_LSD1 virus and subsequently selected in medium containing 1 µM puromycin (Sigma). Stable transfection of C3H-10T1/2 with pRTS_Puro_GW, pRTS_Puro_GW-Flag_LSD1, or pRTS_Puro_GW-Flag_LSD1-K661A-W751A-Y761S was carried out in 6-well plates. Briefly, at 50-70% confluence cell medium was changed for growth medium (DMEM, 10% FBS, non-essential amino-acids and glutamine) for 3 h. Cells were then transfected with Fugene HD (Roche) and 750 ng of DNA in growth medium without FBS for 5 h at 37° C. FBS was then adjusted at 10% and cells were selected using 0.5 µM puromycin (Sigma). 3T3-L1 cells were transfected with 1 µM siRNA against Nrf1 or unrelated control (Invitrogen) using DharmaFECT 1 (Thermo Scientific) according to the manufacturer's instructions. siRNA oligonucleotide sequences were as follows:

```
Nrf1 siRNA sense:
5'-UAUGGUAGCCAUGUGUUCAGUUUGG-3'

Control-Nrf1 siRNA sense:
5'-UAUUUGGAUGUACCUGUGGACUUGG-3'

C/ebpβ siRNA sense:
5'-CCAAGAUGCGCAACCUGGAGACGCA-3'

Control-C/ebpβ siRNA sense:
5'-CCAGUACGCCAAGUCGAGCAAGGCA-3'
```

Data Analysis

Data are represented as mean+standard error of the mean (SEM). Significance (except FIG. 6a) was calculated by a two-tailed Student's t test.

TABLE 3

Primers used for qPCR analyses

| Gene | Sense | Primer 5'-3' | Gene | Sense | Primer 5'-3' |
|---|---|---|---|---|---|
| Tbp | fw | GAAGCTGCGGTACAATTCCAG | Pdk4 | fw | CAAGGAGATCTGAATCTCTA |
| Tbp | rev | CCCCTTGTACCCTTCACCAAT | Pdk4 | rev | GATAATGTTTGAAGGCTGAC |
| 36B4 | fw | GCGTCCTGGCATTGTCTGT | Acot2 | fw | ATGGTGGCCTCGTCTTTCG |
| 36b4 | rev | GCAAATGCAGATGGATCAGCC | Acot2 | rev | GAGCGGCGGAGGTACAAAC |
| Hprt | fw | AGGGCATATCCAACAACAAACTT | Slc29a1 | fw | CACCAGCCTCAGGACAGGTAT |
| Hprt | rev | GTTAAGCAGTACAGCCCCAAA | Slc29a1 | rev | GTCCAGGCGGTTTGTGAAA |
| Prdm16 | fw | CCCCCAACGCTCTCGGATCC | Fabp4 | fw | AGGGCAATGAGGTCACATCC |
| Prdm16 | rev | CCGAAGCAGCGGTTGCACAG | Fabp4 | rev | GCATCTCGTTATCCGAGTACCAG |
| Pgc-1α | fw | AAGTGTGGAACTCTCTGGAACTG | Adipoq | fw | GCACTGGCAAGTTCTACTGCAA |
| Pgc-1α | rev | GGGTTATCTTGGTTGGCTTTATG | Adipoq | rev | GTAGGTGAAGAGAACGGCCTTGT |
| Ucp1 | fw | TGGCAAAAACAGAAGGATT | Tnfa | fw | TCGTAGCAAACCACCAAGTG |
| Ucp1 | rev | CGAGTCGCAGAAAAGAAGC | Tnfa | rev | AGATAGCAAATCGGCTGACG |
| Cidea | fw | TGCTCTTCTGTATCGCCCAGT | Agt | fw | GCACCCTGGTCTCTTTCTACC |
| Cidea | rev | GCCGTGTTAAGGAATCTGCTG | Agt | rev | TGTGTCCATCTAGTCGGGAGG |
| Acads | fw | TCGCTGGTCCCTTCGTAGAT | Lep | fw | CCTGCTCCAGCAGCTGCAAG |
| Acads | rev | TGGGATGGGCTTCAAAATAG | Lep | rev | ACCGACACAGGGGTGTCCAGC |
| Hadbb | fw | TTCCCAACTGCACTCTGCCCCA | Retn | fw | CTGTCCAGTCTATCCTTGCAC |
| Hadbb | rev | AGCAGAAATGGAATGCGGACCCC | Retn | rev | CAGAAGGCACAGCAGTCTTGA |
| Fabp3 | fw | TGACGTGGACGGAGGCAAAC | Pparγ | fw | GAAAGACAACGGACAAATCACC |
| Fabp3 | rev | GACGGAGCAGCCAGGTCACG | Pparγ | rev | GGGGGTGATATGTTTGAACTTG |
| Ucp2 | fw | ACCAAGGGCTCAGAGCATGCA | Ndufa6 | fw | GTCACAGACCCCAGAGTGGT |
| Ucp2 | rev | AGGTCACCAGCTCAGCACAGT | Ndufa6 | rev | TAACATGCACCTTCCCATCA |
| Ucp3 | fw | ACTCCAGCGTCGCCATCAGGATTCT | Sdha | fw | ACACAGACCTGGTGGAGACC |

TABLE 3-continued

Primers used for qPCR analyses

| Gene | Sense | Primer 5'-3' | Gene | Sense | Primer 5'-3' |
|---|---|---|---|---|---|
| Ucp3 | rev | TAAACAGGTGAGACTCCAGCAACTT | Sdha | rev | GGATGGGCTTGGAGTAATCA |
| Cpt1b | fw | CAGCTGGCTGGTTGTTGTCA | Uqcre1 | fw | GACAACGTGACCCTCCAAGT |
| Cpt1b | rev | TTGTCGGAAGAAGAAAATGC | Uqcre1 | rev | ACTGGTACATAGGCGCATCC |
| Acaca | fw | GGGCTGCTAAGGTGGAAGTA | Cox6a1 | fw | TGCTCAACGTGTTCCTCAAG |
| Acaca | rev | AAGTTGAGGAAGATGTGGTT | Cox6a1 | rev | TAAGGGTCCAAAACCAGTGC |
| Cox8b | fw | GAACCATGAAGCCAACGACT | Atp5b | fw | GAGGGATTACCACCCATCCT |
| Cox8b | rev | GCGAAGTTCACAGTGGTTCC | Atp5b | rev | CATGATTCTGCCCAAGGTCT |
| Ear2 | fw | CCTGTAACCCCAGAACTCCA | Nrf1 | fw | TGGAGTCCAAGATGCTAATG |
| Ear2 | rev | CAGATGAGCAAAGGTGCAAA | Nrf1 | rev | AGAGCTCCATGCTACTGTTC |
| Klhl13 | fw | AGAATTGGTTGCTGCAATACTCC | Tfam | fw | AGGCCCGGCAGAGACGGTTAA |
| Klhl13 | rev | AAGGCACAGTTTCAAGTGCTG | Tfam | rev | CCTGAGCCGAATCATCCTTTGCC |
| Tbx1 | fw | GGCAGGCAGACGAATGTTC | $C_5$ | fw | CAGCTACAGAAGGAAGTTGG |
| Tbx1 | rev | TTGTCATCTACGGGCACAAAG | $C_5$ | rev | AGGAATAGCGAGGGTCAGTC |
| Slc27a1 | fw | CTGGGACTTCCGTGGACCT | Gapdh | fw | TGCCAAGTATGATGACATCAAGAAG |
| Slc27a1 | rev | TCTTGCAGACGATACGCAGAA | Gapdh | rev | GGTCCTCAGTGTAGCCCAAGAT |
| Tmem26 | fw | ACCCTGTCATCCCACAGAG | mbLSD1 | fw | GTGTTCTGGGACCCAAGTGT |
| Tmem26 | rev | TGTTTGGTGGAGTCCTAAGGTC | mbLSD1 | rev | TAATGCCAGCAGCTTCTCCT |
| Sp100 | fw | TGATGGAGGGAACCCAAACTC | hLSD1 | fw | GCTCGGGGCTCTTATTCCTA |
| Sp100 | rev | CTTCCTTGAGAATAGCTGGCAC | hLSD1 | rev | ATGTTCTCCCGCAAAGAAGA |
| Cd137 | fw | CGTGCAGAACTCCTGTGATAAC | Cox2 | fw | CAGTCCCCTCCCTAGGACTT |
| Cd137 | rev | GTCCACCTATGCTGGAGGAAGG | Cox2 | rev | TTTCAGAGCATTGGCCATAGAA |
| Cd40 | fw | TTGTTGACAGCGGTCCATCTA | Fasn | fw | AGGATATGGAGAGGGCTGGT |
| Cd40 | rev | CCATCGTGGAGGTACTGTTTG | Fasn | rev | ACCCAAGCATCATTTTCGTC |
| Eva1 | fw | CCACTTCTCCTGAGTTTACAGC | C/ebpα | fw | TTACAACAGGCCAGGTTTCC |
| Eva1 | rev | GCATTTTAACCGAACATCTGTCC | C/ebpα | rev | CTCTGGGATGGATCGATTGT |
| Fbxo31 | fw | AAACTGCTTCACCGATACAGAC | C/ebpβ | fw | CAAGCTGAGCGACGAGTACA |
| Fbxo31 | rev | ACCACGACGTTCAGCAATCC | C/ebpβ | rev | AGCTGCTCCACCTTCTTCTG |
| Hspb7 | fw | GAGCATGTTTTCAGACGACTTTG | C/ebpδ | fw | AGAAGCTGGTGGAGTTGTCG |
| Hspb7 | rev | CCGAGGGTCTTGATGTTTCCTT | C/ebpδ | rev | CGCAGGTCCCAAAGAAACTA |
| Ebf3 | fw | CGAAAGGACCGCTTTTGTGG | Rxrα | fw | GTCGAGCCCAAGACTGAGAC |
| Ebf3 | rev | AGTGAATGCCGTTGTTGGTTT | Rxrα | rev | TCTAGGGGCAGCTCAGAAAA |
| Oplah | fw | CTTCACGCACGTCTCCTTGT | β-Actin | fw | CCCTGTATGCCTCTGGTCGT |
| Oplah | rev | GCATCTGCACAGGCCGTAT | β-Actin | rev | ATGGCGTGAGGGAGAGCAT |

REFERENCES

1. Metzger, E., et al. LSD1 demethylates repressive histone marks to promote androgen-receptor-dependent transcription. *Nature* 437, 436-439 (2005).
2. Shi, Y., et al. Histone demethylation mediated by the nuclear amine oxidase homolog LSD1. *Cell* 119, 941-953 (2004).
3. Wang, J., et al. The lysine demethylase LSD1 (KDM1) is required for maintenance of global DNA methylation. *Nat Genet* 41, 125-129 (2009).
4. Wang, J., et al. Opposing LSD1 complexes function in developmental gene activation and repression programmes. *Nature* 446, 882-887 (2007).
5. Foster, C. T., et al. Lysine-specific demethylase 1 regulates the embryonic transcriptome and CoREST stability. *Mol Cell Biol* 30, 4851-4863 (2010).
6. Macfarlan, T. S., et al. Endogenous retroviruses and neighboring genes are coordinately repressed by LSD1/KDM1A. *Genes Dev* 25, 594-607 (2011).
7. Chen, Y., Jie, W., Yan, W., Zhou, K. & Xiao, Y. Lysine-specific histone demethylase 1 (LSD1): A potential molecular target for tumor therapy. *Crit Rev Eukaryot Gene Expr* 22, 53-59 (2012).
8. Wang, Y., et al. LSD1 is a subunit of the NuRD complex and targets the metastasis programs in breast cancer. *Cell* 138, 660-672 (2009).
9. Musri, M. M., et al. Histone demethylase LSD1 regulates adipogenesis. *J Biol Chem* 285, 30034-30041 (2010).
10. Hino, S., et al. FAD-dependent lysine-specific demethylase-1 regulates cellular energy expenditure. *Nat Commun* 3, 758 (2012).
11. Langin, D. Recruitment of brown fat and conversion of white into brown adipocytes: strategies to fight the metabolic complications of obesity? *Biochim Biophys Acta* 1801, 372-376 (2010).
12. Matthias, A., Jacobsson, A., Cannon, B. & Nedergaard, J. The bioenergetics of brown fat mitochondria from UCP1-ablated mice. Ucp1 is not involved in fatty acid-induced de-energization ("uncoupling"). *J Biol Chem* 274, 28150-28160 (1999).
13. Monemdjou, S., Kozak, L. P. & Harper, M. E. Mitochondrial proton leak in brown adipose tissue mitochondria of Ucp1-deficient mice is GDP insensitive. *Am J Physiol* 276, E1073-1082 (1999).
14. Himms-Hagen, J. Brown adipose tissue thermogenesis: interdisciplinary studies. *FASEB J* 4, 2890-2898 (1990).
15. Fisher, F. M., et al. FGF21 regulates PGC-1alpha and browning of white adipose tissues in adaptive thermogenesis. *Genes Dev* 26, 271-281 (2012).
16. Kajimura, S., Seale, P. & Spiegelman, B. M. Transcriptional control of brown fat development. *Cell Metab* 11, 257-262 (2010).
17. Seale, P., et al. Prdm16 determines the thermogenic program of subcutaneous white adipose tissue in mice. *J Clin Invest* 121, 96-105 (2011).
18. Petrovic, N., et al. Chronic peroxisome proliferator-activated receptor gamma (PPARgamma) activation of epididymally derived white adipocyte cultures reveals a population of thermogenically competent, UCP1-containing adipocytes molecularly distinct from classic brown adipocytes. *J Biol Chem* 285, 7153-7164 (2010).
19. Wu, J., et al. Beige adipocytes are a distinct type of thermogenic fat cell in mouse and human. *Cell* 150, 366-376 (2012).
20. Seale, P., et al. PRDM16 controls a brown fat/skeletal muscle switch. *Nature* 454, 961-967 (2008).
21. Cristancho, A. G. & Lazar, M. A. Forming functional fat: a growing understanding of adipocyte differentiation. *Nat Rev Mol Cell Biol* 12, 722-734 (2011).
22. Stephens, J. M. The fat controller: adipocyte development. *PLoS Biol* 10, e1001436 (2012).
23. Wu, J., Cohen, P. & Spiegelman, B. M. Adaptive thermogenesis in adipocytes: is beige the new brown? *Genes Dev* 27, 234-250 (2013).
24. Mazzucotelli, A., et al. The transcriptional coactivator peroxisome proliferator activated receptor (PPAR)gamma coactivator-1 alpha and the nuclear receptor PPAR alpha control the expression of glycerol kinase and metabolism genes independently of PPAR gamma activation in human white adipocytes. *Diabetes* 56, 2467-2475 (2007).
25. Tiraby, C., et al. Acquirement of brown fat cell features by human white adipocytes. *J Biol Chem* 278, 33370-33376 (2003).
26. Puigserver, P., et al. A cold-inducible coactivator of nuclear receptors linked to adaptive thermogenesis. *Cell* 92, 829-839 (1998).
27. Scarpulla, R. C. Transcriptional paradigms in mammalian mitochondrial biogenesis and function. *Physiol Rev* 88, 611-638 (2008).
28. Puigserver, P. & Spiegelman, B. M. Peroxisome proliferator-activated receptor-gamma coactivator 1 alpha (PGC-1 alpha): transcriptional coactivator and metabolic regulator. *Endocr Rev* 24, 78-90 (2003).
29. Wu, Z., et al. Mechanisms controlling mitochondrial biogenesis and respiration through the thermogenic coactivator PGC-1. *Cell* 98, 115-124 (1999).
30. Koh, E. H., et al. Essential role of mitochondrial function in adiponectin synthesis in adipocytes. *Diabetes* 56, 2973-2981 (2007).
31. Auffret, J., et al. Beige differentiation of adipose depots in mice lacking prolactin receptor protects against high-fat-diet-induced obesity. *FASEB J* 26, 3728-3737 (2012).
32. Vegiopoulos, A., et al. Cyclooxygenase-2 controls energy homeostasis in mice by de novo recruitment of brown adipocytes. *Science* 328, 1158-1161 (2010).
33. Yadav, H., et al. Protection from obesity and diabetes by blockade of TGF-beta/Smad3 signaling. *Cell Metab* 14, 67-79 (2011).
34. Beranger, G. E., et al. In vitro brown and "brite"/"beige" adipogenesis: Human cellular models and molecular aspects. *Biochim Biophys Acta* (2012).
35. Gesta, S., Tseng, Y. H. & Kahn, C. R. Developmental origin of fat: tracking obesity to its source. *Cell* 131, 242-256 (2007).
36. Metzger, E., et al. Phosphorylation of histone H3T6 by PKCbeta(I) controls demethylation at histone H3K4. *Nature* 464, 792-796 (2010).
37. Rosen, E. D. & Spiegelman, B. M. Adipocytes as regulators of energy balance and glucose homeostasis. *Nature* 444, 847-853 (2006).
38. He, W., et al. Adipose-specific peroxisome proliferator-activated receptor gamma knockout causes insulin resistance in fat and liver but not in muscle. *Proc Natl Acad Sci USA* 100, 15712-15717 (2003).
39. Shan, T., Liu, W. & Kuang, S. Fatty acid binding protein 4 expression marks a population of adipocyte progenitors in white and brown adipose tissues. *FASEB J* 27, 277-287 (2013).
40. Vooijs, M., Jonkers, J. & Berns, A. A highly efficient ligand-regulated Cre recombinase mouse line shows that LoxP recombination is position dependent. *EMBO Rep* 2, 292-297 (2001).

41. Kanehisa, M., Goto, S., Sato, Y., Furumichi, M. & Tanabe, M. KEGG for integration and interpretation of large-scale molecular data sets. *Nucleic Acids Res* 40, D109-114 (2012).
42. Heinz, S., et al. Simple combinations of lineage-determining transcription factors prime cis-regulatory elements required for macrophage and B cell identities. *Mol Cell* 38, 576-589 (2010).
43. Siersbaek, R., et al. Extensive chromatin remodelling and establishment of transcription factor 'hotspots' during early adipogenesis. *EMBO J* 30, 1459-1472 (2011).
44. Farmer, S. R. Regulation of PPARgamma activity during adipogenesis. *Int J Obes (Lond)* 29 Suppl 1, S13-16 (2005).
45. Koppen, A. & Kalkhoven, E. Brown vs white adipocytes: the PPARgamma coregulator story. *FEBS Lett* 584, 3250-3259 (2010).
46. Nielsen, R., et al. Genome-wide profiling of PPARgamma:RXR and RNA polymerase II occupancy reveals temporal activation of distinct metabolic pathways and changes in RXR dimer composition during adipogenesis. *Genes Dev* 22, 2953-2967 (2008).
47. Kajimura, S., et al. Initiation of myoblast to brown fat switch by a PRDM16-C/EBP-beta transcriptional complex. *Nature* 460, 1154-1158 (2009).
48. Duteil, D., et al. The transcriptional coregulators TIF2 and SRC-1 regulate energy homeostasis by modulating mitochondrial respiration in skeletal muscles. *Cell Metab* 12, 496-508 (2010).
49. Schwenk, F., Baron, U. & Rajewsky, K. A cre-transgenic mouse strain for the ubiquitous deletion of loxP-flanked gene segments including deletion in germ cells. *Nucleic Acids Res* 23, 5080-5081 (1995).
50. Puccio, H., et al. Mouse models for Friedreich ataxia exhibit cardiomyopathy, sensory nerve defect and Fe—S enzyme deficiency followed by intramitochondrial iron deposits. *Nat Genet* 27, 181-186 (2001).
51. Picard, F., et al. SRC-1 and TIF2 control energy balance between white and brown adipose tissues. *Cell* 111, 931-941 (2002).
52. Hamalainen, N. & Pette, D. The histochemical profiles of fast fiber types IIB, IID, and IIA in skeletal muscles of mouse, rat, and rabbit. *J Histochem Cytochem* 41, 733-743 (1993).
53. Bookout, A. L., Cummins, C. L., Mangelsdorf, D. J., Pesola, J. M. & Kramer, M. F. High-throughput real-time quantitative reverse transcription PCR. *Curr Protoc Mol Biol* Chapter 15, Unit 15 18 (2006).
54. Trapnell, C., et al. Differential gene and transcript expression analysis of RNA-seq experiments with TopHat and Cufflinks. *Nat Protoc* 7, 562-578 (2012).
55. Robinson, M. D. & Smyth, G. K. Small-sample estimation of negative binomial dispersion, with applications to SAGE data. *Biostatistics* 9, 321-332 (2008).
56. Anders, S. & Huber, W. Differential expression analysis for sequence count data. *Genome Biol* 11, R106 (2010).
57. Metzger, E., et al. Phosphorylation of histone H3 at threonine 11 establishes a novel chromatin mark for transcriptional regulation. *Nat Cell Biol* 10, 53-60 (2008).
58. Langmead, B., Trapnell, C., Pop, M. & Salzberg, S. L. Ultrafast and memory-efficient alignment of short DNA sequences to the human genome. *Genome Biol* 10, R25 (2009).
59. Zhang, Y., et al. Model-based analysis of ChIP-Seq (MACS). *Genome Biol* 9, R137 (2008).
60. Thorvaldsdottir, H., Robinson, J. T. & Mesirov, J. P. Integrative Genomics Viewer (IGV): high-performance genomics data visualization and exploration. *Brief Bioinform* (2012).
61. Hölzel, M., et al. Rapid conditional knock-down-knock-in system for mammalian cells. *Nucleic Acids Res* 35, e17 (2007).
62. Rodbell, M. Metabolism of Isolated Fat Cells. I. Effects of Hormones on Glucose Metabolism and Lipolysis. *J Biol Chem* 239, 375-380 (1964).
63. Soukas, A., Socci, N. D., Saatkamp, B. D., Novelli, S. & Friedman, J. M. Distinct transcriptional profiles of adipogenesis in vivo and in vitro. *J Biol Chem* 276, 34167-34174 (2001).
64. Hood, D. A., Irrcher, I., Ljubicic, V. & Joseph, A. M. Coordination of metabolic plasticity in skeletal muscle. *J Exp Biol* 209, 2265-2275 (2006).

The invention claimed is:

1. A method of modelling obesity or an obesity-related disorder selected from among insulin resistance and type 2 diabetes, wherein said method comprises the steps of:
   (a) providing a genetically modified mouse whose genome comprises a disruption in the endogenous gene encoding Lysine-specific Demethylase 1 (LSD1), wherein said disruption is a heterozygous deletion of said endogenous LSD1 gene, further wherein the presence of said disruption results in reduced expression of endogenous LSD1 and a corresponding reduced amount of the LSD1 gene-product in at least one tissue or at least one cell type of said mouse; and
   (b) feeding said genetically modified mouse a high fat diet until it develops one or more symptoms of obesity selected from the group consisting of increased weight, increased body fat content, reduced insulin sensitivity, and glucose intolerance.

2. The method of claim 1, wherein said genetically modified mouse develops obesity after said high fat diet.

3. The method of claim 1, wherein said genetically modified mouse has at least one symptom of type 2 diabetes.

4. A method for identifying a compound useful in the treatment and/or prevention of obesity or an obesity-related disorder selected from among insulin resistance and type 2 diabetes, said method comprising the steps of: (a) administering a test compound to a genetically modified mouse model generated by the method set forth in claim 1, and (b) determining the effect of the test compound on the initiation, maintenance, or progression of at least one obesity-related parameter in said genetically modified mouse, wherein said at least one obesity-related parameter is selected from the group consisting of the mass of white adipose tissue, the total mass of adipose tissue, and glucose intolerance, and thereby identifying a compound that inhibits obesity or said obesity-related disorder.

* * * * *

SEQUENCE LISTING

<160> NUMBER OF SEQ ID NOS: 133

<210> SEQ ID NO 1
<211> LENGTH: 2559
<212> TYPE: DNA
<213> ORGANISM: homo sapiens

<400> SEQUENCE: 1

```
atgttatctg ggaagaaggc ggcagccgcg gcggcggcgg ctgcagcggc agcaaccggg      60
acggaggctg gccctgggac agcaggcggc tccgagaacg ggtctgaggt ggccgcgcag     120
cccgcgggcc tgtcgggccc agccgaggtc gggccggggg cggtggggga gcgcacaccc     180
cgcaagaaag agcctccgcg ggcctcgccc cccgggggcc tggcggaacc gccggggtcc     240
gcagggcctc aggccggccc tactgtcgtg cctgggtctg cgaccccat  ggaaactgga     300 atagcagaga ctccggaggg gcgtcggacc agccggcgca agcgggcgaa ggtagagtac     360
agagagatgg atgaaagctt ggccaacctc tcagaagatg agtattattc agaagaagag     420
agaaatgcca aagcagagaa ggaaaagaag cttccccac  caccccctca agccccacct     480
gaggaagaaa atgaaagtga gcctgaagaa ccatcgggtg tggagggcgc agctttccag     540
```

```
agccgacttc ctcatgaccg gatgacttct caagaagcag cctgttttcc agatattatc      600
agtggaccac aacagaccca gaaggttttt cttttcatta gaaaccgcac actgcagttg      660
tggttggata tccaaagat tcagctgaca tttgaggcta ctctccaaca attagaagca       720
ccttataaca gtgatactgt gcttgtccac cgagttcaca gttatttaga gcgtcatggt      780
cttatcaact tcggcatcta aagaggata aaacccctac caactaaaaa gacaggaaag       840
gtaattatta taggctctgg ggtctcaggc ttggcagcag ctcgacagtt acaaagtttt      900
ggaatggatg tcacactttt ggaagccagg gatcgtgtgg gtggacgagt tgccacattt      960
cgcaaaggaa actatgtagc tgatcttgga gccatggtgg taacaggtct ggagggaat      1020 cctatggctg tggtcagcaa acaagtaaat atggaactgg ccaagatcaa gcaaaaatgc     1080
ccactttatg aagccaacgg acaagctgtt cctaaagaga aagatgaaat ggtagagcaa     1140
gagtttaacc ggttgctaga agctacatct taccttagtc atcaactaga cttcaatgtc     1200
ctcaataata agcctgtgtc ccttggccag gcattggaag ttgtcattca gttacaagag     1260
aagcatgtca aagatgagca gattgaacat tggaagaaga tagtgaaaac tcaggaagaa     1320
ttgaaagaac ttcttaataa gatggtaaat ttgaaagaga aaattaaaga actccatcag     1380
caatacaaag aagcatctga agtaaagcca cccagagata ttactgccga gttcttagtg     1440
aaaagcaaac acagggatct gaccgcccta tgcaaggaat atgatgaatt agctgaaaca     1500
caaggaaagc tagaagaaaa acttcaggag ttggaagcga atcccccaag tgatgtatat     1560
ctctcatcaa gagacagaca aatacttgat tggcattttg caaatcttga atttgctaat     1620
gccacacctc tctcaactct ctcccttaag cactgggatc aggatgatga ctttgagttc     1680
actggcagcc acctgacagt aaggaatggc tactcgtgtg tgcctgtggc tttagcagaa     1740
ggcctagaca ttaaactgaa tacagcagtg cgacaggttc gctacacggc ttcaggatgt     1800
gaagtgatag ctgtgaatac ccgctccacg agtcaaacct ttatttataa atgcgacgca     1860
gttctctgta cccttcccct gggtgtgctg aagcagcagc caccagccgt tcagtttgtg     1920
ccacctctcc ctgagtggaa aacatctgca gtccaaagga tgggatttgg caaccttaac     1980
aaggtggtgt tgtgttttga tcgggtgttc tgggatccaa gtgtcaattt gttcgggcat     2040
gttggcagta cgactgccag cagggggtgag ctcttcctct tctggaacct ctataaagct     2100
ccaatactgt tggcactagt ggcaggagaa gctgctggta tcatgaaaaa cataagtgac     2160
gatgtgattg ttggccgatg cctggccatt ctcaaaggga ttttttggtag cagtgcagta     2220 cctcagccca aagaaactgt ggtgtctcgt tggcgtgctg atccctgggc tcggggctct     2280
tattcctatg ttgctgcagg atcatctgga aatgactatg atttaatggc tcagccaatc     2340
actcctggcc cctcgattcc aggtgcccca cagccgattc cacgactctt ctttgcggga     2400
gaacatacga tccgtaacta cccagccaca gtgcatggtg ctctgctgag tgggctgcga     2460
gaagcgggaa gaattgcaga ccagtttttg ggggccatgt atacgctgcc tcgccaggcc     2520
acaccaggtg ttcctgcaca gcagtcccca agcatgtga                            2559
```

<210> SEQ ID NO 2
<211> LENGTH: 3053
<212> TYPE: DNA
<213> ORGANISM: homo sapiens
<220> FEATURE:
<221> NAME/KEY: CDS
<222> LOCATION: (150)..(2708)

<400> SEQUENCE: 2

-continued

```
ggcgcggcgg gagcgcgctt ggcgcgtgcg tacgcgacgg cggttggcgg cgcgcgggca      60
gcgtgaagcg aggcgaggca aggcttttcg gacccacgga gcgacagagc gagcggcccc     120
tacggccgtc ggcggcccgg cggcccgag atg tta tct ggg aag aag gcg gca      173
                                Met Leu Ser Gly Lys Lys Ala Ala
                                 1               5 gcc gcg gcg gcg gcg gct gca gcg gca gca acc ggg acg gag gct ggc      221
Ala Ala Ala Ala Ala Ala Ala Ala Ala Ala Thr Gly Thr Glu Ala Gly
     10                  15                  20 cct ggg aca gca ggc ggc tcc gag aac ggg tct gag gtg gcc gcg cag      269
Pro Gly Thr Ala Gly Gly Ser Glu Asn Gly Ser Glu Val Ala Ala Gln
 25                  30                  35                  40 ccc gcg ggc ctg tcg ggc cca gcc gag gtc ggg ccg ggg gcg gtg ggg      317
Pro Ala Gly Leu Ser Gly Pro Ala Glu Val Gly Pro Gly Ala Val Gly
                 45                  50                  55 gag cgc aca ccc cgc aag aaa gag cct ccg cgg gcc tcg ccc ccc ggg      365
Glu Arg Thr Pro Arg Lys Lys Glu Pro Pro Arg Ala Ser Pro Pro Gly
         60                  65                  70 ggc ctg gcg gaa ccg ccg ggg tcc gca ggg cct cag gcc ggc cct act      413
Gly Leu Ala Glu Pro Pro Gly Ser Ala Gly Pro Gln Ala Gly Pro Thr
     75                  80                  85 gtc gtg cct ggg tct gcg acc ccc atg gaa act gga ata gca gag act      461
Val Val Pro Gly Ser Ala Thr Pro Met Glu Thr Gly Ile Ala Glu Thr
 90                  95                 100 ccg gag ggg cgt cgg acc agc cgg cgc aag cgg gcg aag gta gag tac      509
Pro Glu Gly Arg Arg Thr Ser Arg Arg Lys Arg Ala Lys Val Glu Tyr
105                 110                 115                 120 aga gag atg gat gaa agc ttg gcc aac ctc tca gaa gat gag tat tat      557
Arg Glu Met Asp Glu Ser Leu Ala Asn Leu Ser Glu Asp Glu Tyr Tyr
                125                 130                 135 tca gaa gaa gag aga aat gcc aaa gca gag aag gaa aag aag ctt ccc      605
Ser Glu Glu Glu Arg Asn Ala Lys Ala Glu Lys Glu Lys Lys Leu Pro
        140                 145                 150 cca cca ccc cct caa gcc cca cct gag gaa gaa aat gaa agt gag cct      653
Pro Pro Pro Pro Gln Ala Pro Pro Glu Glu Glu Asn Glu Ser Glu Pro
    155                 160                 165 gaa gaa cca tcg ggt gtg gag ggc gca gct ttc cag agc cga ctt cct      701
Glu Glu Pro Ser Gly Val Glu Gly Ala Ala Phe Gln Ser Arg Leu Pro
170                 175                 180 cat gac cgg atg act tct caa gaa gca gcc tgt ttt cca gat att atc      749
His Asp Arg Met Thr Ser Gln Glu Ala Ala Cys Phe Pro Asp Ile Ile
185                 190                 195                 200 agt gga cca caa cag acc cag aag gtt ttt ctt ttc att aga aac cgc      797
Ser Gly Pro Gln Gln Thr Gln Lys Val Phe Leu Phe Ile Arg Asn Arg
                205                 210                 215 aca ctg cag ttg tgg ttg gat aat cca aag att cag ctg aca ttt gag      845
Thr Leu Gln Leu Trp Leu Asp Asn Pro Lys Ile Gln Leu Thr Phe Glu
        220                 225                 230 gct act ctc caa caa tta gaa gca cct tat aac agt gat act gtg ctt      893
Ala Thr Leu Gln Gln Leu Glu Ala Pro Tyr Asn Ser Asp Thr Val Leu
    235                 240                 245 gtc cac cga gtt cac agt tat tta gag cgt cat ggt ctt atc aac ttc      941
Val His Arg Val His Ser Tyr Leu Glu Arg His Gly Leu Ile Asn Phe
250                 255                 260 ggc atc tat aag agg ata aaa ccc cta cca act aaa aag aca gga aag      989
Gly Ile Tyr Lys Arg Ile Lys Pro Leu Pro Thr Lys Lys Thr Gly Lys
265                 270                 275                 280 gta att att ata ggc tct ggg gtc tca ggc ttg gca gca gct cga cag     1037
Val Ile Ile Ile Gly Ser Gly Val Ser Gly Leu Ala Ala Ala Arg Gln
```

```
                    285                 290                 295
tta caa agt ttt gga atg gat gtc aca ctt ttg gaa gcc agg gat cgt    1085
Leu Gln Ser Phe Gly Met Asp Val Thr Leu Leu Glu Ala Arg Asp Arg
            300                 305                 310 gtg ggt gga cga gtt gcc aca ttt cgc aaa gga aac tat gta gct gat    1133
Val Gly Gly Arg Val Ala Thr Phe Arg Lys Gly Asn Tyr Val Ala Asp
        315                 320                 325 ctt gga gcc atg gtg gta aca ggt ctt gga ggg aat cct atg gct gtg    1181
Leu Gly Ala Met Val Val Thr Gly Leu Gly Gly Asn Pro Met Ala Val
    330                 335                 340 gtc agc aaa caa gta aat atg gaa ctg gcc aag atc aag caa aaa tgc    1229
Val Ser Lys Gln Val Asn Met Glu Leu Ala Lys Ile Lys Gln Lys Cys
345                 350                 355                 360 cca ctt tat gaa gcc aac gga caa gct gtt cct aaa gag aaa gat gaa    1277
Pro Leu Tyr Glu Ala Asn Gly Gln Ala Val Pro Lys Glu Lys Asp Glu
                365                 370                 375 atg gta gag caa gag ttt aac cgg ttg cta gaa gct aca tct tac ctt    1325
Met Val Glu Gln Glu Phe Asn Arg Leu Leu Glu Ala Thr Ser Tyr Leu
            380                 385                 390 agt cat caa cta gac ttc aat gtc ctc aat aat aag cct gtg tcc ctt    1373
Ser His Gln Leu Asp Phe Asn Val Leu Asn Asn Lys Pro Val Ser Leu
        395                 400                 405 ggc cag gca ttg gaa gtt gtc att cag tta caa gag aag cat gtc aaa    1421
Gly Gln Ala Leu Glu Val Val Ile Gln Leu Gln Glu Lys His Val Lys
    410                 415                 420 gat gag cag att gaa cat tgg aag aag ata gtg aaa act cag gaa gaa    1469
Asp Glu Gln Ile Glu His Trp Lys Lys Ile Val Lys Thr Gln Glu Glu
425                 430                 435                 440 ttg aaa gaa ctt ctt aat aag atg gta aat ttg aaa gag aaa att aaa    1517
Leu Lys Glu Leu Leu Asn Lys Met Val Asn Leu Lys Glu Lys Ile Lys
                445                 450                 455 gaa ctc cat cag caa tac aaa gaa gca tct gaa gta aag cca ccc aga    1565
Glu Leu His Gln Gln Tyr Lys Glu Ala Ser Glu Val Lys Pro Pro Arg
            460                 465                 470 gat att act gcc gag ttc tta gtg aaa agc aaa cac agg gat ctg acc    1613
Asp Ile Thr Ala Glu Phe Leu Val Lys Ser Lys His Arg Asp Leu Thr
        475                 480                 485 gcc cta tgc aag gaa tat gat gaa tta gct gaa aca caa gga aag cta    1661
Ala Leu Cys Lys Glu Tyr Asp Glu Leu Ala Glu Thr Gln Gly Lys Leu
    490                 495                 500 gaa gaa aaa ctt cag gag ttg gaa gcg aat ccc cca agt gat gta tat    1709
Glu Glu Lys Leu Gln Glu Leu Glu Ala Asn Pro Pro Ser Asp Val Tyr
505                 510                 515                 520 ctc tca tca aga gac aga caa ata ctt gat tgg cat ttt gca aat ctt    1757
Leu Ser Ser Arg Asp Arg Gln Ile Leu Asp Trp His Phe Ala Asn Leu
                525                 530                 535 gaa ttt gct aat gcc aca cct ctc tca act ctc tcc ctt aag cac tgg    1805
Glu Phe Ala Asn Ala Thr Pro Leu Ser Thr Leu Ser Leu Lys His Trp
            540                 545                 550 gat cag gat gat gac ttt gag ttc act ggc agc cac ctg aca gta agg    1853
Asp Gln Asp Asp Asp Phe Glu Phe Thr Gly Ser His Leu Thr Val Arg
        555                 560                 565 aat ggc tac tcg tgt gtg cct gtg gct tta gca gaa ggc cta gac att    1901
Asn Gly Tyr Ser Cys Val Pro Val Ala Leu Ala Glu Gly Leu Asp Ile
    570                 575                 580 aaa ctg aat aca gca gtg cga cag gtt cgc tac acg gct tca gga tgt    1949
Lys Leu Asn Thr Ala Val Arg Gln Val Arg Tyr Thr Ala Ser Gly Cys
585                 590                 595                 600 gaa gtg ata gct gtg aat acc cgc tcc acg agt caa acc ttt att tat    1997
```

```
                Glu Val Ile Ala Val Asn Thr Arg Ser Thr Ser Gln Thr Phe Ile Tyr
                                605                 610                 615 aaa tgc gac gca gtt ctc tgt acc ctt ccc ctg ggt gtg ctg aag cag        2045
Lys Cys Asp Ala Val Leu Cys Thr Leu Pro Leu Gly Val Leu Lys Gln
                620                 625                 630 cag cca cca gcc gtt cag ttt gtg cca cct ctc cct gag tgg aaa aca        2093
Gln Pro Pro Ala Val Gln Phe Val Pro Pro Leu Pro Glu Trp Lys Thr
                635                 640                 645 tct gca gtc caa agg atg gga ttt ggc aac ctt aac aag gtg gtg ttg        2141
Ser Ala Val Gln Arg Met Gly Phe Gly Asn Leu Asn Lys Val Val Leu
    650                 655                 660 tgt ttt gat cgg gtg ttc tgg gat cca agt gtc aat ttg ttc ggg cat        2189
Cys Phe Asp Arg Val Phe Trp Asp Pro Ser Val Asn Leu Phe Gly His
665                 670                 675                 680 gtt ggc agt acg act gcc agc agg ggt gag ctc ttc ctc ttc tgg aac        2237
Val Gly Ser Thr Thr Ala Ser Arg Gly Glu Leu Phe Leu Phe Trp Asn
                685                 690                 695 ctc tat aaa gct cca ata ctg ttg gca cta gtg gca gga gaa gct gct        2285
Leu Tyr Lys Ala Pro Ile Leu Leu Ala Leu Val Ala Gly Glu Ala Ala
                700                 705                 710 ggt atc atg gaa aac ata agt gac gat gtg att gtt ggc cga tgc ctg        2333
Gly Ile Met Glu Asn Ile Ser Asp Asp Val Ile Val Gly Arg Cys Leu
                715                 720                 725 gcc att ctc aaa ggg att ttt ggt agc agt gca gta cct cag ccc aaa        2381
Ala Ile Leu Lys Gly Ile Phe Gly Ser Ser Ala Val Pro Gln Pro Lys
730                 735                 740 gaa act gtg gtg tct cgt tgg cgt gct gat ccc tgg gct cgg ggc tct        2429
Glu Thr Val Val Ser Arg Trp Arg Ala Asp Pro Trp Ala Arg Gly Ser
745                 750                 755                 760 tat tcc tat gtt gct gca gga tca tct gga aat gac tat gat tta atg        2477
Tyr Ser Tyr Val Ala Ala Gly Ser Ser Gly Asn Asp Tyr Asp Leu Met
                765                 770                 775 gct cag cca atc act cct ggc ccc tcg att cca ggt gcc cca cag ccg        2525
Ala Gln Pro Ile Thr Pro Gly Pro Ser Ile Pro Gly Ala Pro Gln Pro
                780                 785                 790 att cca cga ctc ttc ttt gcg gga gaa cat acg atc cgt aac tac cca        2573
Ile Pro Arg Leu Phe Phe Ala Gly Glu His Thr Ile Arg Asn Tyr Pro
                795                 800                 805 gcc aca gtg cat ggt gct ctg ctg agt ggg ctg cga gaa gcg gga aga        2621
Ala Thr Val His Gly Ala Leu Leu Ser Gly Leu Arg Glu Ala Gly Arg
    810                 815                 820 att gca gac cag ttt ttg ggg gcc atg tat acg ctg cct cgc cag gcc        2669
Ile Ala Asp Gln Phe Leu Gly Ala Met Tyr Thr Leu Pro Arg Gln Ala
825                 830                 835                 840 aca cca ggt gtt cct gca cag cag tcc cca agc atg tga gacagatgca         2718
Thr Pro Gly Val Pro Ala Gln Gln Ser Pro Ser Met
                845                 850 ttctaaggga agaggcccat gtgcctgttt ctgccatgta aggaaggctc ttctagcaat     2778
actagatccc actgagaaaa tccaccctgg catctgggct cctgatcagc tgatggagct     2838
cctgatttga caaaggagct tgcctccttt gaatgaccta gagcacaggg aggaacttgt     2898
ccattagttt ggaattgtgt tcttcgtaaa gactgaggca agcaagtgct gtgaaataac     2958
atcatcttag tcccttggtg tgtggggttt ttgttttttt tttatatttt gagaataaaa     3018
cttcatataa aattggcaaa aaaaaaaaaa aaaaa                                3053

<210> SEQ ID NO 3
<211> LENGTH: 852
<212> TYPE: PRT
```

-continued

<213> ORGANISM: homo sapiens

<400> SEQUENCE: 3

```
Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
            85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Glu Arg Asn Ala Lys
    130                 135                 140

Ala Glu Lys Glu Lys Lys Leu Pro Pro Pro Pro Gln Ala Pro Pro
145                 150                 155                 160

Glu Glu Glu Asn Glu Ser Glu Pro Glu Glu Pro Ser Gly Val Glu Gly
            165                 170                 175

Ala Ala Phe Gln Ser Arg Leu Pro His Asp Arg Met Thr Ser Gln Glu
            180                 185                 190

Ala Ala Cys Phe Pro Asp Ile Ile Ser Gly Pro Gln Gln Thr Gln Lys
        195                 200                 205

Val Phe Leu Phe Ile Arg Asn Arg Thr Leu Gln Leu Trp Leu Asp Asn
    210                 215                 220

Pro Lys Ile Gln Leu Thr Phe Glu Ala Thr Leu Gln Gln Leu Glu Ala
225                 230                 235                 240

Pro Tyr Asn Ser Asp Thr Val Leu Val His Arg Val His Ser Tyr Leu
            245                 250                 255

Glu Arg His Gly Leu Ile Asn Phe Gly Ile Tyr Lys Arg Ile Lys Pro
            260                 265                 270

Leu Pro Thr Lys Lys Thr Gly Lys Val Ile Ile Gly Ser Gly Val
        275                 280                 285

Ser Gly Leu Ala Ala Ala Arg Gln Leu Gln Ser Phe Gly Met Asp Val
    290                 295                 300

Thr Leu Leu Glu Ala Arg Asp Arg Val Gly Gly Arg Val Ala Thr Phe
305                 310                 315                 320

Arg Lys Gly Asn Tyr Val Ala Asp Leu Gly Ala Met Val Val Thr Gly
            325                 330                 335

Leu Gly Gly Asn Pro Met Ala Val Val Ser Lys Gln Val Asn Met Glu
            340                 345                 350

Leu Ala Lys Ile Lys Gln Lys Cys Pro Leu Tyr Glu Ala Asn Gly Gln
        355                 360                 365

Ala Val Pro Lys Glu Lys Asp Glu Met Val Glu Gln Glu Phe Asn Arg
    370                 375                 380

Leu Leu Glu Ala Thr Ser Tyr Leu Ser His Gln Leu Asp Phe Asn Val
385                 390                 395                 400
```

```
Leu Asn Asn Lys Pro Val Ser Leu Gly Gln Ala Leu Glu Val Val Ile
                405                 410                 415
Gln Leu Gln Glu Lys His Val Lys Asp Glu Gln Ile Glu His Trp Lys
            420                 425                 430
Lys Ile Val Lys Thr Gln Glu Glu Leu Lys Glu Leu Leu Asn Lys Met
        435                 440                 445
Val Asn Leu Lys Glu Lys Ile Lys Glu Leu His Gln Gln Tyr Lys Glu
450                 455                 460
Ala Ser Glu Val Lys Pro Pro Arg Asp Ile Thr Ala Glu Phe Leu Val
465                 470                 475                 480
Lys Ser Lys His Arg Asp Leu Thr Ala Leu Cys Lys Glu Tyr Asp Glu
                485                 490                 495
Leu Ala Glu Thr Gln Gly Lys Leu Glu Glu Lys Leu Gln Glu Leu Glu
            500                 505                 510
Ala Asn Pro Pro Ser Asp Val Tyr Leu Ser Ser Arg Asp Arg Gln Ile
        515                 520                 525
Leu Asp Trp His Phe Ala Asn Leu Glu Phe Ala Asn Ala Thr Pro Leu
530                 535                 540
Ser Thr Leu Ser Leu Lys His Trp Asp Gln Asp Asp Phe Glu Phe
545                 550                 555                 560
Thr Gly Ser His Leu Thr Val Arg Asn Gly Tyr Ser Cys Val Pro Val
                565                 570                 575
Ala Leu Ala Glu Gly Leu Asp Ile Lys Leu Asn Thr Ala Val Arg Gln
            580                 585                 590
Val Arg Tyr Thr Ala Ser Gly Cys Glu Val Ile Ala Val Asn Thr Arg
        595                 600                 605
Ser Thr Ser Gln Thr Phe Ile Tyr Lys Cys Asp Ala Val Leu Cys Thr
610                 615                 620
Leu Pro Leu Gly Val Leu Lys Gln Gln Pro Pro Ala Val Gln Phe Val
625                 630                 635                 640
Pro Pro Leu Pro Glu Trp Lys Thr Ser Ala Val Gln Arg Met Gly Phe
                645                 650                 655
Gly Asn Leu Asn Lys Val Val Leu Cys Phe Asp Arg Val Phe Trp Asp
            660                 665                 670
Pro Ser Val Asn Leu Phe Gly His Val Gly Ser Thr Thr Ala Ser Arg
        675                 680                 685
Gly Glu Leu Phe Leu Phe Trp Asn Leu Tyr Lys Ala Pro Ile Leu Leu
690                 695                 700
Ala Leu Val Ala Gly Glu Ala Ala Gly Ile Met Glu Asn Ile Ser Asp
705                 710                 715                 720
Asp Val Ile Val Gly Arg Cys Leu Ala Ile Leu Lys Gly Ile Phe Gly
                725                 730                 735
Ser Ser Ala Val Pro Gln Pro Lys Glu Thr Val Val Ser Arg Trp Arg
            740                 745                 750
Ala Asp Pro Trp Ala Arg Gly Ser Tyr Ser Tyr Val Ala Ala Gly Ser
        755                 760                 765
Ser Gly Asn Asp Tyr Asp Leu Met Ala Gln Pro Ile Thr Pro Gly Pro
770                 775                 780
Ser Ile Pro Gly Ala Pro Gln Pro Ile Pro Arg Leu Phe Phe Ala Gly
785                 790                 795                 800
Glu His Thr Ile Arg Asn Tyr Pro Ala Thr Val His Gly Ala Leu Leu
                805                 810                 815
Ser Gly Leu Arg Glu Ala Gly Arg Ile Ala Asp Gln Phe Leu Gly Ala
```

```
                820                 825                 830
Met Tyr Thr Leu Pro Arg Gln Ala Thr Pro Gly Val Pro Ala Gln Gln
            835                 840                 845

Ser Pro Ser Met
        850

<210> SEQ ID NO 4
<211> LENGTH: 3030
<212> TYPE: DNA
<213> ORGANISM: mus musculus
<220> FEATURE:
<221> NAME/KEY: CDS
<222> LOCATION: (139)..(2700)

<400> SEQUENCE: 4
gggcgcgtgc gcacgcgggg gtgtttggct tcgcacggag cgtgagaggt gcggggcgga      60
gaggcgcgag gcggctgcgg acccacggag cggcagaccg atcggcccct gcggcccgcg     120
gcggccaggc ggcccgag atg ttg tct ggg aag aag gcg gcg gcg gcg gca       171
                    Met Leu Ser Gly Lys Lys Ala Ala Ala Ala Ala
                     1                5                  10 gcg gca gcg gcg gcg gcg gcg gct gct ggg acc gag gcc ggg tcc ggg       219
Ala Ala Ala Ala Ala Ala Ala Ala Ala Gly Thr Glu Ala Gly Ser Gly
             15                  20                  25 gcg gcg ggc ggt gcc gag aac ggc tct gag gtg gcc gcg ccg ccc gcg       267
Ala Ala Gly Gly Ala Glu Asn Gly Ser Glu Val Ala Ala Pro Pro Ala
         30                  35                  40 ggc ctg acg ggc ccc acc gac atg gct acg ggg gcg gcg ggc gag cgc       315
Gly Leu Thr Gly Pro Thr Asp Met Ala Thr Gly Ala Ala Gly Glu Arg
     45                  50                  55 act ccc cga aag aag gag cct ccg cgg gcc tcg ccg ccc ggg ggc cta       363
Thr Pro Arg Lys Lys Glu Pro Pro Arg Ala Ser Pro Pro Gly Gly Leu
 60                  65                  70                  75 gcc gag ccg ccg ggg tct gct ggg ccc cag gcg ggg ccc aca gcc ggg       411
Ala Glu Pro Pro Gly Ser Ala Gly Pro Gln Ala Gly Pro Thr Ala Gly
                 80                  85                  90 ccc ggc tcc gcg acg ccc atg gag acc gga ata gcc gag acc ccg gag       459
Pro Gly Ser Ala Thr Pro Met Glu Thr Gly Ile Ala Glu Thr Pro Glu
             95                 100                 105 ggc cga cgg acc agc cgg cgc aag cgg gcc aag gta gaa tac aga gaa       507
Gly Arg Arg Thr Ser Arg Arg Lys Arg Ala Lys Val Glu Tyr Arg Glu
         110                 115                 120 atg gat gaa agc ttg gcc aac ctc tca gaa gat gaa tat tat tcg gaa       555
Met Asp Glu Ser Leu Ala Asn Leu Ser Glu Asp Glu Tyr Tyr Ser Glu
     125                 130                 135 gaa gaa aga aat gct aaa gca gag aag gaa aag aag ctt ccc cca cca       603
Glu Glu Arg Asn Ala Lys Ala Glu Lys Glu Lys Lys Leu Pro Pro Pro
140                 145                 150                 155 cct cct caa gcc cca cct gag gaa gaa aat gaa agt gag ccg gaa gag       651
Pro Pro Gln Ala Pro Pro Glu Glu Glu Asn Glu Ser Glu Pro Glu Glu
                160                 165                 170 ccg tct ggt gtg gag ggt gca gct ttt caa agc cga ctt ccc cat gac       699
Pro Ser Gly Val Glu Gly Ala Ala Phe Gln Ser Arg Leu Pro His Asp
            175                 180                 185 cga atg acc tct cag gaa gca gcc tgt ttc cca gac atc atc agt ggg       747
Arg Met Thr Ser Gln Glu Ala Ala Cys Phe Pro Asp Ile Ile Ser Gly
        190                 195                 200 cct cag cag aca cag aag gtt ttt ctg ttc atc agg aat cgc aca ttg       795
Pro Gln Gln Thr Gln Lys Val Phe Leu Phe Ile Arg Asn Arg Thr Leu
    205                 210                 215
```

```
                                                            -continued cag tta tgg ctg gac aac cca aag atc cag ctg acg ttt gaa gcc act       843
Gln Leu Trp Leu Asp Asn Pro Lys Ile Gln Leu Thr Phe Glu Ala Thr
220             225                 230                 235 ctc cag cag ctg gaa gcg cct tac aac agc gat act gtg ctt gtc cac       891
Leu Gln Gln Leu Glu Ala Pro Tyr Asn Ser Asp Thr Val Leu Val His
                240                 245                 250 cga gtt cac agt tac tta gag cgc cat ggt ctt atc aac ttc ggc atc       939
Arg Val His Ser Tyr Leu Glu Arg His Gly Leu Ile Asn Phe Gly Ile
            255                 260                 265 tac aag agg ata aaa ccc tta cca att aaa aag aca gga aag gtg att       987
Tyr Lys Arg Ile Lys Pro Leu Pro Ile Lys Lys Thr Gly Lys Val Ile
        270                 275                 280 att ata ggt tca ggt gtt tct ggc ttg gca gca gct cga cag cta cag      1035
Ile Ile Gly Ser Gly Val Ser Gly Leu Ala Ala Ala Arg Gln Leu Gln
    285                 290                 295 agt ttt ggg atg gat gtc aca ctt ctg gaa gcc agg gat cga gta ggt      1083
Ser Phe Gly Met Asp Val Thr Leu Leu Glu Ala Arg Asp Arg Val Gly
300                 305                 310                 315 gga cga gtt gct aca ttt cga aaa gga aac tat gta gct gat ctt ggc      1131
Gly Arg Val Ala Thr Phe Arg Lys Gly Asn Tyr Val Ala Asp Leu Gly
                320                 325                 330 gcc atg gtt gta aca ggt ctt gga ggg aat ccc atg gct gtc gtc agc      1179
Ala Met Val Val Thr Gly Leu Gly Gly Asn Pro Met Ala Val Val Ser
            335                 340                 345 aaa caa gta aat atg gaa ctg gcc aag atc aag caa aaa tgc cca ctt      1227
Lys Gln Val Asn Met Glu Leu Ala Lys Ile Lys Gln Lys Cys Pro Leu
        350                 355                 360 tat gaa gcc aat gga caa gct gtt cca aaa gaa aaa gat gaa atg gta      1275
Tyr Glu Ala Asn Gly Gln Ala Val Pro Lys Glu Lys Asp Glu Met Val
    365                 370                 375 gaa caa gaa ttt aac cgg ttg cta gaa gcc act tct tac ctt agt cac      1323
Glu Gln Glu Phe Asn Arg Leu Leu Glu Ala Thr Ser Tyr Leu Ser His
380                 385                 390                 395 cag tta gac ttc aac gtc ctc aat aat aaa cct gta tcc ctt ggc cag      1371
Gln Leu Asp Phe Asn Val Leu Asn Asn Lys Pro Val Ser Leu Gly Gln
                400                 405                 410 gca ttg gag gtt gtc att cag ctg caa gaa aag cat gtc aaa gat gag      1419
Ala Leu Glu Val Val Ile Gln Leu Gln Glu Lys His Val Lys Asp Glu
            415                 420                 425 cag att gaa cat tgg aag aag ata gtg aaa act cag gag gag ttg aaa      1467
Gln Ile Glu His Trp Lys Lys Ile Val Lys Thr Gln Glu Glu Leu Lys
        430                 435                 440 gag ctt ctt aat aag atg gta aat ttg aag gag aaa att aaa gag ctc      1515
Glu Leu Leu Asn Lys Met Val Asn Leu Lys Glu Lys Ile Lys Glu Leu
    445                 450                 455 cat cag caa tac aaa gaa gct tca gaa gtg aag ccg ccc aga gat atc      1563
His Gln Gln Tyr Lys Glu Ala Ser Glu Val Lys Pro Pro Arg Asp Ile
460                 465                 470                 475 aca gcc gag ttc ctg gtg aag agc aag cac agg gac ctg act gcc ctc      1611
Thr Ala Glu Phe Leu Val Lys Ser Lys His Arg Asp Leu Thr Ala Leu
                480                 485                 490 tgc aag gaa tat gat gaa tta gct gaa aca caa gga aag cta gaa gaa      1659
Cys Lys Glu Tyr Asp Glu Leu Ala Glu Thr Gln Gly Lys Leu Glu Glu
            495                 500                 505 aaa ctt caa gaa ttg gaa gcc aat ccc cca agt gat gta tac ctc tca      1707
Lys Leu Gln Glu Leu Glu Ala Asn Pro Pro Ser Asp Val Tyr Leu Ser
        510                 515                 520 tca aga gac aga caa ata ctt gac tgg cat ttt gca aat ctt gaa ttt      1755
Ser Arg Asp Arg Gln Ile Leu Asp Trp His Phe Ala Asn Leu Glu Phe
    525                 530                 535
```

```
gcc aac gcc aca cct ctc tct acc ctc tct ctt aaa cat tgg gat cag   1803
Ala Asn Ala Thr Pro Leu Ser Thr Leu Ser Leu Lys His Trp Asp Gln
540                 545                 550                 555 gat gat gac ttt gag ttt act gga agc cac ctg aca gta agg aat ggc   1851
Asp Asp Asp Phe Glu Phe Thr Gly Ser His Leu Thr Val Arg Asn Gly
                        560                 565                 570 tac tca tgt gtg cct gtg gct tta gct gaa ggc ttg gac att aaa ctg   1899
Tyr Ser Cys Val Pro Val Ala Leu Ala Glu Gly Leu Asp Ile Lys Leu
            575                 580                 585 aac aca gca gtg cgg cag gtt cgc tac aca gcc tca gga tgt gaa gtg   1947
Asn Thr Ala Val Arg Gln Val Arg Tyr Thr Ala Ser Gly Cys Glu Val
        590                 595                 600 att gct gtg aac aca cgt tcc aca agt caa acc ttt att tat aag tgt   1995
Ile Ala Val Asn Thr Arg Ser Thr Ser Gln Thr Phe Ile Tyr Lys Cys
605                 610                 615 gat gca gtt ctc tgt aca ctt cct ttg gga gtg ttg aag cag cag cca   2043
Asp Ala Val Leu Cys Thr Leu Pro Leu Gly Val Leu Lys Gln Gln Pro
620                 625                 630                 635 cca gct gtt cag ttt gtg cca cct ctt cct gag tgg aaa aca tct gca   2091
Pro Ala Val Gln Phe Val Pro Pro Leu Pro Glu Trp Lys Thr Ser Ala
                640                 645                 650 gtc caa agg atg gga ttt ggc aac ctt aac aag gtg gtg tta tgc ttt   2139
Val Gln Arg Met Gly Phe Gly Asn Leu Asn Lys Val Val Leu Cys Phe
            655                 660                 665 gac cgt gtg ttc tgg gac cca agt gtc aat ttg ttt ggg cac gtt ggc   2187
Asp Arg Val Phe Trp Asp Pro Ser Val Asn Leu Phe Gly His Val Gly
        670                 675                 680 agt aca act gct agc agg ggt gag ctc ttc ctc ttc tgg aac cta tat   2235
Ser Thr Thr Ala Ser Arg Gly Glu Leu Phe Leu Phe Trp Asn Leu Tyr
685                 690                 695 aaa gct cca ata cta ttg gcc ctg gta gca gga gaa gct gct ggc att   2283
Lys Ala Pro Ile Leu Leu Ala Leu Val Ala Gly Glu Ala Ala Gly Ile
700                 705                 710                 715 atg gag aac att agt gat gat gtg att gtc ggc cgg tgc ctg gcc att   2331
Met Glu Asn Ile Ser Asp Asp Val Ile Val Gly Arg Cys Leu Ala Ile
                720                 725                 730 ctc aaa ggg att ttt ggc agc agt gca gtc cca cag ccc aag gaa act   2379
Leu Lys Gly Ile Phe Gly Ser Ser Ala Val Pro Gln Pro Lys Glu Thr
            735                 740                 745 gtg gta tct cgt tgg cgt gct gat ccg tgg gcc cgg ggc tcc tat tct   2427
Val Val Ser Arg Trp Arg Ala Asp Pro Trp Ala Arg Gly Ser Tyr Ser
        750                 755                 760 tat gtg gct gca gga tcc tct gga aat gac tat gat tta atg gct cag   2475
Tyr Val Ala Ala Gly Ser Ser Gly Asn Asp Tyr Asp Leu Met Ala Gln
765                 770                 775 ccg atc act cct ggc ccc tca att cca ggt gcc cca cag cca atc cca   2523
Pro Ile Thr Pro Gly Pro Ser Ile Pro Gly Ala Pro Gln Pro Ile Pro
780                 785                 790                 795 aga ctc ttc ttt gct gga gaa cac aca atc cgg aac tac cca gct aca   2571
Arg Leu Phe Phe Ala Gly Glu His Thr Ile Arg Asn Tyr Pro Ala Thr
                800                 805                 810 gtc cat ggt gct ctg ttg agt ggg ctt cga gaa gca gga agg att gcc   2619
Val His Gly Ala Leu Leu Ser Gly Leu Arg Glu Ala Gly Arg Ile Ala
            815                 820                 825 gac cag ttt ttg gga gcc atg tac act ttg cct cgt cag gcc aca cca   2667
Asp Gln Phe Leu Gly Ala Met Tyr Thr Leu Pro Arg Gln Ala Thr Pro
        830                 835                 840 ggt gtc cct gca cag cag tcc cca agt atg tga gacagatggt tctgaacaga  2720
Gly Val Pro Ala Gln Gln Ser Pro Ser Met
```

```
            845            850
gagatccaac ggcatgtcat ctgccacgta agcaagctct tctagcaata ctagatccta    2780
ctgagaaact ccatgtcatc agctactggg actcctagtt tgacagcaga ggctggctcc    2840
tttggctgac agcaacttac ccattgattt ggaagtacag ctccataaag actgctcgag    2900
aagcaagtgg tgtgagataa cctcttagtc tatggtgttt gtttgttttt gttttttttt    2960
aatatatttt gagaataaaa ctttaaaata attttatatg aaatttatt tttaaaaaaa     3020 aaaaaaaaaa                                                           3030
```

<210> SEQ ID NO 5
<211> LENGTH: 853
<212> TYPE: PRT
<213> ORGANISM: mus musculus

<400> SEQUENCE: 5

```
Met Leu Ser Gly Lys Lys Ala Ala Ala Ala Ala Ala Ala Ala Ala
1               5                   10                  15

Ala Ala Ala Ala Gly Thr Glu Ala Ser Gly Ala Ala Gly Gly Ala
                20                  25                  30

Glu Asn Gly Ser Glu Val Ala Ala Pro Pro Ala Gly Leu Thr Gly Pro
                35                  40                  45

Thr Asp Met Ala Thr Gly Ala Ala Gly Glu Arg Thr Pro Arg Lys Lys
50                  55                  60

Glu Pro Pro Arg Ala Ser Pro Pro Gly Gly Leu Ala Glu Pro Pro Gly
65                  70                  75                  80

Ser Ala Gly Pro Gln Ala Gly Pro Thr Ala Gly Pro Gly Ser Ala Thr
                85                  90                  95

Pro Met Glu Thr Gly Ile Ala Glu Thr Pro Glu Gly Arg Arg Thr Ser
                100                 105                 110

Arg Arg Lys Arg Ala Lys Val Glu Tyr Arg Glu Met Asp Glu Ser Leu
                115                 120                 125

Ala Asn Leu Ser Glu Asp Glu Tyr Tyr Ser Glu Glu Glu Arg Asn Ala
130                 135                 140

Lys Ala Glu Lys Glu Lys Lys Leu Pro Pro Pro Pro Gln Ala Pro
145                 150                 155                 160

Pro Glu Glu Glu Asn Glu Ser Glu Pro Glu Glu Pro Ser Gly Val Glu
                165                 170                 175

Gly Ala Ala Phe Gln Ser Arg Leu Pro His Asp Arg Met Thr Ser Gln
                180                 185                 190

Glu Ala Ala Cys Phe Pro Asp Ile Ile Ser Gly Pro Gln Gln Thr Gln
                195                 200                 205

Lys Val Phe Leu Phe Ile Arg Asn Arg Thr Leu Gln Leu Trp Leu Asp
                210                 215                 220

Asn Pro Lys Ile Gln Leu Thr Phe Glu Ala Thr Leu Gln Gln Leu Glu
225                 230                 235                 240

Ala Pro Tyr Asn Ser Asp Thr Val Leu Val His Arg Val His Ser Tyr
                245                 250                 255

Leu Glu Arg His Gly Leu Ile Asn Phe Gly Ile Tyr Lys Arg Ile Lys
                260                 265                 270

Pro Leu Pro Ile Lys Lys Thr Gly Lys Val Ile Ile Ile Gly Ser Gly
                275                 280                 285

Val Ser Gly Leu Ala Ala Ala Arg Gln Leu Gln Ser Phe Gly Met Asp
                290                 295                 300
```

-continued

```
Val Thr Leu Leu Glu Ala Arg Asp Arg Val Gly Gly Arg Val Ala Thr
305                 310                 315                 320

Phe Arg Lys Gly Asn Tyr Val Ala Asp Leu Gly Ala Met Val Val Thr
                325                 330                 335

Gly Leu Gly Gly Asn Pro Met Ala Val Val Ser Lys Gln Val Asn Met
                340                 345                 350

Glu Leu Ala Lys Ile Lys Gln Lys Cys Pro Leu Tyr Glu Ala Asn Gly
                355                 360                 365

Gln Ala Val Pro Lys Glu Lys Asp Glu Met Val Gln Glu Phe Asn
    370                 375                 380

Arg Leu Leu Glu Ala Thr Ser Tyr Leu Ser His Gln Leu Asp Phe Asn
385                 390                 395                 400

Val Leu Asn Asn Lys Pro Val Ser Leu Gly Gln Ala Leu Glu Val Val
                405                 410                 415

Ile Gln Leu Gln Glu Lys His Val Lys Asp Glu Gln Ile Glu His Trp
                420                 425                 430

Lys Lys Ile Val Lys Thr Gln Glu Glu Leu Lys Glu Leu Leu Asn Lys
                435                 440                 445

Met Val Asn Leu Lys Glu Lys Ile Lys Glu Leu His Gln Gln Tyr Lys
450                 455                 460

Glu Ala Ser Glu Val Lys Pro Pro Arg Asp Ile Thr Ala Glu Phe Leu
465                 470                 475                 480

Val Lys Ser Lys His Arg Asp Leu Thr Ala Leu Cys Lys Glu Tyr Asp
                485                 490                 495

Glu Leu Ala Glu Thr Gln Gly Lys Leu Glu Glu Lys Leu Gln Glu Leu
                500                 505                 510

Glu Ala Asn Pro Pro Ser Asp Val Tyr Leu Ser Ser Arg Asp Arg Gln
                515                 520                 525

Ile Leu Asp Trp His Phe Ala Asn Leu Glu Phe Ala Asn Ala Thr Pro
                530                 535                 540

Leu Ser Thr Leu Ser Leu Lys His Trp Asp Gln Asp Asp Asp Phe Glu
545                 550                 555                 560

Phe Thr Gly Ser His Leu Thr Val Arg Asn Gly Tyr Ser Cys Val Pro
                565                 570                 575

Val Ala Leu Ala Glu Gly Leu Asp Ile Lys Leu Asn Thr Ala Val Arg
                580                 585                 590

Gln Val Arg Tyr Thr Ala Ser Gly Cys Glu Val Ile Ala Val Asn Thr
                595                 600                 605

Arg Ser Thr Ser Gln Thr Phe Ile Tyr Lys Cys Asp Ala Val Leu Cys
                610                 615                 620

Thr Leu Pro Leu Gly Val Leu Lys Gln Gln Pro Pro Ala Val Gln Phe
625                 630                 635                 640

Val Pro Pro Leu Pro Glu Trp Lys Thr Ser Ala Val Gln Arg Met Gly
                645                 650                 655

Phe Gly Asn Leu Asn Lys Val Val Leu Cys Phe Asp Arg Val Phe Trp
                660                 665                 670

Asp Pro Ser Val Asn Leu Phe Gly His Val Gly Ser Thr Thr Ala Ser
                675                 680                 685

Arg Gly Glu Leu Phe Leu Phe Trp Asn Leu Tyr Lys Ala Pro Ile Leu
                690                 695                 700

Leu Ala Leu Val Ala Gly Glu Ala Ala Gly Ile Met Glu Asn Ile Ser
705                 710                 715                 720

Asp Asp Val Ile Val Gly Arg Cys Leu Ala Ile Leu Lys Gly Ile Phe
```

```
                   725                 730                 735
Gly Ser Ser Ala Val Pro Gln Pro Lys Glu Thr Val Val Ser Arg Trp
            740                 745                 750

Arg Ala Asp Pro Trp Ala Arg Gly Ser Tyr Ser Tyr Val Ala Ala Gly
        755                 760                 765

Ser Ser Gly Asn Asp Tyr Asp Leu Met Ala Gln Pro Ile Thr Pro Gly
    770                 775                 780

Pro Ser Ile Pro Gly Ala Pro Gln Pro Ile Pro Arg Leu Phe Phe Ala
785                 790                 795                 800

Gly Glu His Thr Ile Arg Asn Tyr Pro Ala Thr Val His Gly Ala Leu
                805                 810                 815

Leu Ser Gly Leu Arg Glu Ala Gly Arg Ile Ala Asp Gln Phe Leu Gly
            820                 825                 830

Ala Met Tyr Thr Leu Pro Arg Gln Ala Thr Pro Gly Val Pro Ala Gln
        835                 840                 845

Gln Ser Pro Ser Met
    850

<210> SEQ ID NO 6
<211> LENGTH: 8717
<212> TYPE: DNA
<213> ORGANISM: artificial sequence
<220> FEATURE:
<223> OTHER INFORMATION: pBS-ROSA26-AOF2
<220> FEATURE:
<221> NAME/KEY: promoter
<222> LOCATION: (625)..(645)
<223> OTHER INFORMATION: T7 promoter
<220> FEATURE:
<221> NAME/KEY: misc_feature
<222> LOCATION: (1018)..(1381)
<223> OTHER INFORMATION: HS4 insulator
<220> FEATURE:
<221> NAME/KEY: promoter
<222> LOCATION: (1414)..(2225)
<223> OTHER INFORMATION: ROSA26 promoter
<220> FEATURE:
<221> NAME/KEY: Intron
<222> LOCATION: (2311)..(2878)
<223> OTHER INFORMATION: rabbit beta-globin intron
<220> FEATURE:
<221> NAME/KEY: misc_feature
<222> LOCATION: (3079)..(3106)
<223> OTHER INFORMATION: sequence encoding FLAG tag
<220> FEATURE:
<221> NAME/KEY: CDS
<222> LOCATION: (3079)..(5667)
<220> FEATURE:
<221> NAME/KEY: misc_feature
<222> LOCATION: (3112)..(5667)
<223> OTHER INFORMATION: seqence encoding human LSD1
<220> FEATURE:
<221> NAME/KEY: polyA_site
<222> LOCATION: (5686)..(5819)
<223> OTHER INFORMATION: SV40 poly A site
<220> FEATURE:
<221> NAME/KEY: misc_feature
<222> LOCATION: (5896)..(6434)
<223> OTHER INFORMATION: HS4 insulator
<220> FEATURE:
<221> NAME/KEY: misc_feature
<222> LOCATION: (6914)..(7581)
<223> OTHER INFORMATION: pUC origin
<220> FEATURE:
<221> NAME/KEY: misc_feature
<222> LOCATION: (7729)..(8589)
<223> OTHER INFORMATION: sequence encoding beta-lactamase

<400> SEQUENCE: 6
```

```
ctaaattgta agcgttaata ttttgttaaa attcgcgtta aattttttgtt aaatcagctc      60 attttttaac caataggccg aaatcggcaa aatcccttat aaatcaaaag aatagaccga     120 gataggggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaagggag     300
cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tgggtaccgg     660
gccccccctc gaggtcgacg gtatcgataa gcttgattcg agctctgtac atgtccgcgg     720
tcgcgacgta cgcgtatcga tggcgccagc tgcaggcggc cgccatatgc atcctaggcc     780
tattaatatt ccggagtata cgtagccggc taacgttaac aaccggtacc gagttggcgc     840
gcctgggagc tcacggggac agccccccc caaagccccc aggggatgtaa ttacgtccct     900 cccccgctag ggggcagcag cgagccgccc ggggctccgc tccggtccgg cgctccccc     960 gcatccccga gccggcagcg tgcggggaca gcccgggcac ggggaaggtg gcacgggatc    1020
gctttcctct gaacgcttct cgctgctctt tgagcctgca gacacctggg gggatacggg    1080
gaaaaagctt taggctgaaa gagagattta gaatgacggg cgcgcctggg agctcacggg    1140
gacagccccc ccccaaagcc cccagggatg taattacgtc cctccccccgc taggggggcag    1200 cagcgagccg cccggggctc cgctccggtc cggcgctccc ccgcatccc cgagccggca    1260 gcgtgcgggg acagcccggg cacggggaag gtggcacggg atcgcttttcc tctgaacgct    1320 tctcgctgct ctttgagcct gcagacacct ggggggatac ggggaaaaag ctgggcgcgc    1380
caattaaccc tcactaaagg gggtacctct agtcgactag atgaaggaga gccttttctct    1440 ctgggcaaga gcggtgcaat ggtgtgtaaa ggtagctgag aagacgaaaa gggcaagcat    1500
cttcctgcta ccaggctggg gaggcccagg cccacgaccc cgaggagagg gaacgcaggg    1560
agactgaggt gacccttctt tccccgggg cccggtcgtg tggttcggtg tctcttttct    1620
gttggaccct taccttgacc caggcgctgc cggggcctgg gccgggctg cggcgcacgg    1680 cactcccggg aggcagcgag actcgagtta ggcccaacgc ggcgccacgg cgtttcctgg    1740
ccgggaatgg cccgtacccg tgaggtgggg gtgggggggca gaaaaggcgg agcgagcccg    1800
aggcggggag gggagggcc aggggcgag gggccggca ctactgtgtt ggcggactgg    1860
cgggactagg gctgcgtgag tctctgagcg caggcgggcg gcggccgccc ctcccccggc    1920
ggcggcagcg gcggcagcgg cggcagctca ctcagcccgc tgcccgagcg gaaacgccac    1980
tgaccgcacg gggattccca gtgccggcgc caggggcacg cgggacacgc cccctcccgc    2040
cgcgccattg gcctctccgc ccaccgcccc acacttattg gccggtgcgc cgccaatcag    2100
cggaggctgc cggggccgcc taaagaagag gctgtgcttt gggctccgg ctcctcagag    2160 agcctcggct aggtagggga tcgggactct ggcgggaggg cggcttggtg cgtttgcggg    2220
gatccactag ttctagaact atagctagca tgcgcaaatt taaagcgctg atatcgatcg    2280
cgcgcagatc ctaagaactt ccaggggagg tttgggacc cttgattgtt ctttcttttt    2340
cgctattgta aaattcatgt tatatggagg gggcaaagtt ttcagggtgt tgtttagaat    2400
```

```
gggaagatgt cccttgtatc accatggacc ctcatgataa ttttgtttct ttcactttct    2460
actctgttga caaccattgt ctcctcttat tttcttttca ttttctgtaa cttttcgtt    2520 aaactttagc ttgcatttgt aacgaatttt taaattcact tttgtttatt tgtcagattg    2580
taagtacttt ctctaatcac ttttttttca aggcaatcag ggtatattat attgtacttc    2640
agcacagttt tagagaacaa ttgttataat taaatgataa ggtagaatat ttctgcatat    2700
aaattctggc tggcgtggaa atattcttat tggtagaaac aactcaccc tggtcatcat     2760 cctgcctttc tctttatggt tacaatgata tacactgttt gagatgagga taaaatactc    2820
tgagtccaaa ccgggcccct ctgctaacca tgttcatgcc ttcttctctt tcctacagct    2880
cctgggcaac gtgctggtta tgtgctgtct catcaaatgg caaagaattc atggctggtg    2940
accacgtcgt ggaatgcctt cgaattcagc acctgcacat gggacgtcga cctgaggtaa    3000
ttataacccg ggccctatat atggatccag atcgatcatc aggatcggta ccgggccccc    3060
cctcgagaag cttccacc atg gac tac aag gac gac gat gac aag gaa ttc      3111
                     Met Asp Tyr Lys Asp Asp Asp Asp Lys Glu Phe
                      1               5                      10 tta tct ggg aag aag gcg gca gcc gcg gcg gcg gcg gct gca gcg gca      3159
Leu Ser Gly Lys Lys Ala Ala Ala Ala Ala Ala Ala Ala Ala Ala Ala
             15                  20                  25 gca acc ggg acg gag gct ggc cct ggg aca gca ggc ggc tcc gag aac      3207
Ala Thr Gly Thr Glu Ala Gly Pro Gly Thr Ala Gly Gly Ser Glu Asn
         30                  35                  40 ggg tct gag gtg gcc gcg cag ccc gcg ggc ctg tcg ggc cca gcc gag      3255
Gly Ser Glu Val Ala Ala Gln Pro Ala Gly Leu Ser Gly Pro Ala Glu
 45                  50                  55 gtc ggg ccg ggg gcg gtg ggg gag cgc aca ccc cgc aag aaa gag cct      3303
Val Gly Pro Gly Ala Val Gly Glu Arg Thr Pro Arg Lys Lys Glu Pro
 60                  65                  70                  75 ccg cgg gcc tcg ccc ccc ggg ggc ctg gcg gaa ccg ccg ggg tcc gca      3351
Pro Arg Ala Ser Pro Pro Gly Gly Leu Ala Glu Pro Pro Gly Ser Ala
                 80                  85                  90 ggg cct cag gcc ggc cct act gtc gtg cct ggg tct gcg acc ccc atg      3399
Gly Pro Gln Ala Gly Pro Thr Val Val Pro Gly Ser Ala Thr Pro Met
                 95                 100                 105 gaa act gga ata gca gag act ccg gag ggg cgt cgg acc agc cgg cgc      3447
Glu Thr Gly Ile Ala Glu Thr Pro Glu Gly Arg Arg Thr Ser Arg Arg
             110                 115                 120 aag cgg gcg aag gta gag tac aga gag atg gat gaa agc ttg gcc aac      3495
Lys Arg Ala Lys Val Glu Tyr Arg Glu Met Asp Glu Ser Leu Ala Asn
 125                 130                 135 ctc tca gaa gat gag tat tat tca gaa gaa gag aga aat gcc aaa gca      3543
Leu Ser Glu Asp Glu Tyr Tyr Ser Glu Glu Glu Arg Asn Ala Lys Ala
140                 145                 150                 155 gag aag gaa aag aag ctt ccc cca cca ccc cct caa gcc cca cct gag      3591
Glu Lys Glu Lys Lys Leu Pro Pro Pro Pro Pro Gln Ala Pro Pro Glu
                 160                 165                 170 gaa gaa aat gaa agt gag cct gaa gaa cca tcg ggt gtg gag ggc gca      3639
Glu Glu Asn Glu Ser Glu Pro Glu Glu Pro Ser Gly Val Glu Gly Ala
             175                 180                 185 gct ttc cag agc cga ctt cct cat gac cgg atg act tct caa gaa gca      3687
Ala Phe Gln Ser Arg Leu Pro His Asp Arg Met Thr Ser Gln Glu Ala
             190                 195                 200 gcc tgt ttt cca gat att atc agt gga cca caa cag acc cag aag gtt      3735
Ala Cys Phe Pro Asp Ile Ile Ser Gly Pro Gln Gln Thr Gln Lys Val
 205                 210                 215
```

-continued

| | | |
|---|---|---|
| ttt ctt ttc att aga aac cgc aca ctg cag ttg tgg ttg gat aat cca<br>Phe Leu Phe Ile Arg Asn Arg Thr Leu Gln Leu Trp Leu Asp Asn Pro<br>220                        225                      230                     235 | 3783 |
| aag att cag ctg aca ttt gag gct act ctc caa caa tta gaa gca cct<br>Lys Ile Gln Leu Thr Phe Glu Ala Thr Leu Gln Gln Leu Glu Ala Pro<br>               240                      245                      250 | 3831 |
| tat aac agt gat act gtg ctt gtc cac cga gtt cac agt tat tta gag<br>Tyr Asn Ser Asp Thr Val Leu Val His Arg Val His Ser Tyr Leu Glu<br>                      255                      260                     265 | 3879 |
| cgt cat ggt ctt atc aac ttc ggc atc tat aag agg ata aaa ccc cta<br>Arg His Gly Leu Ile Asn Phe Gly Ile Tyr Lys Arg Ile Lys Pro Leu<br>        270                      275                      280 | 3927 |
| cca act aaa aag aca gga aag gta att att ata ggc tct ggg gtc tca<br>Pro Thr Lys Lys Thr Gly Lys Val Ile Ile Ile Gly Ser Gly Val Ser<br>     285                      290                      295 | 3975 |
| ggc ttg gca gca gct cga cag tta caa agt ttt gga atg gat gtc aca<br>Gly Leu Ala Ala Ala Arg Gln Leu Gln Ser Phe Gly Met Asp Val Thr<br>300                        305                      310                     315 | 4023 |
| ctt ttg gaa gcc agg gat cgt gtg ggt gga cga gtt gcc aca ttt cgc<br>Leu Leu Glu Ala Arg Asp Arg Val Gly Gly Arg Val Ala Thr Phe Arg<br>               320                      325                      330 | 4071 |
| aaa gga aac tat gta gct gat ctt gga gcc atg gtg gta aca ggt ctt<br>Lys Gly Asn Tyr Val Ala Asp Leu Gly Ala Met Val Val Thr Gly Leu<br>                      335                      340                     345 | 4119 |
| gga ggg aat cct atg gct gtg gtc agc aaa caa gta aat atg gaa ctg<br>Gly Gly Asn Pro Met Ala Val Val Ser Lys Gln Val Asn Met Glu Leu<br>        350                      355                      360 | 4167 |
| gcc aag atc aag caa aaa tgc cca ctt tat gaa gcc aac gga caa gct<br>Ala Lys Ile Lys Gln Lys Cys Pro Leu Tyr Glu Ala Asn Gly Gln Ala<br>     365                      370                      375 | 4215 |
| gtt cct aaa gag aaa gat gaa atg gta gag caa gag ttt aac cgg ttg<br>Val Pro Lys Glu Lys Asp Glu Met Val Glu Gln Glu Phe Asn Arg Leu<br>380                        385                      390                     395 | 4263 |
| cta gaa gct aca tct tac ctt agt cat caa cta gac ttc aat gtc ctc<br>Leu Glu Ala Thr Ser Tyr Leu Ser His Gln Leu Asp Phe Asn Val Leu<br>               400                      405                     410 | 4311 |
| aat aat aag cct gtg tcc ctt ggc cag gca ttg gaa gtt gtc att cag<br>Asn Asn Lys Pro Val Ser Leu Gly Gln Ala Leu Glu Val Val Ile Gln<br>                      415                      420                     425 | 4359 |
| tta caa gag aag cat gtc aaa gat gag cag att gaa cat tgg aag aag<br>Leu Gln Glu Lys His Val Lys Asp Glu Gln Ile Glu His Trp Lys Lys<br>        430                      435                      440 | 4407 |
| ata gtg aaa act cag gaa gaa ttg aaa gaa ctt ctt aat aag atg gta<br>Ile Val Lys Thr Gln Glu Glu Leu Lys Glu Leu Leu Asn Lys Met Val<br>     445                      450                      455 | 4455 |
| aat ttg aaa gag aaa att aaa gaa ctc cat cag caa tac aaa gaa gca<br>Asn Leu Lys Glu Lys Ile Lys Glu Leu His Gln Gln Tyr Lys Glu Ala<br>460                        465                      470                     475 | 4503 |
| tct gaa gta aag cca ccc aga gat att act gcc gag ttc tta gtg aaa<br>Ser Glu Val Lys Pro Pro Arg Asp Ile Thr Ala Glu Phe Leu Val Lys<br>               480                      485                     490 | 4551 |
| agc aaa cac agg gat ctg acc gcc cta tgc aag gaa tat gat gaa tta<br>Ser Lys His Arg Asp Leu Thr Ala Leu Cys Lys Glu Tyr Asp Glu Leu<br>                      495                      500                     505 | 4599 |
| gct gaa aca caa gga aag cta gaa gaa aaa ctt cag gag ttg gaa gcg<br>Ala Glu Thr Gln Gly Lys Leu Glu Glu Lys Leu Gln Glu Leu Glu Ala<br>        510                      515                      520 | 4647 |
| aat ccc cca agt gat gta tat ctc tca tca aga gac aga caa ata ctt<br>Asn Pro Pro Ser Asp Val Tyr Leu Ser Ser Arg Asp Arg Gln Ile Leu<br>     525                      530                      535 | 4695 |

| | | |
|---|---|---|
| gat tgg cat ttt gca aat ctt gaa ttt gct aat gcc aca cct ctc tca<br>Asp Trp His Phe Ala Asn Leu Glu Phe Ala Asn Ala Thr Pro Leu Ser<br>540                       545                     550                    555 | 4743 |
| act ctc tcc ctt aag cac tgg gat cag gat gat gac ttt gag ttc act<br>Thr Leu Ser Leu Lys His Trp Asp Gln Asp Asp Asp Phe Glu Phe Thr<br>                            560                     565                     570 | 4791 |
| ggc agc cac ctg aca gta agg aat ggc tac tcg tgt gtg cct gtg gct<br>Gly Ser His Leu Thr Val Arg Asn Gly Tyr Ser Cys Val Pro Val Ala<br>               575                     580                     585 | 4839 |
| tta gca gaa ggc cta gac att aaa ctg aat aca gca gtg cga cag gtt<br>Leu Ala Glu Gly Leu Asp Ile Lys Leu Asn Thr Ala Val Arg Gln Val<br>            590                     595                     600 | 4887 |
| cgc tac acg gct tca gga tgt gaa gtg ata gct gtg aat acc cgc tcc<br>Arg Tyr Thr Ala Ser Gly Cys Glu Val Ile Ala Val Asn Thr Arg Ser<br>605                       610                     615 | 4935 |
| acg agt caa acc ttt att tat aaa tgc gac gca gtt ctc tgt acc ctt<br>Thr Ser Gln Thr Phe Ile Tyr Lys Cys Asp Ala Val Leu Cys Thr Leu<br>620                       625                     630                     635 | 4983 |
| ccc ctg ggt gtg ctg aag cag cag cca cca gcc gtt cag ttt gtg cca<br>Pro Leu Gly Val Leu Lys Gln Gln Pro Pro Ala Val Gln Phe Val Pro<br>                            640                     645                     650 | 5031 |
| cct ctc cct gag tgg aaa aca tct gca gtc caa agg atg gga ttt ggc<br>Pro Leu Pro Glu Trp Lys Thr Ser Ala Val Gln Arg Met Gly Phe Gly<br>               655                     660                     665 | 5079 |
| aac ctt aac aag gtg gtg ttg tgt ttt gat cgg gtg ttc tgg gat cca<br>Asn Leu Asn Lys Val Val Leu Cys Phe Asp Arg Val Phe Trp Asp Pro<br>            670                     675                     680 | 5127 |
| agt gtc aat ttg ttc ggg cat gtt ggc agt acg act gcc agc agg ggt<br>Ser Val Asn Leu Phe Gly His Val Gly Ser Thr Thr Ala Ser Arg Gly<br>685                       690                     695 | 5175 |
| gag ctc ttc ctc ttc tgg aac ctc tat aaa gct cca ata ctg ttg gca<br>Glu Leu Phe Leu Phe Trp Asn Leu Tyr Lys Ala Pro Ile Leu Leu Ala<br>700                       705                     710                     715 | 5223 |
| cta gtg gca gga gaa gct gct ggt atc atg gaa aac ata agt gac gat<br>Leu Val Ala Gly Glu Ala Ala Gly Ile Met Glu Asn Ile Ser Asp Asp<br>                            720                     725                     730 | 5271 |
| gtg att gtt ggc cga tgc ctg gcc att ctc aaa ggg att ttt ggt agc<br>Val Ile Val Gly Arg Cys Leu Ala Ile Leu Lys Gly Ile Phe Gly Ser<br>               735                     740                     745 | 5319 |
| agt gca gta cct cag ccc aaa gaa act gtg gtg tct cgt tgg cgt gct<br>Ser Ala Val Pro Gln Pro Lys Glu Thr Val Val Ser Arg Trp Arg Ala<br>            750                     755                     760 | 5367 |
| gat ccc tgg gct cgg ggc tct tat tcc tat gtt gct gca gga tca tct<br>Asp Pro Trp Ala Arg Gly Ser Tyr Ser Tyr Val Ala Ala Gly Ser Ser<br>765                       770                     775 | 5415 |
| gga aat gac tat gat tta atg gct cag cca atc act cct ggc ccc tcg<br>Gly Asn Asp Tyr Asp Leu Met Ala Gln Pro Ile Thr Pro Gly Pro Ser<br>780                       785                     790                     795 | 5463 |
| att cca ggt gcc cca cag ccg att cca cga ctc ttc ttt gcg gga gaa<br>Ile Pro Gly Ala Pro Gln Pro Ile Pro Arg Leu Phe Phe Ala Gly Glu<br>                            800                     805                     810 | 5511 |
| cat acg atc cgt aac tac cca gcc aca gtg cat ggt gct ctg ctg agt<br>His Thr Ile Arg Asn Tyr Pro Ala Thr Val His Gly Ala Leu Leu Ser<br>               815                     820                     825 | 5559 |
| ggg ctg cga gaa gcg gga aga att gca gac cag ttt ttg ggg gcc atg<br>Gly Leu Arg Glu Ala Gly Arg Ile Ala Asp Gln Phe Leu Gly Ala Met<br>            830                     835                     840 | 5607 |
| tat acg ctg cct cgc cag gcc aca cca ggt gtt cct gca cag cag tcc<br>Tyr Thr Leu Pro Arg Gln Ala Thr Pro Gly Val Pro Ala Gln Gln Ser | 5655 |

|     |     |     |     |     |
| --- | --- | --- | --- | --- |
| 845 | | 850 | | 855 |

| | | |
|---|---|---|
| cca agc atg tga gctaggatct tattaaagca gaacttgttt attgcagctt | | 5707 |
| Pro Ser Met | | |
| 860 | | |

| | |
|---|---|
| ataatggtta caaataaagc aatagcatca caaatttcac aaataaagca ttttttttcac | 5767 |
| tgcattctag ttgtggtttg tccaaactca tcaatgtatc ttatcatgtc tggtcgactc | 5827 |
| tagcagtgaa agtctgcaat gaattcgagt tggcgcgcct gtcattctaa atctctcttt | 5887 |
| cagcctaaag cttttccccc gtatccccc aggtgtctgc aggctcaaag agcagcgaga | 5947 |
| agcgttcaga ggaaagcgat cccgtgccac cttcccgtg cccgggctgt ccccgcacgc | 6007 |
| tgccggctcg gggatgcggg gggagcgccg gaccggagcg gagccccggg cggctcgctg | 6067 |
| ctgcccccta gcggggagg gacgtaatta catccctggt gggctttggg aggggggctg | 6127 |
| tccccgtgag ctcccaggcg cgcctgtcat tctaaatctc tctttcagcc taaagctttt | 6187 |
| tccccgtatc cccccaggtg tctgcaggct caaagagcag cgagaagcgt tcagaggaaa | 6247 |
| gcgatcccgt gccaccttcc ccgtgccgg ctgtcccg cacgctgccg gctcggggat | 6307 |
| gcgggggag cgccggaccg gagcggagcc ccgggcggct cgctgctgcc cctagcggg | 6367 |
| ggagggacgt aattacatcc ctgggggctt tgggggggg ctgtccccgt gagctcccag | 6427 |
| gcgcgccaac tcgctagagg taccggttgt taacgttagc cggctacgta tactccggaa | 6487 |
| tattaatagg cctaggatgc atatggcggc cgccaccgcg gtggagctcc agcttttgtt | 6547 |
| gcgcgcttgg cgtaatcatg gtcatagctg tttcctgtgt gaaattgtta tccgctcaca | 6607 |
| attccacaca acatacgagc cggaagcata agtgtaaag cctggggtgc ctaatgagtg | 6667 |
| agctaactca cattaattgc gttgcgctca ctgcccgctt tccagtcggg aaacctgtcg | 6727 |
| tgccagctgc attaatgaat cggccaacgc gcggggagag gcggtttgcg tattgggcgc | 6787 |
| tcttccgctt cctcgctcac tgactcgctg cgctcggtcg ttcggctgcg gcgagcggta | 6847 |
| tcagctcact caaaggcggt aatacggtta tccacagaat caggggataa cgcaggaaag | 6907 |
| aacatgtgag caaaaggcca gcaaaaggcc aggaaccgta aaaaggccgc gttgctggcg | 6967 |
| ttttccata ggctccgccc ccctgacgag catcacaaaa atcgacgctc aagtcagagg | 7027 |
| tggcgaaacc cgacaggact ataaagatac caggcgtttc ccctggaag ctccctcgtg | 7087 |
| cgctctcctg ttccgaccct gccgcttacc ggatacctgt ccgcctttct cccttcggga | 7147 |
| agcgtggcgc tttctcatag ctcacgctgt aggtatctca gttcggtgta ggtcgttcgc | 7207 |
| tccaagctgg gctgtgtgca cgaacccccc gttcagcccg accgctgcgc cttatccggt | 7267 |
| aactatcgtc ttgagtccaa cccggtaaga cacgacttat cgccactggc agcagccact | 7327 |
| ggtaacagga ttagcagagc gaggtatgta ggcggtgcta cagagttctt gaagtggtgg | 7387 |
| cctaactacg gctacactag aaggacagta tttggtatct gcgctctgct gaagccagtt | 7447 |
| accttcggaa aaagagttgg tagctcttga tccggcaaac aaaccaccgc tggtagcggt | 7507 |
| ggtttttttg tttgcaagca gcagattacg cgcagaaaaa aaggatctca agaagatcct | 7567 |
| ttgatctttt ctacggggtc tgacgctcag tggaacgaaa actcacgtta agggattttg | 7627 |
| gtcatgagat tatcaaaaag gatcttcacc tagatccttt taaattaaaa atgaagtttt | 7687 |
| aaatcaatct aaagtatata tgagtaaact tggtctgaca gttaccaatg cttaatcagt | 7747 |
| gaggcaccta tctcagcgat ctgtctattt cgttcatcca tagttgcctg actccccgtc | 7807 |
| gtgtagataa ctacgatacg ggagggctta ccatctggcc ccagtgctgc aatgataccg | 7867 |
| cgagacccac gctcaccggc tccagattta tcagcaataa accagccagc cggaagggcc | 7927 |

-continued

```
gagcgcagaa gtggtcctgc aactttatcc gcctccatcc agtctattaa ttgttgccgg      7987
gaagctagag taagtagttc gccagttaat agtttgcgca acgttgttgc cattgctaca      8047
ggcatcgtgg tgtcacgctc gtcgtttggt atggcttcat tcagctccgg ttcccaacga      8107
tcaaggcgag ttacatgatc ccccatgttg tgcaaaaaag cggttagctc cttcggtcct      8167
ccgatcgttg tcagaagtaa gttggccgca gtgttatcac tcatggttat ggcagcactg      8227
cataattctc ttactgtcat gccatccgta agatgctttt ctgtgactgg tgagtactca      8287
accaagtcat tctgagaata gtgtatgcgg cgaccgagtt gctcttgccc ggcgtcaata      8347
cgggataata ccgcgccaca tagcagaact ttaaaagtgc tcatcattgg aaaacgttct      8407
tcggggcgaa aactctcaag gatcttaccg ctgttgagat ccagttcgat gtaacccact      8467
cgtgcaccca actgatcttc agcatctttt actttcacca gcgtttctgg gtgagcaaaa      8527
acaggaaggc aaaatgccgc aaaaaaggga ataagggcga cacggaaatg ttgaatactc      8587
atactcttcc ttttcaata ttattgaagc atttatcagg gttattgtct catgagcgga       8647
tacatatttg aatgtattta gaaaaataaa caatagggg ttccgcgcac atttccccga       8707
aaagtgccac                                                             8717
```

<210> SEQ ID NO 7
<211> LENGTH: 862
<212> TYPE: PRT
<213> ORGANISM: artificial sequence
<220> FEATURE:
<223> OTHER INFORMATION: Synthetic Construct

<400> SEQUENCE: 7

```
Met Asp Tyr Lys Asp Asp Asp Lys Glu Phe Leu Ser Gly Lys Lys
1               5                   10                  15

Ala Ala Ala Ala Ala Ala Ala Ala Ala Ala Ala Thr Gly Thr Glu
                20                  25                  30

Ala Gly Pro Gly Thr Ala Gly Gly Ser Glu Asn Gly Ser Glu Val Ala
                35                  40                  45

Ala Gln Pro Ala Gly Leu Ser Gly Pro Ala Glu Val Gly Pro Gly Ala
        50                  55                  60

Val Gly Glu Arg Thr Pro Arg Lys Lys Glu Pro Pro Arg Ala Ser Pro
65                  70                  75                  80

Pro Gly Gly Leu Ala Glu Pro Gly Ser Ala Gly Pro Gln Ala Gly
                85                  90                  95

Pro Thr Val Val Pro Gly Ser Ala Thr Pro Met Glu Thr Gly Ile Ala
                100                 105                 110

Glu Thr Pro Glu Gly Arg Arg Thr Ser Arg Arg Lys Arg Ala Lys Val
        115                 120                 125

Glu Tyr Arg Glu Met Asp Glu Ser Leu Ala Asn Leu Ser Glu Asp Glu
    130                 135                 140

Tyr Tyr Ser Glu Glu Arg Asn Ala Lys Ala Glu Lys Glu Lys
145                 150                 155                 160

Leu Pro Pro Pro Pro Gln Ala Pro Pro Glu Glu Asn Glu Ser
                165                 170                 175

Glu Pro Glu Glu Pro Ser Gly Val Glu Gly Ala Ala Phe Gln Ser Arg
                180                 185                 190

Leu Pro His Asp Arg Met Thr Ser Gln Glu Ala Ala Cys Phe Pro Asp
        195                 200                 205

Ile Ile Ser Gly Pro Gln Gln Thr Gln Lys Val Phe Leu Phe Ile Arg
```

-continued

```
            210                 215                 220
Asn Arg Thr Leu Gln Leu Trp Leu Asp Asn Pro Lys Ile Gln Leu Thr
225                 230                 235                 240

Phe Glu Ala Thr Leu Gln Gln Leu Glu Ala Pro Tyr Asn Ser Asp Thr
                245                 250                 255

Val Leu Val His Arg Val His Ser Tyr Leu Glu Arg His Gly Leu Ile
                    260                 265                 270

Asn Phe Gly Ile Tyr Lys Arg Ile Lys Pro Leu Pro Thr Lys Lys Thr
            275                 280                 285

Gly Lys Val Ile Ile Ile Gly Ser Gly Val Ser Gly Leu Ala Ala Ala
            290                 295                 300

Arg Gln Leu Gln Ser Phe Gly Met Asp Val Thr Leu Leu Glu Ala Arg
305                 310                 315                 320

Asp Arg Val Gly Gly Arg Val Ala Thr Phe Arg Lys Gly Asn Tyr Val
                    325                 330                 335

Ala Asp Leu Gly Ala Met Val Val Thr Gly Leu Gly Gly Asn Pro Met
                340                 345                 350

Ala Val Val Ser Lys Gln Val Asn Met Glu Leu Ala Lys Ile Lys Gln
                355                 360                 365

Lys Cys Pro Leu Tyr Glu Ala Asn Gly Gln Ala Val Pro Lys Glu Lys
            370                 375                 380

Asp Glu Met Val Glu Gln Glu Phe Asn Arg Leu Leu Glu Ala Thr Ser
385                 390                 395                 400

Tyr Leu Ser His Gln Leu Asp Phe Asn Val Leu Asn Asn Lys Pro Val
                    405                 410                 415

Ser Leu Gly Gln Ala Leu Glu Val Val Ile Gln Leu Gln Glu Lys His
                420                 425                 430

Val Lys Asp Glu Gln Ile Glu His Trp Lys Lys Ile Val Lys Thr Gln
            435                 440                 445

Glu Glu Leu Lys Glu Leu Leu Asn Lys Met Val Asn Leu Lys Glu Lys
            450                 455                 460

Ile Lys Glu Leu His Gln Gln Tyr Lys Glu Ala Ser Glu Val Lys Pro
465                 470                 475                 480

Pro Arg Asp Ile Thr Ala Glu Phe Leu Val Lys Ser Lys His Arg Asp
                485                 490                 495

Leu Thr Ala Leu Cys Lys Glu Tyr Asp Glu Leu Ala Glu Thr Gln Gly
                500                 505                 510

Lys Leu Glu Glu Lys Leu Gln Glu Leu Glu Ala Asn Pro Pro Ser Asp
            515                 520                 525

Val Tyr Leu Ser Ser Arg Asp Arg Gln Ile Leu Asp Trp His Phe Ala
            530                 535                 540

Asn Leu Glu Phe Ala Asn Ala Thr Pro Leu Ser Thr Leu Ser Leu Lys
545                 550                 555                 560

His Trp Asp Gln Asp Asp Asp Phe Glu Phe Thr Gly Ser His Leu Thr
                    565                 570                 575

Val Arg Asn Gly Tyr Ser Cys Val Pro Val Ala Leu Ala Glu Gly Leu
                580                 585                 590

Asp Ile Lys Leu Asn Thr Ala Val Arg Gln Val Arg Tyr Thr Ala Ser
            595                 600                 605

Gly Cys Glu Val Ile Ala Val Asn Thr Arg Ser Thr Ser Gln Thr Phe
            610                 615                 620

Ile Tyr Lys Cys Asp Ala Val Leu Cys Thr Leu Pro Leu Gly Val Leu
625                 630                 635                 640
```

```
Lys Gln Gln Pro Pro Ala Val Gln Phe Val Pro Pro Leu Pro Glu Trp
                645                 650                 655

Lys Thr Ser Ala Val Gln Arg Met Gly Phe Gly Asn Leu Asn Lys Val
            660                 665                 670

Val Leu Cys Phe Asp Arg Val Phe Trp Asp Pro Ser Val Asn Leu Phe
        675                 680                 685

Gly His Val Gly Ser Thr Thr Ala Ser Arg Gly Glu Leu Phe Leu Phe
    690                 695                 700

Trp Asn Leu Tyr Lys Ala Pro Ile Leu Leu Ala Leu Val Ala Gly Glu
705                 710                 715                 720

Ala Ala Gly Ile Met Glu Asn Ile Ser Asp Asp Val Ile Val Gly Arg
                725                 730                 735

Cys Leu Ala Ile Leu Lys Gly Ile Phe Gly Ser Ser Ala Val Pro Gln
            740                 745                 750

Pro Lys Glu Thr Val Val Ser Arg Trp Arg Ala Asp Pro Trp Ala Arg
        755                 760                 765

Gly Ser Tyr Ser Tyr Val Ala Ala Gly Ser Ser Gly Asn Asp Tyr Asp
    770                 775                 780

Leu Met Ala Gln Pro Ile Thr Pro Gly Pro Ser Ile Pro Gly Ala Pro
785                 790                 795                 800

Gln Pro Ile Pro Arg Leu Phe Phe Ala Gly Glu His Thr Ile Arg Asn
                805                 810                 815

Tyr Pro Ala Thr Val His Gly Ala Leu Leu Ser Gly Leu Arg Glu Ala
            820                 825                 830

Gly Arg Ile Ala Asp Gln Phe Leu Gly Ala Met Tyr Thr Leu Pro Arg
        835                 840                 845

Gln Ala Thr Pro Gly Val Pro Ala Gln Gln Ser Pro Ser Met
    850                 855                 860

<210> SEQ ID NO 8
<211> LENGTH: 21
<212> TYPE: DNA
<213> ORGANISM: Artificial Sequence
<220> FEATURE:
<223> OTHER INFORMATION: Tbp fw Primer

<400> SEQUENCE: 8
gaagctgcgg tacaattcca g                                           21

<210> SEQ ID NO 9
<211> LENGTH: 21
<212> TYPE: DNA
<213> ORGANISM: Artificial Sequence
<220> FEATURE:
<223> OTHER INFORMATION: Tbp rev Primer

<400> SEQUENCE: 9
ccccttgtac ccttcaccaa t                                           21

<210> SEQ ID NO 10
<211> LENGTH: 19
<212> TYPE: DNA
<213> ORGANISM: Artificial Sequence
<220> FEATURE:
<223> OTHER INFORMATION: 36B4 fw Primer

<400> SEQUENCE: 10
gcgtcctggc attgtctgt                                              19
```

<210> SEQ ID NO 11
<211> LENGTH: 21
<212> TYPE: DNA
<213> ORGANISM: Artificial Sequence
<220> FEATURE:
<223> OTHER INFORMATION: 36B4 rev Primer

<400> SEQUENCE: 11
gcaaatgcag atggatcagc c                                              21

<210> SEQ ID NO 12
<211> LENGTH: 23
<212> TYPE: DNA
<213> ORGANISM: Artificial Sequence
<220> FEATURE:
<223> OTHER INFORMATION: HPRT fw Primer

<400> SEQUENCE: 12
agggcatatc caacaacaaa ctt                                            23

<210> SEQ ID NO 13
<211> LENGTH: 21
<212> TYPE: DNA
<213> ORGANISM: Artificial Sequence
<220> FEATURE:
<223> OTHER INFORMATION: HPRT rev Primer

<400> SEQUENCE: 13
gttaagcagt acagccccaa a                                              21

<210> SEQ ID NO 14
<211> LENGTH: 20
<212> TYPE: DNA
<213> ORGANISM: Artificial Sequence
<220> FEATURE:
<223> OTHER INFORMATION: Prdm16 fw Primer

<400> SEQUENCE: 14
cccccaacgc tctcggatcc                                                20

<210> SEQ ID NO 15
<211> LENGTH: 20
<212> TYPE: DNA
<213> ORGANISM: Artificial Sequence
<220> FEATURE:
<223> OTHER INFORMATION: Prdm16 rev Primer

<400> SEQUENCE: 15
ccgaagcagc ggttgcacag                                                20

<210> SEQ ID NO 16
<211> LENGTH: 23
<212> TYPE: DNA
<213> ORGANISM: Artificial Sequence
<220> FEATURE:
<223> OTHER INFORMATION: Pgc1a fw Primer

<400> SEQUENCE: 16
aagtgtggaa ctctctggaa ctg                                            23

<210> SEQ ID NO 17
<211> LENGTH: 23
<212> TYPE: DNA
<213> ORGANISM: Artificial Sequence
<220> FEATURE:
<223> OTHER INFORMATION: Pgc1a rev

<400> SEQUENCE: 17
gggttatctt ggttggcttt atg                                    23

<210> SEQ ID NO 18
<211> LENGTH: 19
<212> TYPE: DNA
<213> ORGANISM: Artificial Sequence
<220> FEATURE:
<223> OTHER INFORMATION: Ucp1 fw Primer

<400> SEQUENCE: 18
tggcaaaaac agaaggatt                                         19

<210> SEQ ID NO 19
<211> LENGTH: 19
<212> TYPE: DNA
<213> ORGANISM: Artificial Sequence
<220> FEATURE:
<223> OTHER INFORMATION: Ucp1 rev Primer

<400> SEQUENCE: 19
cgagtcgcag aaaagaagc                                         19

<210> SEQ ID NO 20
<211> LENGTH: 21
<212> TYPE: DNA
<213> ORGANISM: Artificial Sequence
<220> FEATURE:
<223> OTHER INFORMATION: Cidea fw Primer

<400> SEQUENCE: 20
tgctcttctg tatcgcccag t                                      21

<210> SEQ ID NO 21
<211> LENGTH: 21
<212> TYPE: DNA
<213> ORGANISM: Artificial Sequence
<220> FEATURE:
<223> OTHER INFORMATION: Cidea rev Primer

<400> SEQUENCE: 21
gccgtgttaa ggaatctgct g                                      21

<210> SEQ ID NO 22
<211> LENGTH: 21
<212> TYPE: DNA
<213> ORGANISM: Artificial Sequence
<220> FEATURE:
<223> OTHER INFORMATION: Ucp2 fw Primer

<400> SEQUENCE: 22
accaagggct cagagcatgc a                                      21

<210> SEQ ID NO 23
<211> LENGTH: 21
<212> TYPE: DNA
<213> ORGANISM: Artificial Sequence
<220> FEATURE:
<223> OTHER INFORMATION: Ucp2 rev Primer

<400> SEQUENCE: 23
aggtcaccag ctcagcacag t                                      21

<210> SEQ ID NO 24

```
<211> LENGTH: 25
<212> TYPE: DNA
<213> ORGANISM: Artificial Sequence
<220> FEATURE:
<223> OTHER INFORMATION: Ucp3 fw Primer

<400> SEQUENCE: 24
actccagcgt cgccatcagg attct                                         25

<210> SEQ ID NO 25
<211> LENGTH: 25
<212> TYPE: DNA
<213> ORGANISM: Artificial Sequence
<220> FEATURE:
<223> OTHER INFORMATION: Ucp3 rev Primer

<400> SEQUENCE: 25
taaacaggtg agactccagc aactt                                         25

<210> SEQ ID NO 26
<211> LENGTH: 20
<212> TYPE: DNA
<213> ORGANISM: Artificial Sequence
<220> FEATURE:
<223> OTHER INFORMATION: Cpt1b fw Primer

<400> SEQUENCE: 26
cagctggctg gttgttgtca                                               20

<210> SEQ ID NO 27
<211> LENGTH: 20
<212> TYPE: DNA
<213> ORGANISM: Artificial Sequence
<220> FEATURE:
<223> OTHER INFORMATION: Cpt1b rev Primer

<400> SEQUENCE: 27
ttgtcggaag aagaaaatgc                                               20

<210> SEQ ID NO 28
<211> LENGTH: 20
<212> TYPE: DNA
<213> ORGANISM: Artificial Sequence
<220> FEATURE:
<223> OTHER INFORMATION: Acads fw Primer

<400> SEQUENCE: 28
tcgctggtcc cttcgtagat                                               20

<210> SEQ ID NO 29
<211> LENGTH: 20
<212> TYPE: DNA
<213> ORGANISM: Artificial Sequence
<220> FEATURE:
<223> OTHER INFORMATION: Acads rev Primer

<400> SEQUENCE: 29
tgggatgggc ttcaaaatag                                               20

<210> SEQ ID NO 30
<211> LENGTH: 22
<212> TYPE: DNA
<213> ORGANISM: Artificial Sequence
<220> FEATURE:
<223> OTHER INFORMATION: Hadhb fw Primer

<400> SEQUENCE: 30
```

```
ttcccaactg cactctgccc ca                                         22
```

<210> SEQ ID NO 31
<211> LENGTH: 23
<212> TYPE: DNA
<213> ORGANISM: Artificial Sequence
<220> FEATURE:
<223> OTHER INFORMATION: Hadhb rev Primer

<400> SEQUENCE: 31

```
agcagaaatg gaatgcggac ccc                                        23
```

<210> SEQ ID NO 32
<211> LENGTH: 21
<212> TYPE: DNA
<213> ORGANISM: Artificial Sequence
<220> FEATURE:
<223> OTHER INFORMATION: Fabp3 fw Primer

<400> SEQUENCE: 32

```
tgacgctgga cggaggcaaa c                                          21
```

<210> SEQ ID NO 33
<211> LENGTH: 20
<212> TYPE: DNA
<213> ORGANISM: Artificial Sequence
<220> FEATURE:
<223> OTHER INFORMATION: Fabp3 rev Primer

<400> SEQUENCE: 33

```
gacggagcag ccaggtcacg                                            20
```

<210> SEQ ID NO 34
<211> LENGTH: 20
<212> TYPE: DNA
<213> ORGANISM: Artificial Sequence
<220> FEATURE:
<223> OTHER INFORMATION: Cox8b fw Primer

<400> SEQUENCE: 34

```
gaaccatgaa gccaacgact                                            20
```

<210> SEQ ID NO 35
<211> LENGTH: 20
<212> TYPE: DNA
<213> ORGANISM: Artificial Sequence
<220> FEATURE:
<223> OTHER INFORMATION: Cox8b rev Primer

<400> SEQUENCE: 35

```
gcgaagttca cagtggttcc                                            20
```

<210> SEQ ID NO 36
<211> LENGTH: 20
<212> TYPE: DNA
<213> ORGANISM: Artificial Sequence
<220> FEATURE:
<223> OTHER INFORMATION: Acaca fw Primer

<400> SEQUENCE: 36

```
gggctgctaa ggtggaagta                                            20
```

<210> SEQ ID NO 37
<211> LENGTH: 20
<212> TYPE: DNA

<213> ORGANISM: Artificial Sequence
<220> FEATURE:
<223> OTHER INFORMATION: Acaca rev Primer

<400> SEQUENCE: 37
aagttgagga agatgtggtt                                               20

<210> SEQ ID NO 38
<211> LENGTH: 20
<212> TYPE: DNA
<213> ORGANISM: Artificial Sequence
<220> FEATURE:
<223> OTHER INFORMATION: Tnfa fw Primer

<400> SEQUENCE: 38
tcgtagcaaa ccaccaagtg                                               20

<210> SEQ ID NO 39
<211> LENGTH: 20
<212> TYPE: DNA
<213> ORGANISM: Artificial Sequence
<220> FEATURE:
<223> OTHER INFORMATION: Tnfa rev Primer

<400> SEQUENCE: 39
agatagcaaa tcggctgacg                                               20

<210> SEQ ID NO 40
<211> LENGTH: 22
<212> TYPE: DNA
<213> ORGANISM: Artificial Sequence
<220> FEATURE:
<223> OTHER INFORMATION: Adipoq fw Primer

<400> SEQUENCE: 40
gcactggcaa gttctactgc aa                                            22

<210> SEQ ID NO 41
<211> LENGTH: 23
<212> TYPE: DNA
<213> ORGANISM: Artificial Sequence
<220> FEATURE:
<223> OTHER INFORMATION: Adipoq rev Primer

<400> SEQUENCE: 41
gtaggtgaag agaacggcct tgt                                           23

<210> SEQ ID NO 42
<211> LENGTH: 20
<212> TYPE: DNA
<213> ORGANISM: Artificial Sequence
<220> FEATURE:
<223> OTHER INFORMATION: Lep fw Primer

<400> SEQUENCE: 42
cctgctccag cagctgcaag                                               20

<210> SEQ ID NO 43
<211> LENGTH: 21
<212> TYPE: DNA
<213> ORGANISM: Artificial Sequence
<220> FEATURE:
<223> OTHER INFORMATION: Lep rev Primer

<400> SEQUENCE: 43
accgacacag gggtctccag c                                             21

<210> SEQ ID NO 44
<211> LENGTH: 21
<212> TYPE: DNA
<213> ORGANISM: Artificial Sequence
<220> FEATURE:
<223> OTHER INFORMATION: Agt fw Primer

<400> SEQUENCE: 44
gcaccctggt ctctttctac c                                        21

<210> SEQ ID NO 45
<211> LENGTH: 21
<212> TYPE: DNA
<213> ORGANISM: Artificial Sequence
<220> FEATURE:
<223> OTHER INFORMATION: Agt rev Primer

<400> SEQUENCE: 45
tgtgtccatc tagtcgggag g                                        21

<210> SEQ ID NO 46
<211> LENGTH: 20
<212> TYPE: DNA
<213> ORGANISM: Artificial Sequence
<220> FEATURE:
<223> OTHER INFORMATION: Fabp4 fw Primer

<400> SEQUENCE: 46
agggcaatga ggtcacatcc                                          20

<210> SEQ ID NO 47
<211> LENGTH: 23
<212> TYPE: DNA
<213> ORGANISM: Artificial Sequence
<220> FEATURE:
<223> OTHER INFORMATION: Fabp4 rev Primer

<400> SEQUENCE: 47
gcatctcgtt atccgagtac cag                                      23

<210> SEQ ID NO 48
<211> LENGTH: 21
<212> TYPE: DNA
<213> ORGANISM: Artificial Sequence
<220> FEATURE:
<223> OTHER INFORMATION: Retn fw Primer

<400> SEQUENCE: 48
ctgtccagtc tatccttgca c                                        21

<210> SEQ ID NO 49
<211> LENGTH: 21
<212> TYPE: DNA
<213> ORGANISM: Artificial Sequence
<220> FEATURE:
<223> OTHER INFORMATION: Retn rev Primer

<400> SEQUENCE: 49
cagaaggcac agcagtcttg a                                        21

<210> SEQ ID NO 50
<211> LENGTH: 22
<212> TYPE: DNA
<213> ORGANISM: Artificial Sequence
<220> FEATURE:

<223> OTHER INFORMATION: Pparg fw Primer

<400> SEQUENCE: 50
gaaagacaac ggacaaatca cc        22

<210> SEQ ID NO 51
<211> LENGTH: 22
<212> TYPE: DNA
<213> ORGANISM: Artificial Sequence
<220> FEATURE:
<223> OTHER INFORMATION: Pparg rev Primer

<400> SEQUENCE: 51
gggggtgata tgtttgaact tg        22

<210> SEQ ID NO 52
<211> LENGTH: 20
<212> TYPE: DNA
<213> ORGANISM: Artificial Sequence
<220> FEATURE:
<223> OTHER INFORMATION: Nrf1 fw Primer

<400> SEQUENCE: 52
tggagtccaa gatgctaatg        20

<210> SEQ ID NO 53
<211> LENGTH: 20
<212> TYPE: DNA
<213> ORGANISM: Artificial Sequence
<220> FEATURE:
<223> OTHER INFORMATION: Nrf1 rev Primer

<400> SEQUENCE: 53
agagctccat gctactgttc        20

<210> SEQ ID NO 54
<211> LENGTH: 21
<212> TYPE: DNA
<213> ORGANISM: Artificial Sequence
<220> FEATURE:
<223> OTHER INFORMATION: Tfam fw Primer

<400> SEQUENCE: 54
aggcccggca gagacggtta a        21

<210> SEQ ID NO 55
<211> LENGTH: 23
<212> TYPE: DNA
<213> ORGANISM: Artificial Sequence
<220> FEATURE:
<223> OTHER INFORMATION: Tfam rev Primer

<400> SEQUENCE: 55
cctgagccga atcatccttt gcc        23

<210> SEQ ID NO 56
<211> LENGTH: 20
<212> TYPE: DNA
<213> ORGANISM: Artificial Sequence
<220> FEATURE:
<223> OTHER INFORMATION: Ndufa6 fw Primer

<400> SEQUENCE: 56
gtcacagacc ccagagtggt        20

```
<210> SEQ ID NO 57
<211> LENGTH: 20
<212> TYPE: DNA
<213> ORGANISM: Artificial Sequence
<220> FEATURE:
<223> OTHER INFORMATION: Ndufa6 rev Primer

<400> SEQUENCE: 57
taacatgcac cttcccatca                                              20

<210> SEQ ID NO 58
<211> LENGTH: 20
<212> TYPE: DNA
<213> ORGANISM: Artificial Sequence
<220> FEATURE:
<223> OTHER INFORMATION: Sdha fw Primer

<400> SEQUENCE: 58
acacagacct ggtggagacc                                              20

<210> SEQ ID NO 59
<211> LENGTH: 20
<212> TYPE: DNA
<213> ORGANISM: Artificial Sequence
<220> FEATURE:
<223> OTHER INFORMATION: Sdha rev Primer

<400> SEQUENCE: 59
ggatgggctt ggagtaatca                                              20

<210> SEQ ID NO 60
<211> LENGTH: 15
<212> TYPE: DNA
<213> ORGANISM: Artificial Sequence
<220> FEATURE:
<223> OTHER INFORMATION: Uqcrc1 fw Primer

<400> SEQUENCE: 60
gacaacgtga ccctc                                                   15

<210> SEQ ID NO 61
<211> LENGTH: 20
<212> TYPE: DNA
<213> ORGANISM: Artificial Sequence
<220> FEATURE:
<223> OTHER INFORMATION: Uqcrc1 rev Primer

<400> SEQUENCE: 61
gacaacgtga ccctccaagt                                              20

<210> SEQ ID NO 62
<211> LENGTH: 20
<212> TYPE: DNA
<213> ORGANISM: Artificial Sequence
<220> FEATURE:
<223> OTHER INFORMATION: Cox6a1 fw Primer

<400> SEQUENCE: 62
tgctcaacgt gttcctcaag                                              20

<210> SEQ ID NO 63
<211> LENGTH: 20
<212> TYPE: DNA
<213> ORGANISM: Artificial Sequence
<220> FEATURE:
<223> OTHER INFORMATION: Cox6a1 rev Primer
```

<400> SEQUENCE: 63
taagggtcca aaaccagtgc							20

<210> SEQ ID NO 64
<211> LENGTH: 20
<212> TYPE: DNA
<213> ORGANISM: Artificial Sequence
<220> FEATURE:
<223> OTHER INFORMATION: Atp5b fw Primer

<400> SEQUENCE: 64
gagggattac cacccatcct							20

<210> SEQ ID NO 65
<211> LENGTH: 20
<212> TYPE: DNA
<213> ORGANISM: Artificial Sequence
<220> FEATURE:
<223> OTHER INFORMATION: Atp5b rev Primer

<400> SEQUENCE: 65
catgattctg cccaaggtct							20

<210> SEQ ID NO 66
<211> LENGTH: 19
<212> TYPE: DNA
<213> ORGANISM: Artificial Sequence
<220> FEATURE:
<223> OTHER INFORMATION: Slc27a1 fw Primer

<400> SEQUENCE: 66
ctgggacttc cgtggacct							19

<210> SEQ ID NO 67
<211> LENGTH: 21
<212> TYPE: DNA
<213> ORGANISM: Artificial Sequence
<220> FEATURE:
<223> OTHER INFORMATION: Slc27a1 rev Primer

<400> SEQUENCE: 67
tcttgcagac gatacgcaga a							21

<210> SEQ ID NO 68
<211> LENGTH: 21
<212> TYPE: DNA
<213> ORGANISM: Artificial Sequence
<220> FEATURE:
<223> OTHER INFORMATION: Cd40 fw Primer

<400> SEQUENCE: 68
ttgttgacag cggtccatct a							21

<210> SEQ ID NO 69
<211> LENGTH: 21
<212> TYPE: DNA
<213> ORGANISM: Artificial Sequence
<220> FEATURE:
<223> OTHER INFORMATION: Cd40 rev Primer

<400> SEQUENCE: 69
ccatcgtgga ggtactgttt g							21

<210> SEQ ID NO 70
<211> LENGTH: 23

```
<212> TYPE: DNA
<213> ORGANISM: Artificial Sequence
<220> FEATURE:
<223> OTHER INFORMATION: Klhl13 fw Primer

<400> SEQUENCE: 70
agaattggtt gctgcaatac tcc                                          23

<210> SEQ ID NO 71
<211> LENGTH: 21
<212> TYPE: DNA
<213> ORGANISM: Artificial Sequence
<220> FEATURE:
<223> OTHER INFORMATION: Klhl13 rev Primer

<400> SEQUENCE: 71
aaggcacagt ttcaagtgct g                                            21

<210> SEQ ID NO 72
<211> LENGTH: 20
<212> TYPE: DNA
<213> ORGANISM: Artificial Sequence
<220> FEATURE:
<223> OTHER INFORMATION: Ear2 fw Primer

<400> SEQUENCE: 72
cctgtaaccc cagaactcca                                              20

<210> SEQ ID NO 73
<211> LENGTH: 20
<212> TYPE: DNA
<213> ORGANISM: Artificial Sequence
<220> FEATURE:
<223> OTHER INFORMATION: Ear2 rev Primer

<400> SEQUENCE: 73
cagatgagca aaggtgcaaa                                              20

<210> SEQ ID NO 74
<211> LENGTH: 19
<212> TYPE: DNA
<213> ORGANISM: Artificial Sequence
<220> FEATURE:
<223> OTHER INFORMATION: Tmem26 fw Primer

<400> SEQUENCE: 74
accctgtcat cccacagag                                               19

<210> SEQ ID NO 75
<211> LENGTH: 22
<212> TYPE: DNA
<213> ORGANISM: Artificial Sequence
<220> FEATURE:
<223> OTHER INFORMATION: Tmem26 rev Primer

<400> SEQUENCE: 75
tgtttggtgg agtcctaagg tc                                           22

<210> SEQ ID NO 76
<211> LENGTH: 22
<212> TYPE: DNA
<213> ORGANISM: Artificial Sequence
<220> FEATURE:
<223> OTHER INFORMATION: Cd137 fw Primer

<400> SEQUENCE: 76
```
cgtgcagaac tcctgtgata ac         22

<210> SEQ ID NO 77
<211> LENGTH: 21
<212> TYPE: DNA
<213> ORGANISM: Artificial Sequence
<220> FEATURE:
<223> OTHER INFORMATION: Cd137 rev Primer

<400> SEQUENCE: 77
gtccacctat gctggagaag g          21

<210> SEQ ID NO 78
<211> LENGTH: 21
<212> TYPE: DNA
<213> ORGANISM: Artificial Sequence
<220> FEATURE:
<223> OTHER INFORMATION: Sp100 fw Primer

<400> SEQUENCE: 78
tgatggaggg aacccaaact c          21

<210> SEQ ID NO 79
<211> LENGTH: 21
<212> TYPE: DNA
<213> ORGANISM: Artificial Sequence
<220> FEATURE:
<223> OTHER INFORMATION: Sp100 rev Primer

<400> SEQUENCE: 79
tgatggaggg aacccaaact c          21

<210> SEQ ID NO 80
<211> LENGTH: 19
<212> TYPE: DNA
<213> ORGANISM: Artificial Sequence
<220> FEATURE:
<223> OTHER INFORMATION: Tbx1 fw Primer

<400> SEQUENCE: 80
ggcaggcaga cgaatgttc             19

<210> SEQ ID NO 81
<211> LENGTH: 21
<212> TYPE: DNA
<213> ORGANISM: Artificial Sequence
<220> FEATURE:
<223> OTHER INFORMATION: Tbx1 rev Primer

<400> SEQUENCE: 81
ttgtcatcta cgggcacaaa g          21

<210> SEQ ID NO 82
<211> LENGTH: 20
<212> TYPE: DNA
<213> ORGANISM: Artificial Sequence
<220> FEATURE:
<223> OTHER INFORMATION: Pdk4 fw Primer

<400> SEQUENCE: 82
caaggagatc tgaatctcta            20

<210> SEQ ID NO 83
<211> LENGTH: 20
<212> TYPE: DNA
<213> ORGANISM: Artificial Sequence

```
<220> FEATURE:
<223> OTHER INFORMATION: Pdk4 rev Primer

<400> SEQUENCE: 83
gataatgttt gaaggctgac                                                    20

<210> SEQ ID NO 84
<211> LENGTH: 22
<212> TYPE: DNA
<213> ORGANISM: Artificial Sequence
<220> FEATURE:
<223> OTHER INFORMATION: Eva1 fw Primer

<400> SEQUENCE: 84
ccacttctcc tgagtttaca gc                                                 22

<210> SEQ ID NO 85
<211> LENGTH: 23
<212> TYPE: DNA
<213> ORGANISM: Artificial Sequence
<220> FEATURE:
<223> OTHER INFORMATION: Eva1 rev Primer

<400> SEQUENCE: 85
gcattttaac cgaacatctg tcc                                                23

<210> SEQ ID NO 86
<211> LENGTH: 22
<212> TYPE: DNA
<213> ORGANISM: Artificial Sequence
<220> FEATURE:
<223> OTHER INFORMATION: Fbxo31 fw Primer

<400> SEQUENCE: 86
aaactgcttc accgatacag ac                                                 22

<210> SEQ ID NO 87
<211> LENGTH: 20
<212> TYPE: DNA
<213> ORGANISM: Artificial Sequence
<220> FEATURE:
<223> OTHER INFORMATION: Fxbo31 rev Primer

<400> SEQUENCE: 87
accacgacgt tcagcaatcc                                                    20

<210> SEQ ID NO 88
<211> LENGTH: 19
<212> TYPE: DNA
<213> ORGANISM: Artificial Sequence
<220> FEATURE:
<223> OTHER INFORMATION: Acot2 fw Primer

<400> SEQUENCE: 88
atggtggcct cgtctttcg                                                     19

<210> SEQ ID NO 89
<211> LENGTH: 19
<212> TYPE: DNA
<213> ORGANISM: Artificial Sequence
<220> FEATURE:
<223> OTHER INFORMATION: Acot2 rev Primer

<400> SEQUENCE: 89
gagcggcgga ggtacaaac                                                     19
```

<210> SEQ ID NO 90
<211> LENGTH: 20
<212> TYPE: DNA
<213> ORGANISM: Artificial Sequence
<220> FEATURE:
<223> OTHER INFORMATION: Ebf3 fw Primer

<400> SEQUENCE: 90
cgaaaggacc gcttttgtgg                                               20

<210> SEQ ID NO 91
<211> LENGTH: 21
<212> TYPE: DNA
<213> ORGANISM: Artificial Sequence
<220> FEATURE:
<223> OTHER INFORMATION: Ebf3 rev Primer

<400> SEQUENCE: 91
agtgaatgcc gttgttggtt t                                             21

<210> SEQ ID NO 92
<211> LENGTH: 23
<212> TYPE: DNA
<213> ORGANISM: Artificial Sequence
<220> FEATURE:
<223> OTHER INFORMATION: Hspb7 fw Primer

<400> SEQUENCE: 92
gagcatgttt tcagacgact ttg                                           23

<210> SEQ ID NO 93
<211> LENGTH: 22
<212> TYPE: DNA
<213> ORGANISM: Artificial Sequence
<220> FEATURE:
<223> OTHER INFORMATION: Hspb7 rev Primer

<400> SEQUENCE: 93
ccgagggtct tgatgtttcc tt                                            22

<210> SEQ ID NO 94
<211> LENGTH: 21
<212> TYPE: DNA
<213> ORGANISM: Artificial Sequence
<220> FEATURE:
<223> OTHER INFORMATION: Slc29a1 fw Primer

<400> SEQUENCE: 94
caccagcctc aggacaggta t                                             21

<210> SEQ ID NO 95
<211> LENGTH: 19
<212> TYPE: DNA
<213> ORGANISM: Artificial Sequence
<220> FEATURE:
<223> OTHER INFORMATION: Slc29a1 rev Primer

<400> SEQUENCE: 95
gtccaggcgg tttgtgaaa                                                19

<210> SEQ ID NO 96
<211> LENGTH: 20
<212> TYPE: DNA
<213> ORGANISM: Artificial Sequence
<220> FEATURE:
<223> OTHER INFORMATION: Oplah fw Primer

<400> SEQUENCE: 96
cttcacgcac gtctccttgt                                           20

<210> SEQ ID NO 97
<211> LENGTH: 19
<212> TYPE: DNA
<213> ORGANISM: Artificial Sequence
<220> FEATURE:
<223> OTHER INFORMATION: Oplah rev Primer

<400> SEQUENCE: 97
gcatctgcac aggccgtat                                            19

<210> SEQ ID NO 98
<211> LENGTH: 20
<212> TYPE: DNA
<213> ORGANISM: Artificial Sequence
<220> FEATURE:
<223> OTHER INFORMATION: Cs fw Primer

<400> SEQUENCE: 98
cagctacaga aggaagttgg                                           20

<210> SEQ ID NO 99
<211> LENGTH: 20
<212> TYPE: DNA
<213> ORGANISM: Artificial Sequence
<220> FEATURE:
<223> OTHER INFORMATION: Cs rev Primer

<400> SEQUENCE: 99
aggaatagcg agggtcagtc                                           20

<210> SEQ ID NO 100
<211> LENGTH: 25
<212> TYPE: DNA
<213> ORGANISM: Artificial Sequence
<220> FEATURE:
<223> OTHER INFORMATION: Gapdh fw Primer

<400> SEQUENCE: 100
tgccaagtat gatgacatca agaag                                     25

<210> SEQ ID NO 101
<211> LENGTH: 22
<212> TYPE: DNA
<213> ORGANISM: Artificial Sequence
<220> FEATURE:
<223> OTHER INFORMATION: Gapdh rev Primer

<400> SEQUENCE: 101
ggtcctcagt gtagcccaag at                                        22

<210> SEQ ID NO 102
<211> LENGTH: 20
<212> TYPE: DNA
<213> ORGANISM: Artificial Sequence
<220> FEATURE:
<223> OTHER INFORMATION: hLSD1 fw Primer

<400> SEQUENCE: 102
gctcggggct cttattccta                                           20

<210> SEQ ID NO 103

```
<211> LENGTH: 20
<212> TYPE: DNA
<213> ORGANISM: Artificial Sequence
<220> FEATURE:
<223> OTHER INFORMATION: hLSD1 rev Primer

<400> SEQUENCE: 103
atgttctccc gcaaagaaga                                              20

<210> SEQ ID NO 104
<211> LENGTH: 20
<212> TYPE: DNA
<213> ORGANISM: Artificial Sequence
<220> FEATURE:
<223> OTHER INFORMATION: Rosa26-LSD1Mut fw Primer

<400> SEQUENCE: 104
tcttctttgc gggagaacat                                              20

<210> SEQ ID NO 105
<211> LENGTH: 20
<212> TYPE: DNA
<213> ORGANISM: Artificial Sequence
<220> FEATURE:
<223> OTHER INFORMATION: Rosa26-LSD1Mut rev Primer

<400> SEQUENCE: 105
cgcctctagc tcacatgctt                                              20

<210> SEQ ID NO 106
<211> LENGTH: 20
<212> TYPE: DNA
<213> ORGANISM: Artificial Sequence
<220> FEATURE:
<223> OTHER INFORMATION: mLsd1 fw Primer

<400> SEQUENCE: 106
gtgttctggg acccaagtgt                                              20

<210> SEQ ID NO 107
<211> LENGTH: 20
<212> TYPE: DNA
<213> ORGANISM: Artificial Sequence
<220> FEATURE:
<223> OTHER INFORMATION: mLsd1 rev Primer

<400> SEQUENCE: 107
taatgccagc agcttctcct                                              20

<210> SEQ ID NO 108
<211> LENGTH: 20
<212> TYPE: DNA
<213> ORGANISM: Artificial Sequence
<220> FEATURE:
<223> OTHER INFORMATION: Rosa26-LSD1 fw Primer

<400> SEQUENCE: 108
aatgccttcg aattcagcac                                              20

<210> SEQ ID NO 109
<211> LENGTH: 20
<212> TYPE: DNA
<213> ORGANISM: Artificial Sequence
<220> FEATURE:
<223> OTHER INFORMATION: Rosa26-LSD1 rev Primer

<400> SEQUENCE: 109
```

```
ccttgtcatc gtcgtccttg                                                  20
```

<210> SEQ ID NO 110
<211> LENGTH: 20
<212> TYPE: DNA
<213> ORGANISM: Artificial Sequence
<220> FEATURE:
<223> OTHER INFORMATION: Lsd1 WT/L2 fw Primer

<400> SEQUENCE: 110

```
cctcagtagg cctggtttgt                                                  20
```

<210> SEQ ID NO 111
<211> LENGTH: 20
<212> TYPE: DNA
<213> ORGANISM: Artificial Sequence
<220> FEATURE:
<223> OTHER INFORMATION: Lsd1WT/L2 rev Primer

<400> SEQUENCE: 111

```
ttggttttgg ttgacccttc                                                  20
```

<210> SEQ ID NO 112
<211> LENGTH: 20
<212> TYPE: DNA
<213> ORGANISM: Artificial Sequence
<220> FEATURE:
<223> OTHER INFORMATION: Lsd1 L- fw Primer

<400> SEQUENCE: 112

```
ccgtggaaat tcgtgcactc                                                  20
```

<210> SEQ ID NO 113
<211> LENGTH: 22
<212> TYPE: DNA
<213> ORGANISM: Artificial Sequence
<220> FEATURE:
<223> OTHER INFORMATION: Lsd L- rev Primer

<400> SEQUENCE: 113

```
gcaggcggtt tgaaatgtat tc                                               22
```

<210> SEQ ID NO 114
<211> LENGTH: 25
<212> TYPE: DNA
<213> ORGANISM: Artificial Sequence
<220> FEATURE:
<223> OTHER INFORMATION: Cre fw Primer

<400> SEQUENCE: 114

```
ttcccgcaga acctgaagat gttcg                                            25
```

<210> SEQ ID NO 115
<211> LENGTH: 28
<212> TYPE: DNA
<213> ORGANISM: Artificial Sequence
<220> FEATURE:
<223> OTHER INFORMATION: Cre rev Primer

<400> SEQUENCE: 115

```
gggtgttata agcaatcccc agaaatgc                                         28
```

<210> SEQ ID NO 116
<211> LENGTH: 20
<212> TYPE: DNA

```
<213> ORGANISM: Artificial Sequence
<220> FEATURE:
<223> OTHER INFORMATION: Cox2 fw Primer

<400> SEQUENCE: 116
cagtcccctc cctaggactt                                              20

<210> SEQ ID NO 117
<211> LENGTH: 22
<212> TYPE: DNA
<213> ORGANISM: Artificial Sequence
<220> FEATURE:
<223> OTHER INFORMATION: Cox2 rev Primer

<400> SEQUENCE: 117
tttcagagca ttggccatag aa                                           22

<210> SEQ ID NO 118
<211> LENGTH: 20
<212> TYPE: DNA
<213> ORGANISM: Artificial Sequence
<220> FEATURE:
<223> OTHER INFORMATION: Fasn fw Primer

<400> SEQUENCE: 118
aggatatgga gagggctggt                                              20

<210> SEQ ID NO 119
<211> LENGTH: 20
<212> TYPE: DNA
<213> ORGANISM: Artificial Sequence
<220> FEATURE:
<223> OTHER INFORMATION: Fasn rev Primer

<400> SEQUENCE: 119
acccaagcat cattttcgtc                                              20

<210> SEQ ID NO 120
<211> LENGTH: 20
<212> TYPE: DNA
<213> ORGANISM: Artificial Sequence
<220> FEATURE:
<223> OTHER INFORMATION: C/ebpalpha fw Primer

<400> SEQUENCE: 120
ttacaacagg ccaggtttcc                                              20

<210> SEQ ID NO 121
<211> LENGTH: 20
<212> TYPE: DNA
<213> ORGANISM: Artificial Sequence
<220> FEATURE:
<223> OTHER INFORMATION: C/ebpalpha rev Primer

<400> SEQUENCE: 121
ctctgggatg gatcgattgt                                              20

<210> SEQ ID NO 122
<211> LENGTH: 20
<212> TYPE: DNA
<213> ORGANISM: Artificial Sequence
<220> FEATURE:
<223> OTHER INFORMATION: C/ebpbeta fw Primer

<400> SEQUENCE: 122
caagctgagc gacgagtaca                                              20
```

```
<210> SEQ ID NO 123
<211> LENGTH: 20
<212> TYPE: DNA
<213> ORGANISM: Artificial Sequence
<220> FEATURE:
<223> OTHER INFORMATION: C/ebpbeta rev Primer

<400> SEQUENCE: 123
agctgctcca ccttcttctg                                               20

<210> SEQ ID NO 124
<211> LENGTH: 20
<212> TYPE: DNA
<213> ORGANISM: Artificial Sequence
<220> FEATURE:
<223> OTHER INFORMATION: C/ebpdelta fw Primer

<400> SEQUENCE: 124
agaagctggt ggagttgtcg                                               20

<210> SEQ ID NO 125
<211> LENGTH: 20
<212> TYPE: DNA
<213> ORGANISM: Artificial Sequence
<220> FEATURE:
<223> OTHER INFORMATION: C/ebpdelta rev Primer

<400> SEQUENCE: 125
cgcaggtccc aaagaaacta                                               20

<210> SEQ ID NO 126
<211> LENGTH: 20
<212> TYPE: DNA
<213> ORGANISM: Artificial Sequence
<220> FEATURE:
<223> OTHER INFORMATION: Rxralpha fw Primer

<400> SEQUENCE: 126
gtcgagccca agactgagac                                               20

<210> SEQ ID NO 127
<211> LENGTH: 20
<212> TYPE: DNA
<213> ORGANISM: Artificial Sequence
<220> FEATURE:
<223> OTHER INFORMATION: Rxralpha rev Primer

<400> SEQUENCE: 127
tctaggggca gctcagaaaa                                               20

<210> SEQ ID NO 128
<211> LENGTH: 20
<212> TYPE: DNA
<213> ORGANISM: Artificial Sequence
<220> FEATURE:
<223> OTHER INFORMATION: beta-Actin fw Primer

<400> SEQUENCE: 128
ccctgtatgc ctctggtcgt                                               20

<210> SEQ ID NO 129
<211> LENGTH: 19
<212> TYPE: DNA
<213> ORGANISM: Artificial Sequence
<220> FEATURE:
```

```
<223> OTHER INFORMATION: beta-Actin rev Primer

<400> SEQUENCE: 129
atggcgtgag ggagagcat                                            19

<210> SEQ ID NO 130
<211> LENGTH: 25
<212> TYPE: RNA
<213> ORGANISM: Artificial Sequence
<220> FEATURE:
<223> OTHER INFORMATION: Nrf1 siRNA sense

<400> SEQUENCE: 130
uaugguagcc auguuucag uuugg                                      25

<210> SEQ ID NO 131
<211> LENGTH: 25
<212> TYPE: RNA
<213> ORGANISM: Artificial Sequence
<220> FEATURE:
<223> OTHER INFORMATION: Control-Nrf1 siRNA sense

<400> SEQUENCE: 131
uauuuggaug uaccugugga cuugg                                     25

<210> SEQ ID NO 132
<211> LENGTH: 25
<212> TYPE: RNA
<213> ORGANISM: Artificial Sequence
<220> FEATURE:
<223> OTHER INFORMATION: c/ebpbeta si RNA sense

<400> SEQUENCE: 132
ccaagaugcg caaccuggag acgca                                     25

<210> SEQ ID NO 133
<211> LENGTH: 25
<212> TYPE: RNA
<213> ORGANISM: Artificial Sequence
<220> FEATURE:
<223> OTHER INFORMATION: Control-C/epbbeta siRNA sense

<400> SEQUENCE: 133
ccaguacgcc aagucgagca aggca                                     25
```